United States Patent
Walker et al.

(10) Patent No.: US 11,939,311 B2
(45) Date of Patent: Mar. 26, 2024

(54) ACID-LABILE SURFACTANTS

(71) Applicant: Promega Corporation, Madison, WI (US)

(72) Inventors: Joel Walker, Madison, WI (US); Sergei Saveliev, Madison, WI (US); Zhiyang Zeng, Madison, WI (US); Robert Kargbo, Madison, WI (US); Hui Wang, Madison, WI (US); Sergiy Levin, Madison, WI (US); Valerie Ressler, Madison, WI (US); Jun Zhang, Madison, WI (US); Ce Shi, Madison, WI (US); Harry Tetsuo Uyeda, Madison, WI (US); Jean Osterman, Madison, WI (US); Min Zhou, Madison, WI (US); Prabin Rai, Madison, WI (US); Wenhui Zhou, Madison, WI (US)

(73) Assignee: Promega Corporation, Madison, WI (US)

( * ) Notice: Subject to any disclaimer, the term of this patent is extended or adjusted under 35 U.S.C. 154(b) by 612 days.

(21) Appl. No.: 16/986,682

(22) Filed: Aug. 6, 2020

(65) Prior Publication Data
US 2021/0040058 A1   Feb. 11, 2021

Related U.S. Application Data

(60) Provisional application No. 62/883,249, filed on Aug. 6, 2019.

(51) Int. Cl.
| | |
|---|---|
| *C07D 317/24* | (2006.01) |
| *C07C 309/15* | (2006.01) |
| *C12Q 1/37* | (2006.01) |
| *G01N 33/68* | (2006.01) |

(52) U.S. Cl.
CPC .......... *C07D 317/24* (2013.01); *C07C 309/15* (2013.01); *C12Q 1/37* (2013.01); *G01N 33/6848* (2013.01)

(58) Field of Classification Search
CPC .................................................... C07D 317/24
See application file for complete search history.

(56) References Cited

U.S. PATENT DOCUMENTS

| | | | |
|---|---|---|---|
| 8,445,223 B2 | 5/2013 | Powell et al. | |
| 2011/0282096 A1 | 11/2011 | Powell et al. | |
| 2018/0187127 A1 | 7/2018 | Saveliev et al. | |
| 2019/0263774 A1 | 8/2019 | Brousmiche | |

FOREIGN PATENT DOCUMENTS

| | | | |
|---|---|---|---|
| WO | WO 2003/102536 | 12/2003 | |
| WO | WO 2009/048611 | 4/2009 | |
| WO | WO-2009048611 A2 * | 4/2009 | ........... C07C 309/10 |

OTHER PUBLICATIONS

Wu, Fang, et al. "Comparison of surfactant-assisted shotgun methods using acid-labile surfactants and sodium dodecyl sulfate for membrane proteome analysis." Analytica chimica acta 698.1-2 (2011): 36-43. (Year: 2011).*
Int'l Search Report and Written Opinion for PCT/US2020/045140, dated Sep. 24, 2020 (12 Pages).

* cited by examiner

*Primary Examiner* — John S Kenyon
(74) *Attorney, Agent, or Firm* — Casimir Jones, S.C.; Anne M. Reynolds

(57) ABSTRACT

Provided herein are surfactant compounds that can be used to aid in preparation of protein samples for analysis, for example by mass spectrometry.

20 Claims, 4 Drawing Sheets

ACID-LABILE SURFACTANTS

CROSS-REFERENCE TO RELATED APPLICATIONS

This application claims priority to U.S. Provisional Patent Application No. 62/883,249, filed on Aug. 6, 2019, the entire contents of which are fully incorporated herein by reference.

FIELD

Provided herein are surfactant compounds that can be used to aid in preparation of protein samples for analysis, for example by mass spectrometry.

BACKGROUND

The preparation of protein samples for analysis, for example by mass spectrometry analysis, typically includes three main steps: solubilization, digestion, and peptide recovery. Not all commonly-used reagents are compatible with each step. For example, solubilizing agents such as surfactants (e.g., sodium dodecyl sulfate (SDS)) or denaturants (e.g., acetonitrile, urea, or guanidine) may inhibit proteases. Even when used in concentrations that can be tolerable for protease activity, the presence of these surfactants or denaturants interfere with subsequent analyses such as liquid chromatography or mass spectrometric analysis. Accordingly, removal of the surfactants and organic solvents is typically required before conducting further analysis of a sample. The manipulations required for removal of these reagents complicates the sample preparation process and may lead to loss of sample material.

The digestion step may also present a challenge in protein sample preparation. A typical protein digestion with trypsin requires overnight incubation to reach completion. Even after overnight incubation, some proteins that are resistant to digestion, such as membrane proteins, can remain intact. Current methods employed in an attempt to overcome these limitations and to speed the digestion process include the use of organic solvents (e.g., acetonitrile), elevated temperatures, denaturants (e.g., urea), and/or detergents (e.g., SDS) to improve protein solubilization and protein denaturation, thus improving digestion. However, these alternative methods and additives often result in incomplete cleavage and low reproducibility. The use of these reagents may also inhibit trypsin activity, interfere with HPLC separation, and suppress peptide detection in mass spectrometry.

In-gel protein digestion may bring other challenges to protein sample preparation. Success of in-gel digestion relies not only on efficient protein digestion, but also on efficient post-digestion peptide extraction from the gel, which can be time-consuming and is often only moderately efficient in terms of peptide recovery. Recovered peptides are generally limited to the size of about 2,500 Da, whereas longer peptides may remain trapped in the gel. Recovery of peptides with increased hydrophobicity may also be impacted.

Another procedure related to protein sample preparation includes analysis of post-translational protein modifications. About 60% of all human proteins are glycosylated. To analyze glycosylation, a glycan should be separated from a protein. Deglycosylation is typically performed using a glycosidase, but this can be a time-consuming process. Reagents such as SDS can improve deglycosylation, potentially by providing better access to glycan attachment sites for the glycosidases. However, SDS can interfere with downstream sample preparation steps, mass spectrometric analysis, and HPLC analysis.

SUMMARY

There is a need for improved methods for protein sample preparation, and for methods or reagents that are compatible with protein solubilization, digestion, and peptide recovery. Particularly, methods and reagents that do not inhibit protease activity and do not interfere with isolation and/or characterization techniques would be advantageous. There may be particular needs for in-gel digestion protocols to improve recovery of peptides from gels, for improved solubilizations and digestions of pelleted proteins, more efficient protein extraction from cells and tissues, and increased compatibility with glycosylated proteins.

Provided herein are surfactant compounds that may have good water-solubility and aqueous stability even at higher temperatures, and which may degrade under acidic conditions. Such surfactants may be useful as protein solubilization and/or digestion reagents without interfering with proteases or with protein fragment mass spectrometry analysis.

Embodiments of the present disclosure include a compound of formula (I):

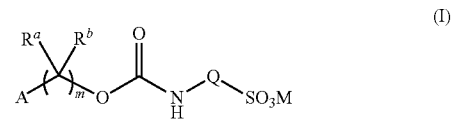

or a salt thereof, wherein:
A is selected from:

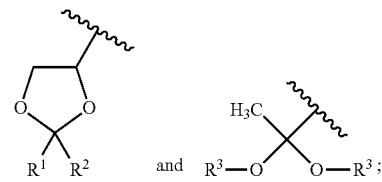

$R^1$ is selected from hydrogen, $C_1$-$C_{12}$ alkyl, $C_2$-$C_{12}$ alkenyl, and $C_1$-$C_{12}$ haloalkyl;
$R^2$ is selected from $C_4$-$C_{20}$ alkyl, $C_4$-$C_{20}$ alkenyl, $C_4$-$C_{20}$ haloalkyl;
each $R^3$ is independently selected from $C_1$-$C_{12}$ alkyl, $C_2$-$C_{12}$ alkenyl, and $C_1$-$C_{12}$ haloalkyl;
m is 1, 2, or 3;
$R^a$ and $R^b$, at each occurrence, are independently selected from hydrogen and $C_1$-$C_3$ alkyl;
Q is selected from $C_1$-$C_6$-alkylene, $C_1$-$C_6$-hydroxyalkylene, and a group of formula:

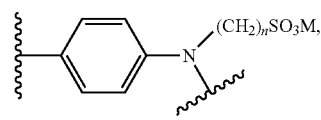

wherein n is 1, 2, 3, 4, 5, or 6; and
each M is independently selected from hydrogen, an alkali metal cation, and $NR_4^+$, wherein each R is independently selected from hydrogen and $C_1$-$C_{12}$ alkyl.

In some embodiments, A is:

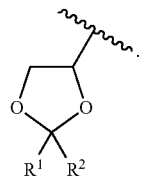

In some embodiments, $R^2$ is $C_6$-$C_{12}$ alkyl, and $R^1$ is selected from hydrogen, methyl, and $C_4$-$C_8$ alkyl.

In some embodiments, A is selected from:

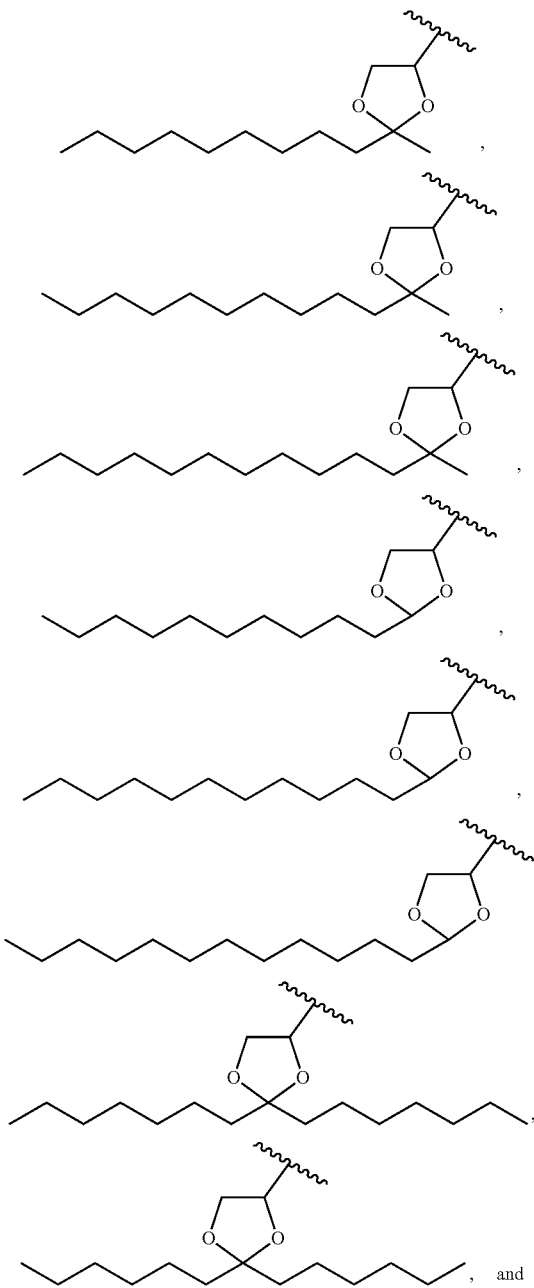

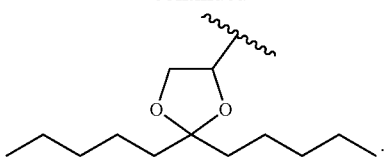

In some embodiments, A is:

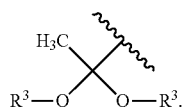

In some embodiments, each instance of $R^3$ is the same. In some embodiments, each $R^3$ is selected from $C_4$-$C_8$ alkyl and $C_4$-$C_8$ haloalkyl. In some embodiments, each $R^3$ is selected from $C_4$-$C_8$ alkyl. In some embodiments, each $R^3$ is selected from —$(CH_2)_x$—$(CF_2)_y$—$CF_3$, wherein x is 1, 2, 3, or 4, and y is 1, 2, 3, 4, 5, 6, or 7. For example, in some embodiments, x is 2 and y is 3 or 5.

In some embodiments, A is selected from:

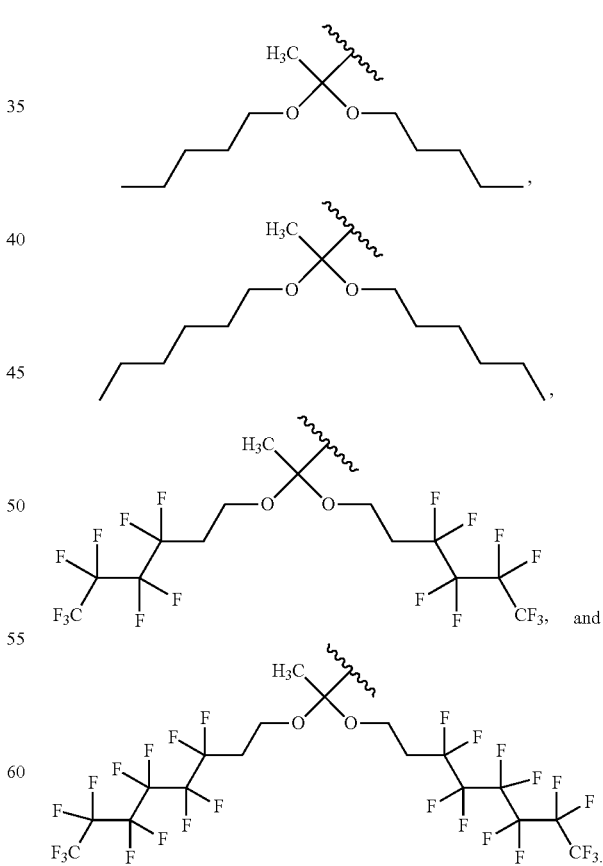

In some embodiments, m is 1. In some embodiments, $R^a$ and $R^b$ are each hydrogen.

In some embodiments, Q is selected from $C_1$-$C_6$-alkylene and $C_1$-$C_6$-hydroxyalkylene. In some embodiments, Q is selected from —$CH_2CH_2CH_2$— and —$CH_2CH(OH)CH_2$—. In some embodiments, Q is

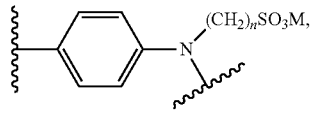

wherein n is 1, 2, 3, 4, 5, or 6.

In some embodiments, the group -Q-$SO_3M$ has formula:

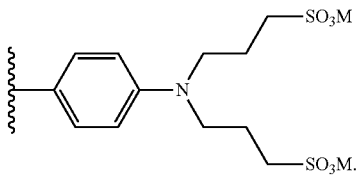

In some embodiments, each M is independently an alkali metal. In some embodiments, the alkali metal is sodium.

In some embodiments, the compound of formula (I) is selected from:

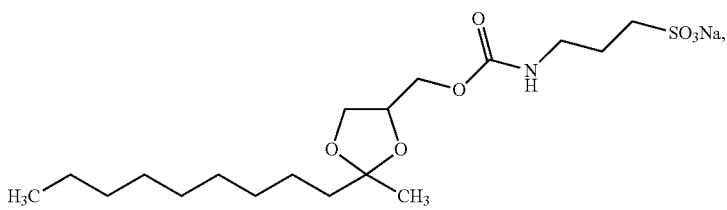

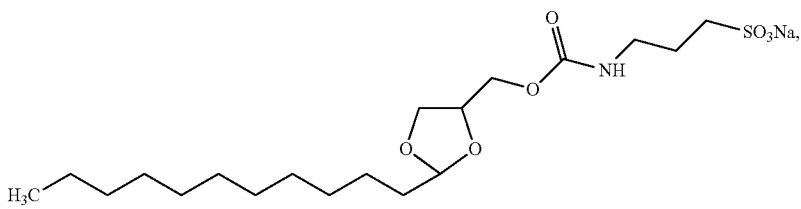

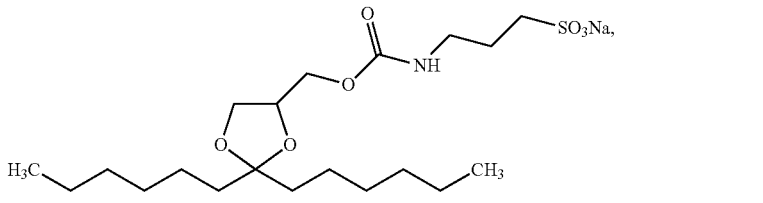

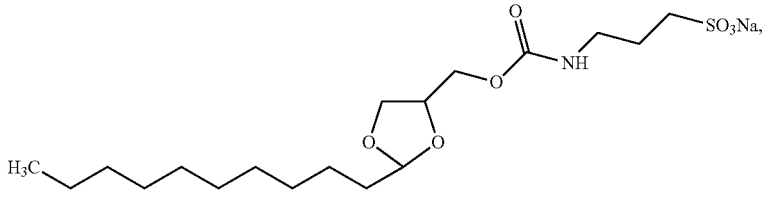

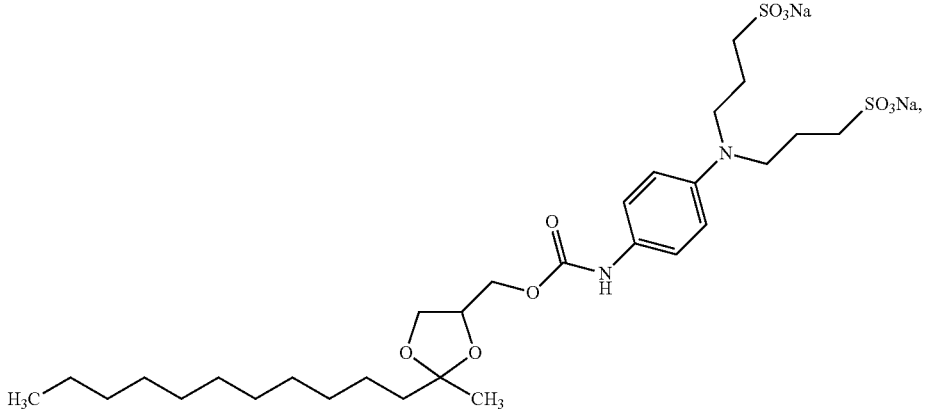

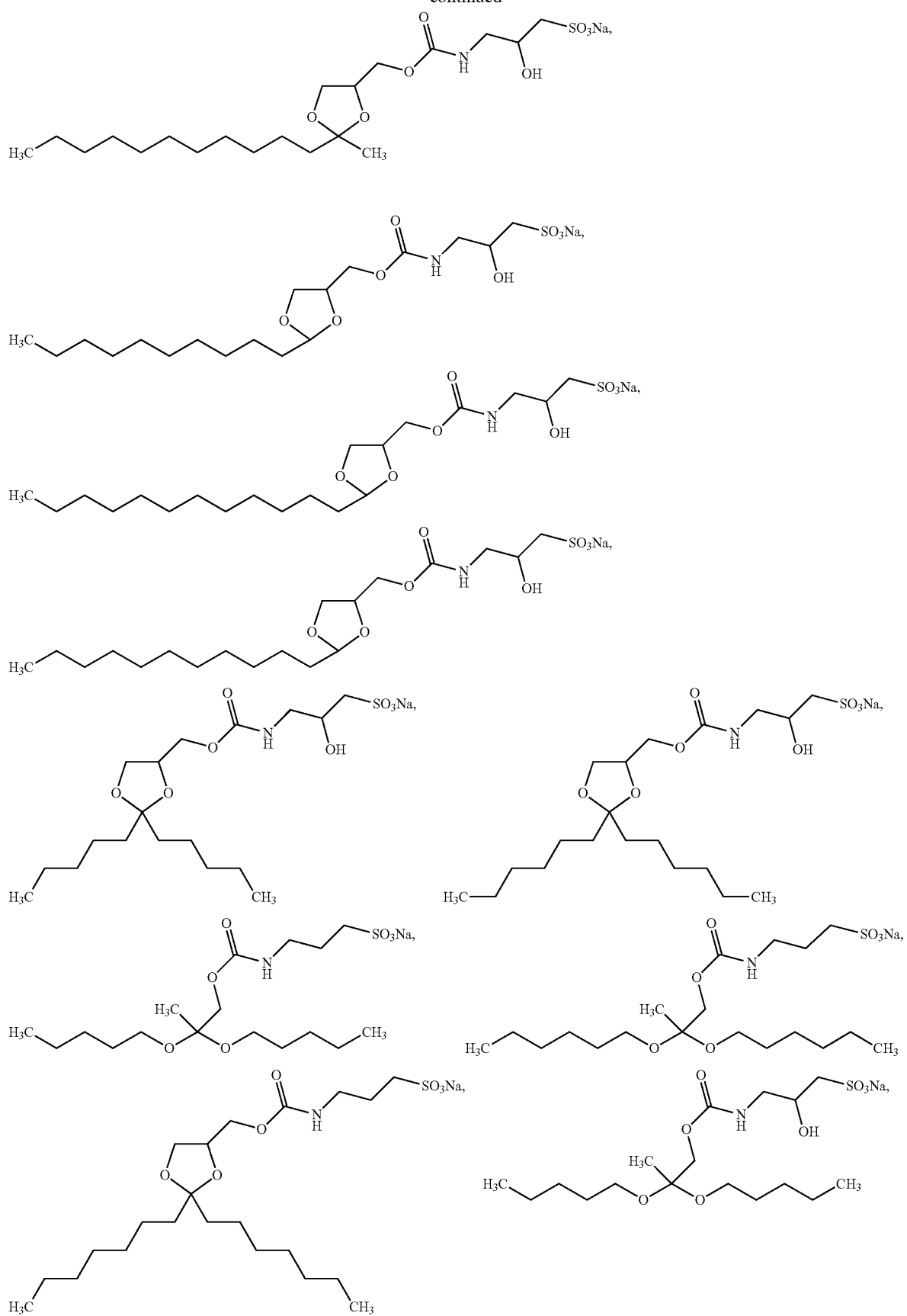

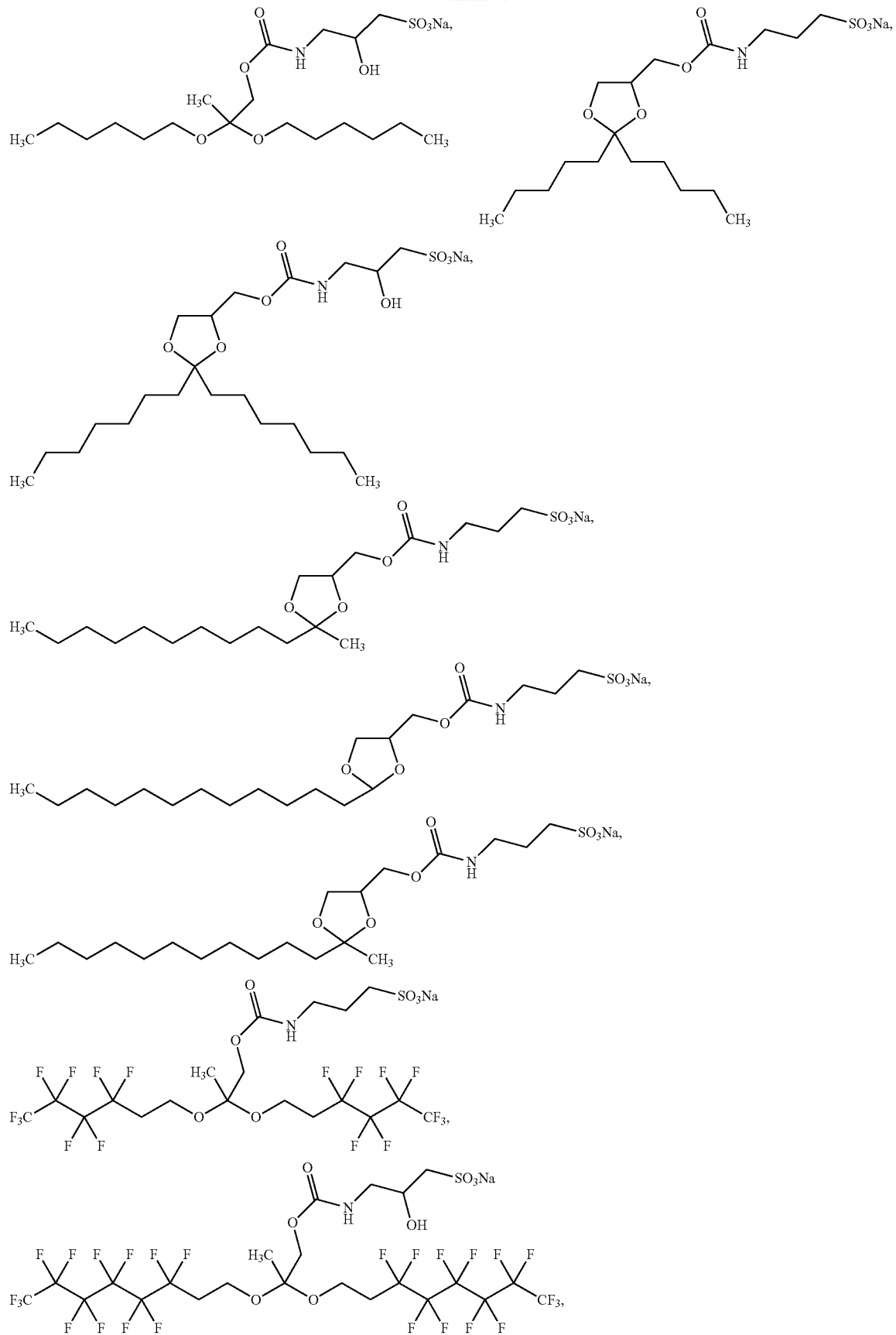

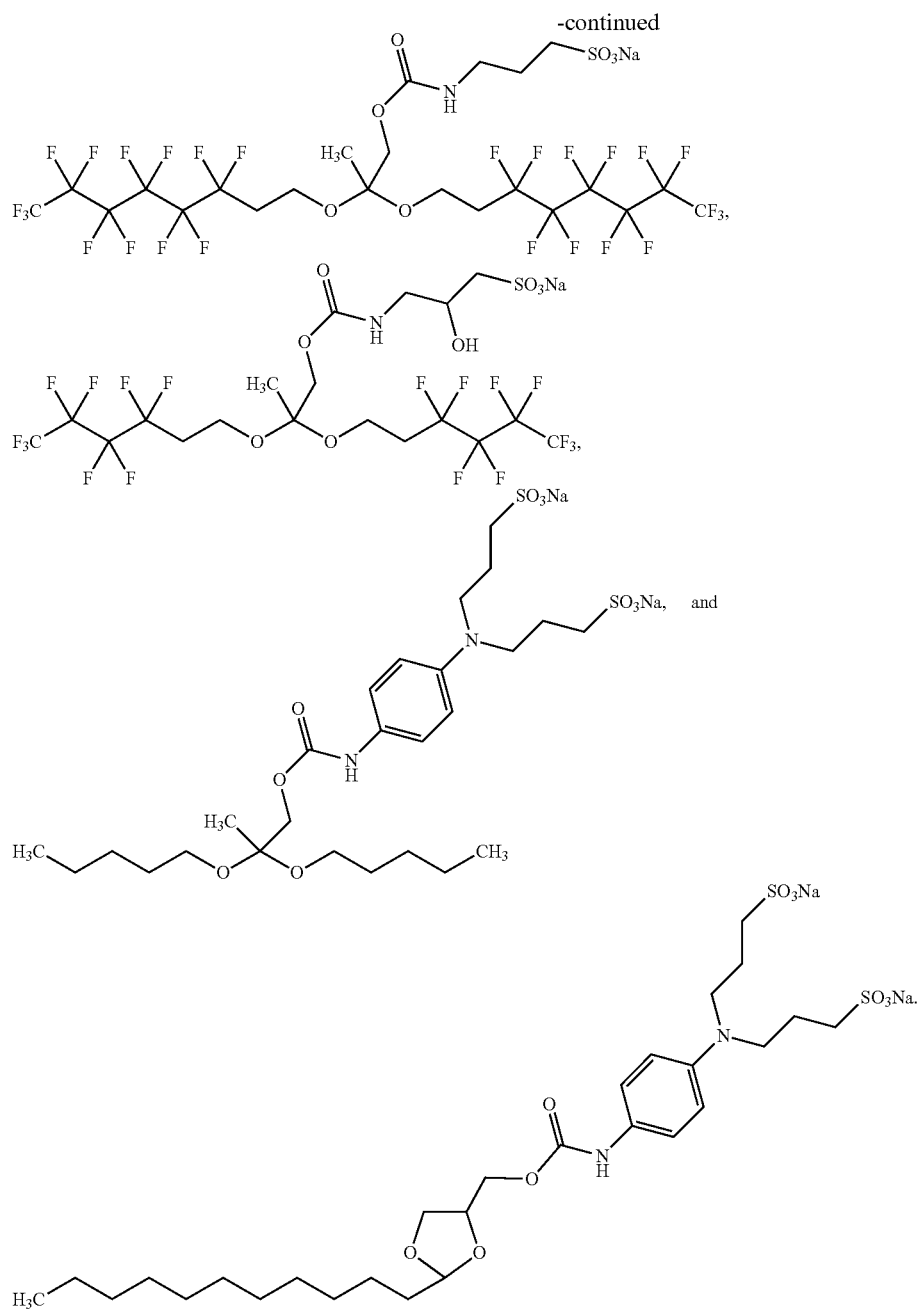

-continued

Embodiments of the present disclosure also include a method for digesting a protein, comprising:
- contacting a sample comprising at least one protein with a protein digestion reagent and a compound of formula (I), or a salt thereof,
- to thereby provide a sample comprising at least one digested protein.

In some embodiments, the sample is a gel, a solid support, or a solution. In some embodiments, the sample is a gel. In some embodiments, the sample is an aqueous solution. In some embodiments, the aqueous solution is a solution from an in-solution protein digestion with a protease, a protein pellet solubilization, a protein extract from cells, a protein extract from tissue, a protein deglycosylation with a deglycosidase, or a removal of non-specifically bound proteins from a protein-immobilizing support.

In some embodiments, the protein digestion reagent comprises a protease, cyanogen bromide, hydroxylamine, or any combination thereof.

In some embodiments, the protein digestion reagent comprises a protease. In some embodiments, the protease is a serine protease. In some embodiments, the serine protease is trypsin, chymotrypsin, or Lys-C.

In some embodiments, the method further comprises degrading the surfactant after the contacting step. In some embodiments, the degradation step comprises contacting the surfactant with an acid. In some embodiments, the surfactant self-decomposes after the contacting step.

In some embodiments, the method further comprises isolating at least one digested protein fragment. In some embodiments, the method further comprises analyzing at least one digested protein fragment. In some embodiments, the analyzing step comprises mass spectrometry, liquid chromatography, gel electrophoresis, or a combination thereof.

Embodiments of the present disclosure also include a composition comprising a gel and a compound of formula (I).

Embodiments of the present disclosure also include method for extracting a peptide from a gel, comprising:
contacting the gel with a compound of any one of claims 1-16 and an aqueous solution; and
separating the aqueous liquid from the gel, to thereby provide a solution comprising the peptide.

DETAILED DESCRIPTION

Figure 1:
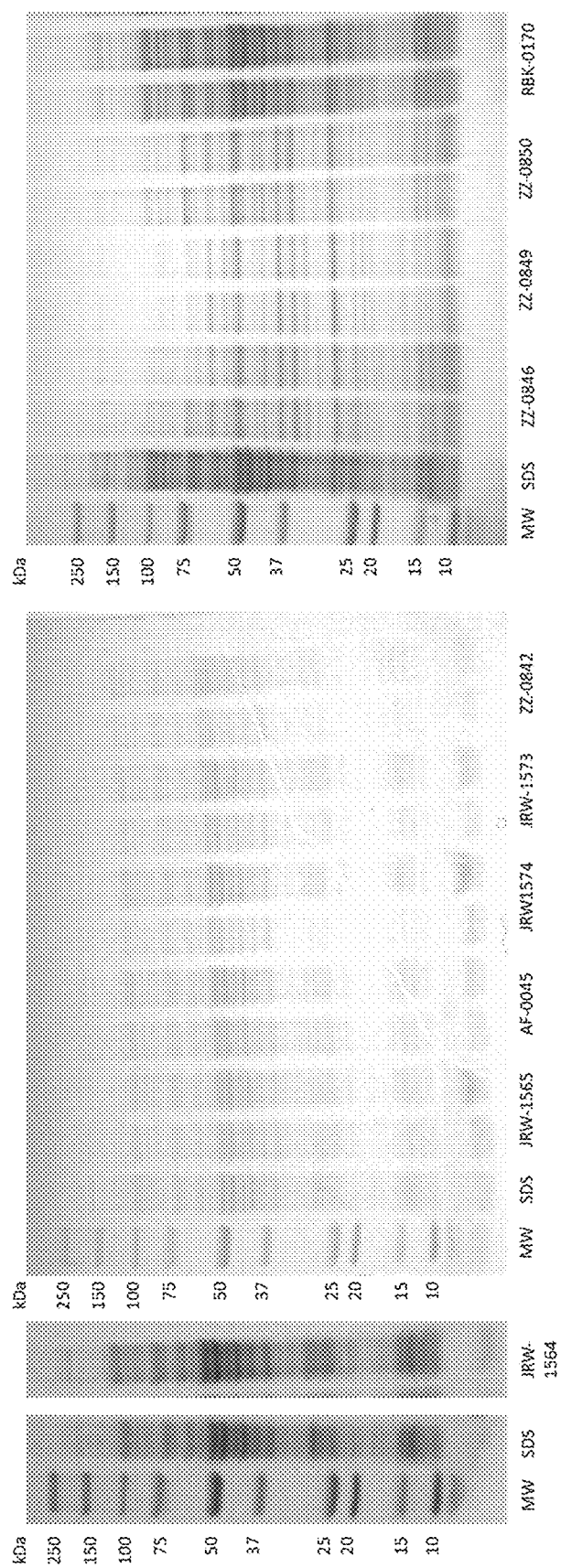
FIG. 1 shows representative SDS-PAGE gels of solubilized E. coli protein pellets following incubation with compounds described herein, as described in Example 31.

Provided herein are surfactant compounds that may have good water-solubility and aqueous stability even at higher temperatures, and which may degrade under acidic conditions. Such surfactants may be useful as protein solubilization and/or digestion reagents without interfering with proteases or with protein fragment mass spectrometry analysis.

Section headings as used in this section and the entire disclosure are merely for organizational purposes and are not intended to be limiting.

1. Definitions

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Sorrell, Organic Chemistry, 2$^{nd}$ edition, University Science Books, Sausalito, 2006; Smith, March's Advanced Organic Chemistry: Reactions, Mechanism, and Structure, 7$^{th}$ Edition, John Wiley & Sons, Inc., New York, 2013; Larock, Comprehensive Organic Transformations, 3rd Edition, John Wiley & Sons, Inc., New York, 2018; Carruthers, Some Modern Methods of Organic Synthesis, 3$^{rd}$ Edition, Cambridge University Press, Cambridge, 1987; the entire contents of each of which are incorporated herein by reference.

The term "alkyl", as used herein, means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl", as used herein, means a straight or branched hydrocarbon chain containing from 2 to 30 carbon atoms and at least one carbon-carbon double bond. For example, an alkenyl group may include 2 to 16 carbon atoms ($C_2$-$C_{16}$ alkenyl), 2 to 14 carbon atoms ($C_2$-$C_{14}$ alkenyl), 2 to 12 carbon atoms ($C_2$-$C_{12}$ alkenyl), 2 to 10 carbon atoms ($C_2$-$C_{10}$ alkenyl), 2 to 8 carbon atoms ($C_2$-$C_8$ alkenyl), 2 to 6 carbon atoms ($C_2$-$C_6$ alkenyl), or 2 to 4 carbon atoms ($C_2$-$C_4$ alkenyl). Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkylene", as used herein, refers to a divalent group derived from a straight or branched chain hydrocarbon of 1 to 10 carbon atoms ($C_1$-$C_{10}$ alkylene), for example, of 1 to 6 carbon atoms ($C_1$-$C_6$ alkylene). Representative examples of alkylene include, but are not limited to, —$CH_2$—, —$CH_2CH_2$—, —$CH(CH_3)$—, —$CH_2CH_2CH_2$—, —$CH_2CH(CH_3)$—, —$CH_2CH_2CH_2CH_2$—, —$CH_2CH(CH_3)CH_2$—, —$CH_2CH_2CH(CH_3)$—, —$CH_2CH_2CH_2CH_2CH_2$—, —$CH(CH_3)CH_2CH_2$—, —$CH(CH_3)CH_2CH_2$—, —$CH_2CH_2CH_2CH_2CH_2$—, —$CH_2CH_2CH(CH_3)CH_2CH_2$—, $CH_2CH(CH_3)CH_2CH_2CH_2$—, and —$CH(CH_3)CH_2CH_2CH_2CH_2$—.

The term "halogen" or "halo", as used herein, means F, $C_1$, Br, or I.

The term "haloalkyl", as used herein, means an alkyl group, as defined herein, in which one or more hydrogen atoms are replaced by a halogen. For example, one, two, three, four, five, six, seven or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, and 2,2,2-trifluoroethyl.

The term "hydroxy" or "hydroxyl", as used herein, means an —OH group.

The term "hydroxyalkyl", as used herein, refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

The term "hydroxyalkylene", as used herein, refers to an alkylene group, as defined herein, substituted with at least one hydroxy group. Representative examples of hydroxyalkylene include, but are not limited to, hydroxymethylene (—CH(OH)—), 2-hydroxyethylene (—CH$_2$—CH(OH)—), 2-hydroxypropylene (—CH$_2$—CH(OH)—CH$_2$—), and 3-hydroxypropylene (—CH$_2$—CH$_2$—CH(OH)—).

In some instances, the number of carbon atoms in a group (e.g., alkyl, haloalkyl, or cycloalkyl) is indicated by the prefix "$C_x$-$C_y$-", wherein x is the minimum and y is the maximum number of carbon atoms in the group. Thus, for example, "$C_1$-$C_3$-alkyl" refers to an alkyl group containing from 1 to 3 carbon atoms, and "$C_1$-$C_6$-haloalkyl" refers to a haloalkyl group containing form 1 to 6 carbon atoms.

The term "substituent" refers to a group substituted on an atom of the indicated group. When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl.

The terms "analysis" and "analyzing" refer to any of the various methods of solubilizing, separating, detecting, isolating, purifying, and/or characterizing molecules, such as, e.g., proteins, peptides, and fragments thereof. Examples include, but are not limited to, solid phase extraction; solid phase micro extraction; electrophoresis; mass spectrometry, e.g., Matrix Assisted Laser Desorption Ionization-Mass Spectrometry (MALDI-MS) or Electrospray Ionization Mass Spectrometry (ESI-MS); liquid chromatography, e.g., high performance, e.g., reverse phase, normal phase, or size exclusion chromatography; ion-pair liquid chromatography; liquid-liquid extraction, e.g., accelerated fluid extraction, supercritical fluid extraction, microwave-assisted extraction, membrane extraction, or Soxhlet extraction; precipitation; clarification; electrochemical detection; staining; elemental analysis; Edmund degradation; nuclear magnetic resonance; infrared analysis; flow injection analysis; capillary electrochromatography; ultraviolet detection; and combinations thereof.

The term "digestion" refers to a process of breaking down a molecule, for example a biomolecule, e.g., a protein, into simpler chemical compounds (fragments). Digestion is carried out using a digestion reagent, such as an enzyme, for example, a protease, or by a reaction with a chemical cleavage reagent. Digestion can result in breaking of amide bonds. In certain instances, the chemical can result in breaking specific amide bonds.

The term "sample", as used herein, refers to any specimen containing a protein that may be used in the methods of the disclosure. Examples include, without limitation, a protein extract from cells, a protein extract from tissue, a pellet containing proteins, a solution from a protein digestion with a protease, a solid support containing at least one protein, a gel containing a protein, or the like. A sample can include a crude or a purified, e.g., isolated or commercially obtained, sample. Further examples include, but are not limited to, inclusion bodies, biological fluids, biological tissues, biological matrices, embedded tissue samples, and cell culture supernatants.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The terms "comprise(s)", "include(s)", "having", "has", "can", "contain(s)", and "variants thereof", as used herein, are intended to be open-ended transitional phrases, terms, or words that do not preclude the possibility of additional acts or structures. The singular forms "a", "and", and "the" include plural references unless the context clearly dictates otherwise. Many embodiments herein are described using open "comprising" language. Such embodiments encompass multiple closed "consisting of" and/or "consisting essentially of" embodiments, which may alternatively be claimed or described using such language. The present disclosure also contemplates other embodiments "comprising", "consisting of", and "consisting essentially of", the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

Disclosed are compounds of formula (I):

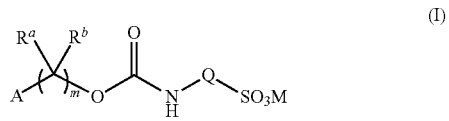

or a salt thereof, wherein:
A is selected from:

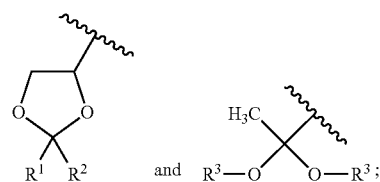

$R^1$ is selected from hydrogen, $C_1$-$C_{12}$ alkyl, $C_2$-$C_{12}$ alkenyl, and $C_1$-$C_{12}$ haloalkyl;
$R^2$ is selected from $C_4$-$C_{20}$ alkyl, $C_4$-$C_{20}$ alkenyl, $C_4$-$C_{20}$ haloalkyl;
each $R^3$ is independently selected from $C_1$-$C_{12}$ alkyl, $C_2$-$C_{12}$ alkenyl, and $C_1$-$C_{12}$ haloalkyl;
m is 1, 2, or 3;
$R^a$ and $R^b$, at each occurrence, are independently selected from hydrogen and $C_1$-$C_3$ alkyl;

Q is selected from $C_1$-$C_6$-alkylene, $C_1$-$C_6$-hydroxyalkylene, and a group of formula:

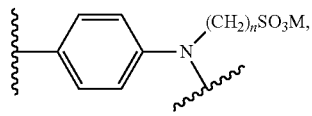

wherein n is 1, 2, 3, 4, 5, or 6; and
each M is independently selected from hydrogen, an alkali metal cation, and $NR_4^+$, wherein each R is independently selected from hydrogen and $C_1$-$C_{12}$ alkyl.

In some embodiments, A is:

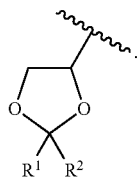

In some embodiments, $R^1$ is $C_1$-$C_{12}$ alkyl. In some embodiments, $R^1$ is $C_5$-alkyl. In some embodiments, $R^1$ is $C_6$-alkyl. In some embodiments, $R^1$ is $C_7$-alkyl. In some embodiments, $R^1$ is $C_8$-alkyl. In some embodiments, $R^1$ is $C_9$-alkyl. In some embodiments, $R^1$ is $C_{10}$-alkyl. In some embodiments, $R^1$ is $C_{11}$-alkyl. In some embodiments, $R^1$ is $C_{12}$-alkyl.

In some embodiments, $R^1$ is selected from hydrogen, methyl, and $C_4$-$C_8$ alkyl. In some embodiments, $R^1$ is hydrogen. In some embodiments, $R^1$ is methyl. In some embodiments, $R^2$ is $C_4$-$C_8$ alkyl. In some embodiments, $R^2$ is $C_5$-alkyl. In some embodiments, $R^2$ is $C_6$-alkyl. In some embodiments, $R^2$ is $C_7$-alkyl.

In some embodiments, $R^2$ is $C_6$-$C_{12}$ alkyl, and $R^1$ is selected from hydrogen, methyl, and $C_4$-$C_8$ alkyl. In some embodiments, $R^2$ is $C_6$-$C_{12}$ alkyl, and $R^1$ is hydrogen. In some embodiments, $R^2$ is $C_6$-$C_{12}$ alkyl, and $R^1$ is methyl. In some embodiments, $R^2$ is $C_6$-$C_{12}$ alkyl, and $R^1$ is $C_4$-$C_8$ alkyl.

In some embodiments, A is selected from:

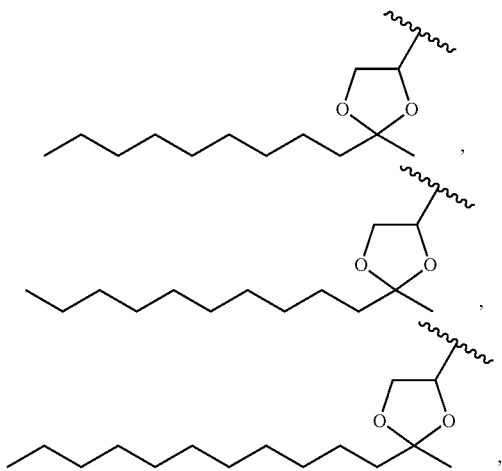

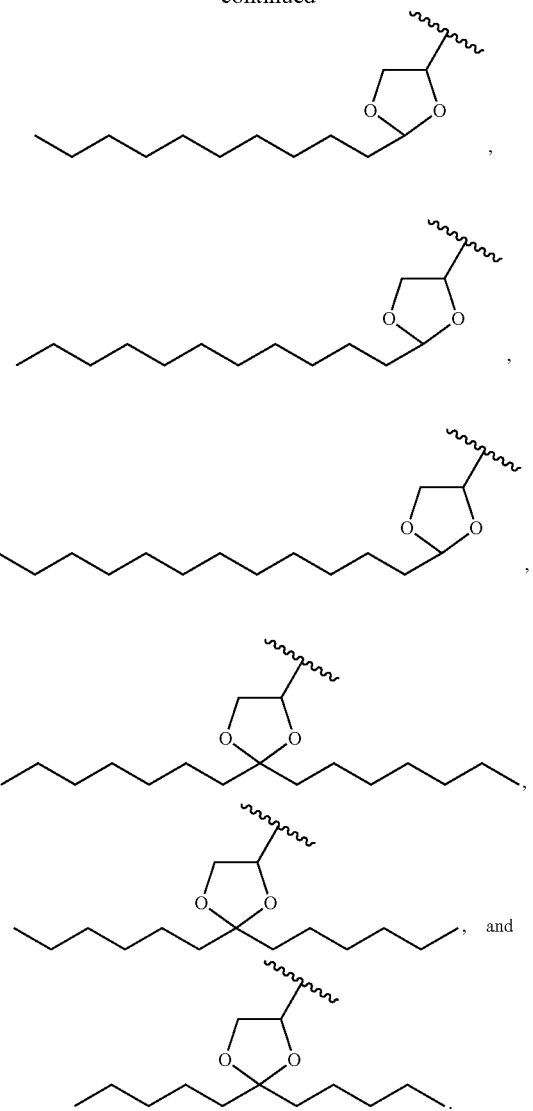

In some embodiments, A is:

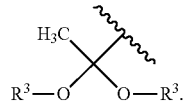

In some embodiments, each instance of $R^3$ is the same. In some embodiments, each $R^3$ is selected from $C_1$-$C_{12}$ alkyl and $C_1$-$C_{12}$ haloalkyl. In some embodiments, each $R^3$ is selected from $C_4$-$C_8$ alkyl and $C_4$-$C_8$ haloalkyl. In some embodiments, each $R^3$ is $C_1$-$C_{12}$ alkyl. In some embodiments, each $R^3$ is $C_4$-$C_8$ alkyl. In some embodiments, each $R^3$ is $C_5$-alkyl. In some embodiments, each $R^3$ is $C_6$-alkyl. In some embodiments, each $R^3$ is $C_1$-$C_{12}$ haloalkyl. In some embodiments, each $R^3$ is $C_4$-$C_8$ haloalkyl. In some embodiments, each $R^3$ is —$(CH_2)_x$—$(CF_2)_y$—$CF_3$, wherein x is 1, 2, 3, or 4, and y is 1, 2, 3, 4, 5, 6, or 7. For example, in some embodiments, x is 2 and y is 3 or 5. In some embodiments, x is 2 and y is 3. In some embodiments, x is 2 and y is 5.

In some embodiments, A is selected from:

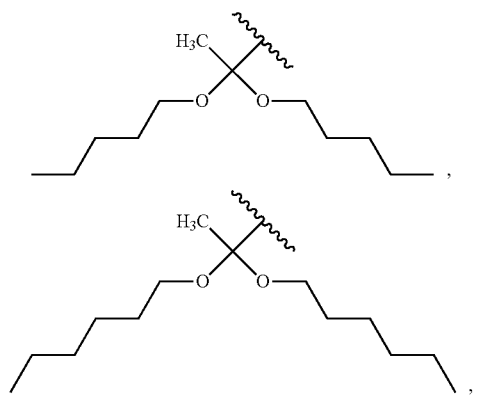,

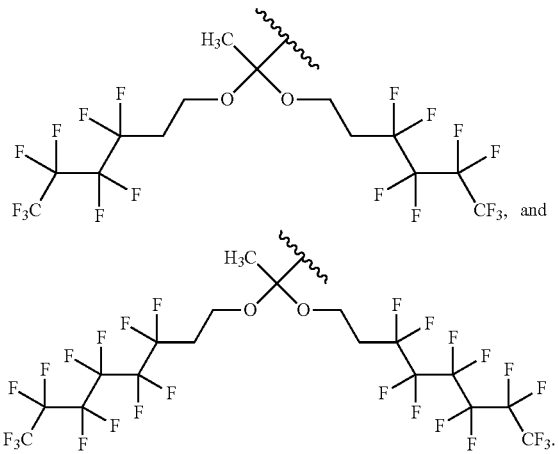,

In some embodiments, m is 1. In some embodiments, m is 2. In some embodiments, m is 3. In some embodiments, $R^a$ and $R^b$ at each occurrence are independently selected from hydrogen and methyl. In some embodiments, $R^a$ and $R^b$ at each occurrence are hydrogen. In some embodiments, m is 1 and $R^a$ and $R^b$ are each hydrogen.

In some embodiments, Q is selected from $C_1$-$C_6$-alkylene and $C_1$-$C_6$-hydroxyalkylene. In some embodiments, Q is selected from —CH$_2$CH$_2$CH$_2$— and —CH$_2$CH(OH)CH$_2$—. In some embodiments, Q is —CH$_2$CH$_2$CH$_2$—. In some embodiments, Q is —CH$_2$CH(OH)CH$_2$—.

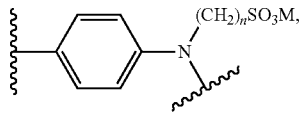

In some embodiments, Q is wherein n is 1, 2, 3, 4, 5, or 6.

In some embodiments, the group -Q-SO$_3$M has formula:

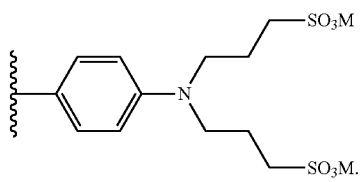

In some embodiments, each M is independently an alkali metal. In some embodiments, the alkali metal is sodium.

In some embodiments, the compound of formula (I) is selected from:

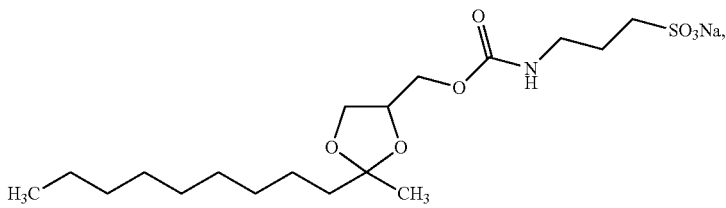

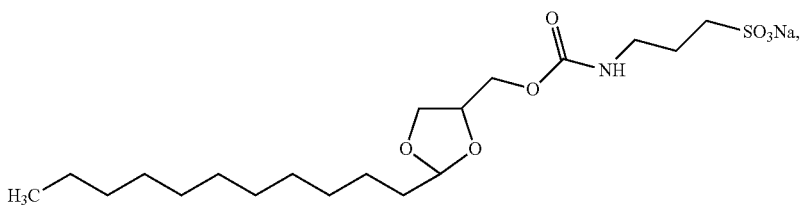

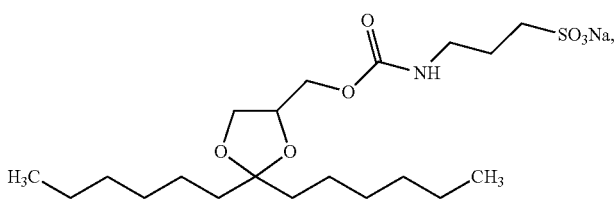

-continued
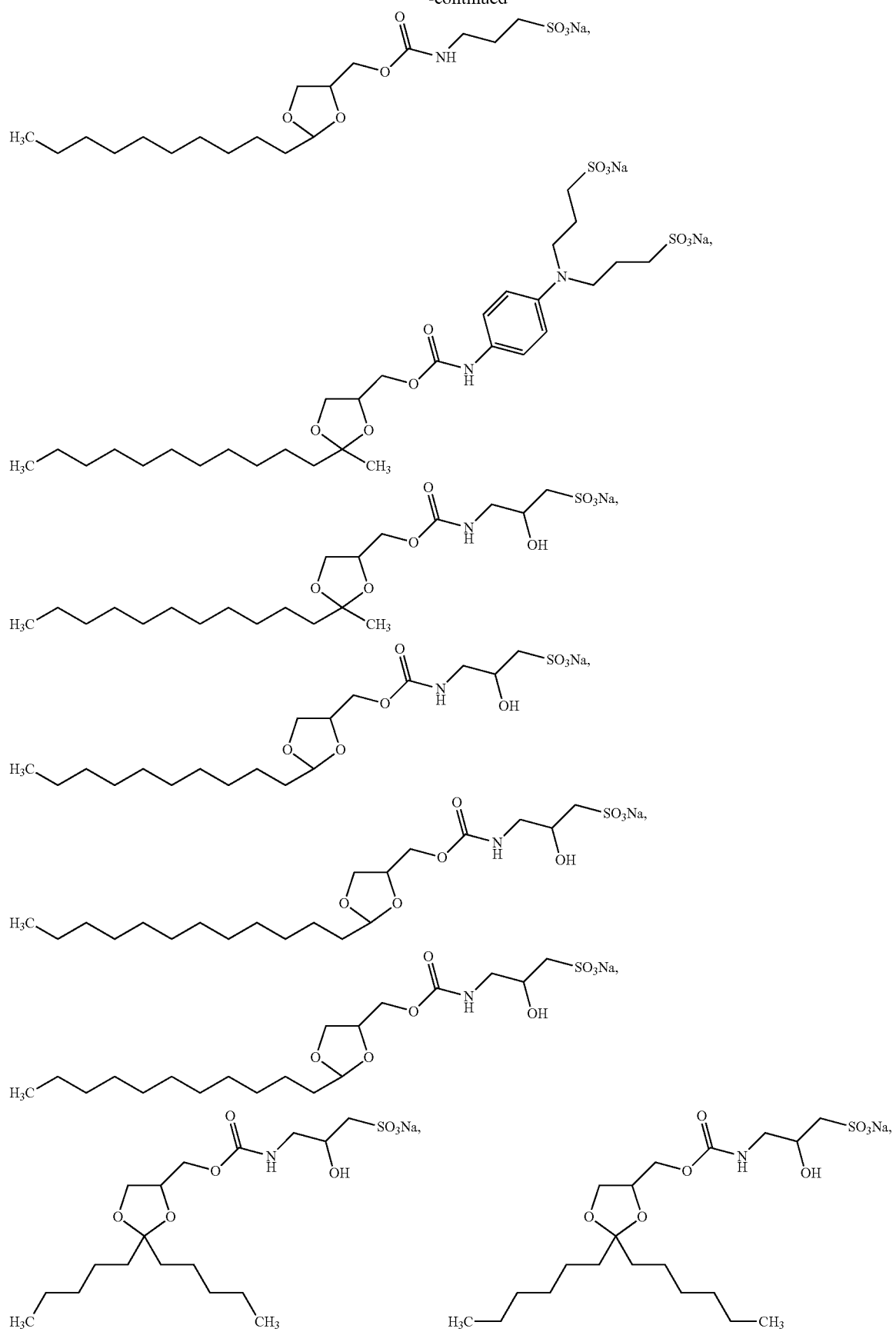

23
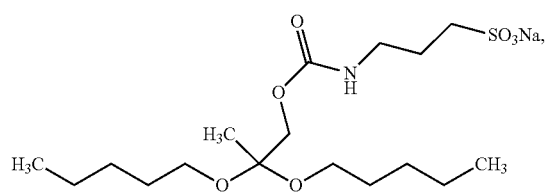
24
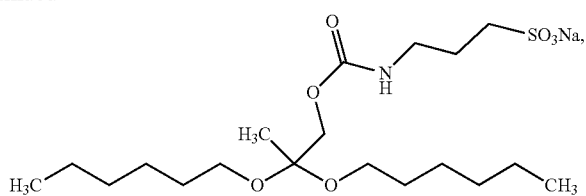
-continued
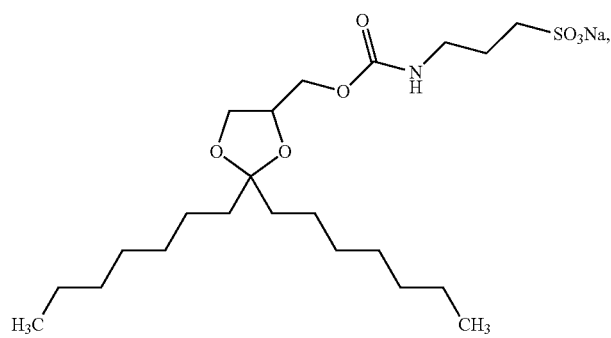
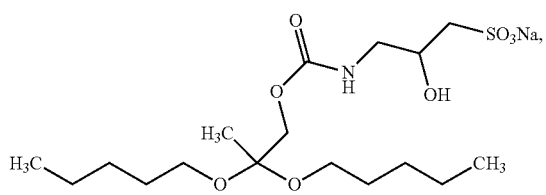
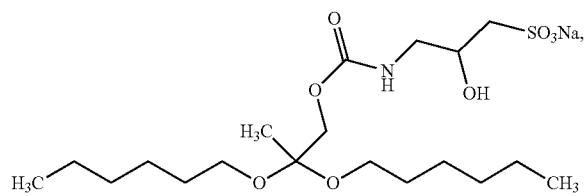
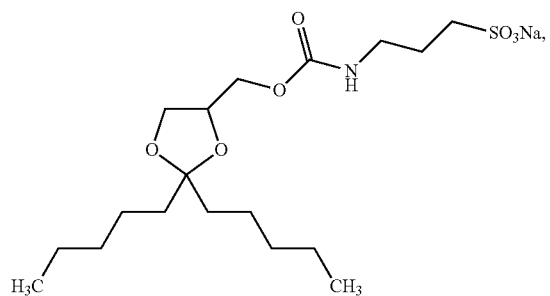
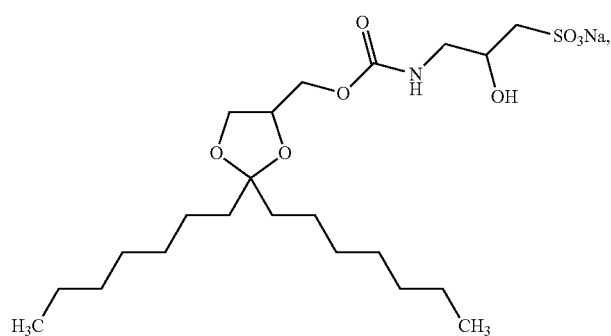
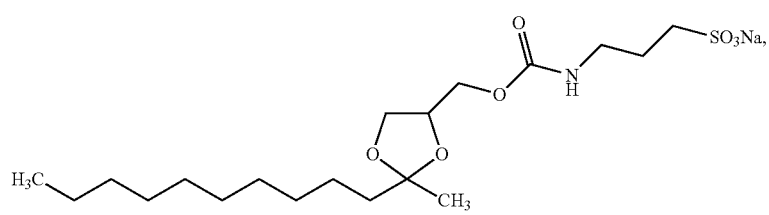
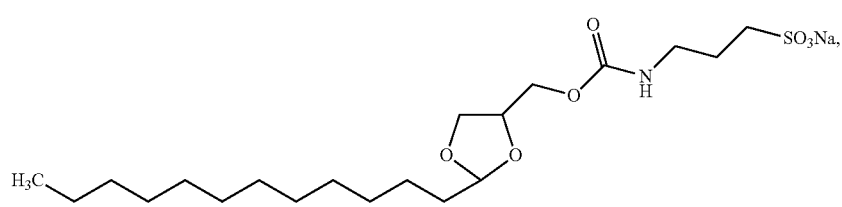

-continued
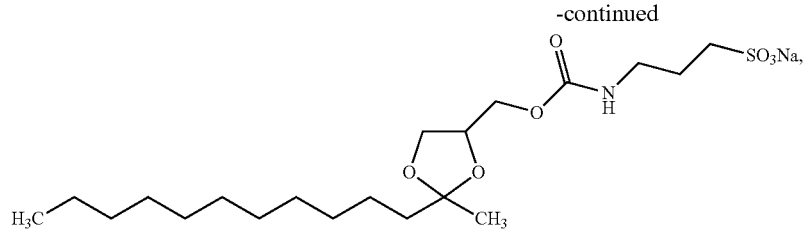
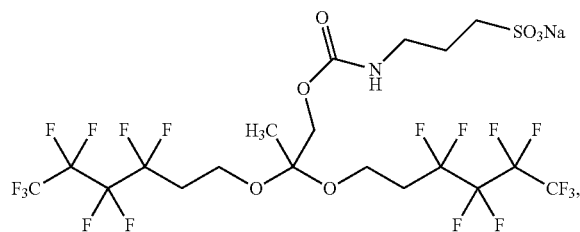
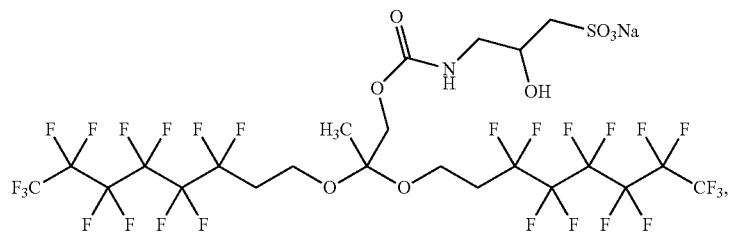
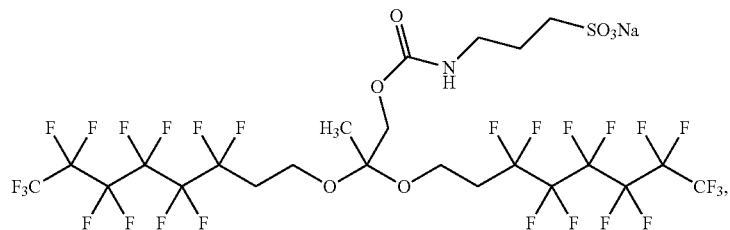
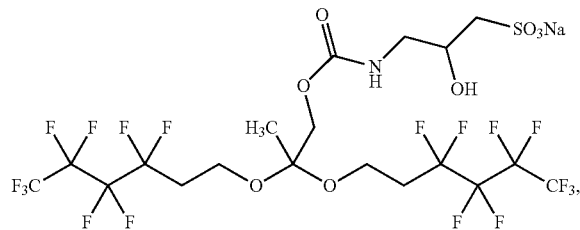
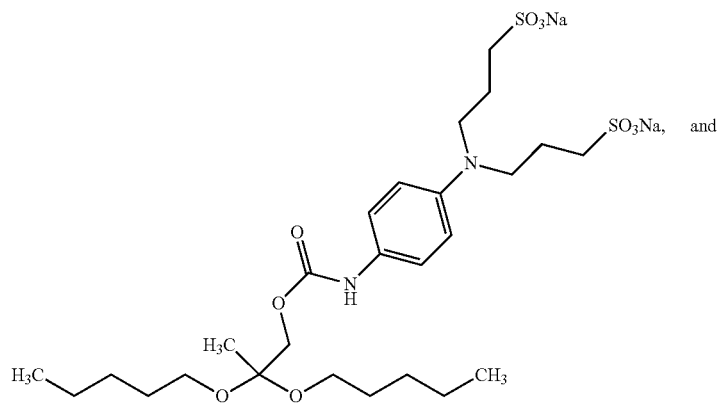

-continued

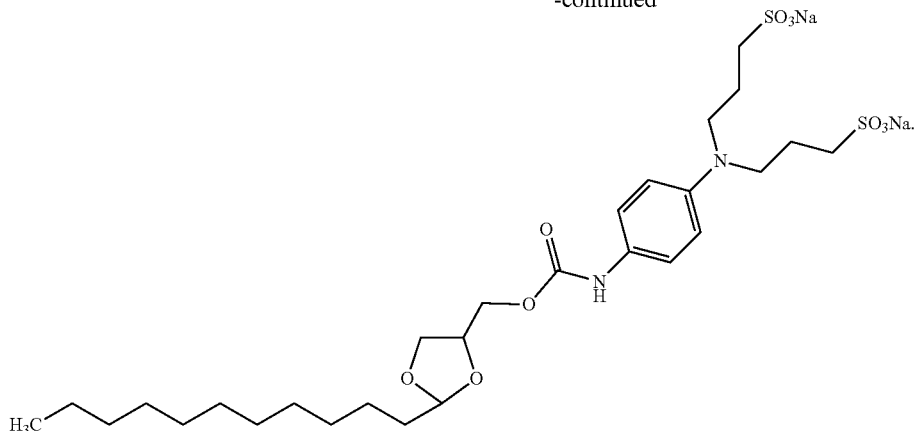

A compound described herein, such as a compound of formula (I), can be in the form of a salt. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

For example, if the compound is anionic, or has a functional group which may be anionic (e.g., —COOH may be —COO$^-$, —SO$_3$H may be —SO$_3^{-1}$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic, and valeric.

Unless otherwise specified, a reference to a particular compound of formula (I) herein also includes salt forms thereof.

Certain compounds of formula (I) may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In some embodiments, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In some embodiments, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In some embodiments, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation", as used herein, is enriched for a selected stereoconfiguration of one, two, three, or more selected stereocenters within the subject compound. Exemplary selected stereocenters and exemplary stereoconfigurations thereof can be selected from those provided herein, e.g., in an example described herein. "Enriched" is meant at least 60%, e.g., of the molecules of compound in the preparation have a selected stereochemistry of a selected stereocenter. In an embodiment, it is at least 65%, 70%, 75%, 80%, 85%, 90%, 95%, 96%, 97%, 98%, or 99%. "Enriched" refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers", as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may include structurally isomeric forms falling within that class (e.g., C$_3$-alkyl or propyl includes n-propyl and iso-propyl; C$_4$-alkyl or butyl includes n-, iso-, sec-, and tert-butyl; and methoxyphenyl includes ortho-, meta-, and para-methoxyphenyl). The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

The compounds be prepared by a variety of methods. For example, compounds can be prepared as shown in Schemes 1-3. Abbreviations used in the schemes include the following: ACN is acetonitrile; DIPEA is N,N-diisopropylethylamine; DMF is N,N-dimethylformamide; TFA is trifluoroacetic acid; THF is tetrahydrofuran; rt is room temperature; and TsOH is p-toluenesulfonic acid.

Scheme 1. Exemplary Compound Synthesis

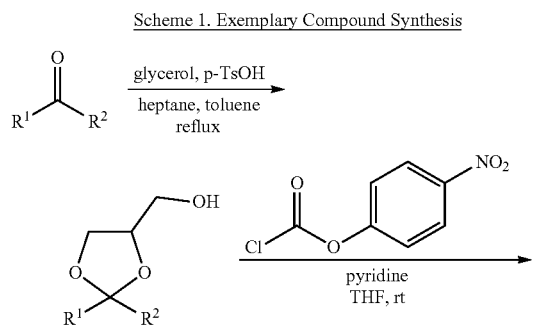

Scheme 2. Exemplary Compound Synthesis

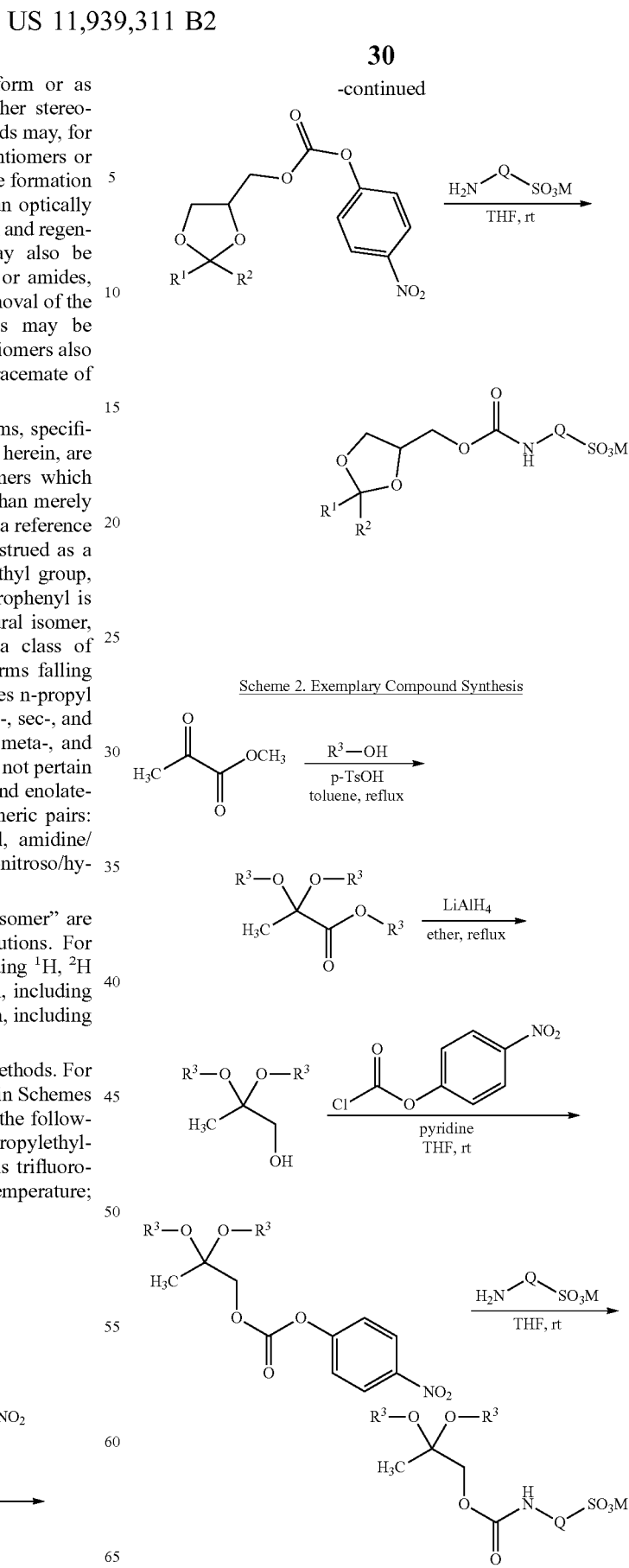

Scheme 3. Exemplary Compound Synthesis

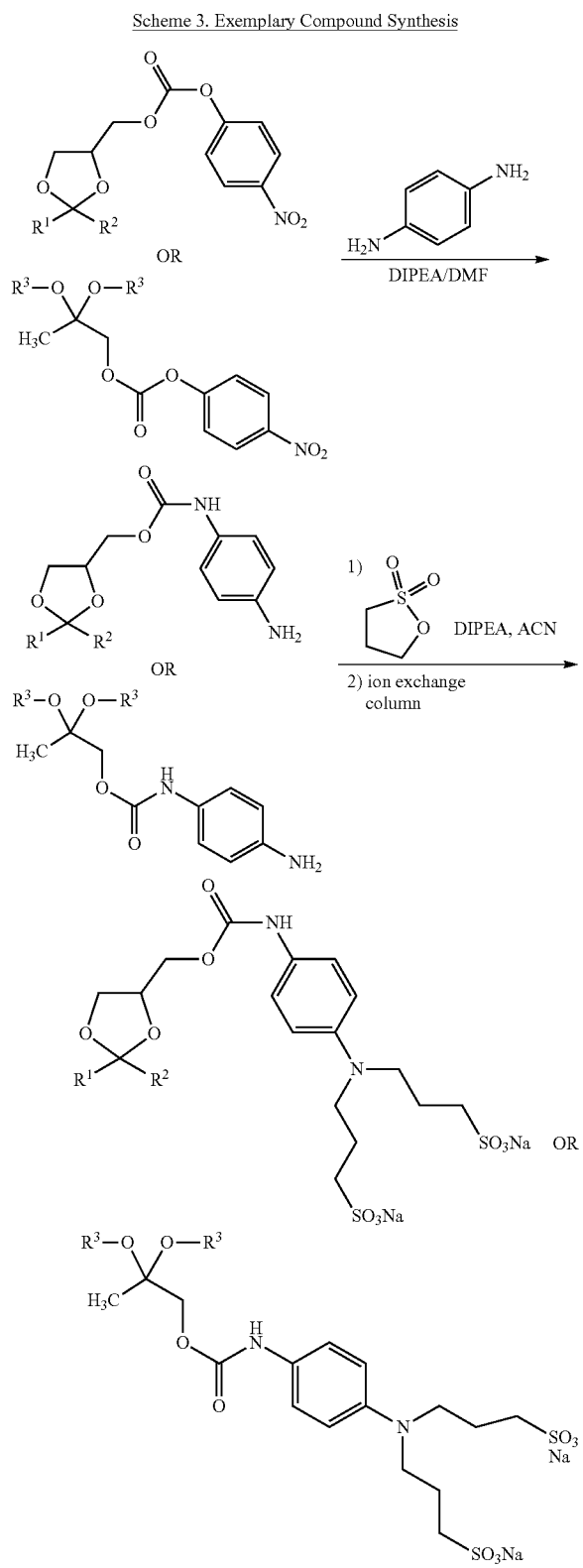

The compounds and intermediates herein may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in the treatise by PGM Wuts entitled "Greene's Protective Groups in Organic Synthesis" (5th ed.), John Wiley & Sons, Inc. (2014), which is incorporated herein by reference in its entirety. Synthesis of the compounds of the invention can be accomplished by methods analogous to those described in the synthetic schemes described hereinabove and in specific examples.

The synthetic schemes and specific examples as described are illustrative and are not to be read as limiting the scope of the invention as it is defined in the claims. All alternatives, modifications, and equivalents of the synthetic methods and specific examples are included within the scope of the claims.

3. Methods

Embodiments of the present disclosure include methods for digesting proteins. Use of a compound of formula (I) in such methods may facilitate protein digestion, for example, by solubilizing hydrophobic or other insoluble compounds, and/or aiding in protein unfolding, to improve protein digestion. The compounds of formula (I) may also aid in recovery of generated protein fragments by improving extractions from gels, and/or by preventing protein fragment loss due to absorption or precipitation. For example, compounds of formula (I) can be easily degraded during or after protein digestion, and the fragments may be readily removed from the sample or may not materially interfere with any subsequent analysis steps.

The methods comprise a step of contacting a sample comprising at least one protein with a protein digestion reagent and a compound of formula (I), or a salt thereof, to thereby provide a sample comprising at least one digested protein.

The methods include use of a protein digestion reagent. The protein digestion reagent cleaves peptide bonds within the protein to produce smaller peptide fragments. The protein digestion reagent may comprise a protease. In some embodiments, the protease may be a serine protease such as trypsin, chymotrypsin, Lys-C, Glu-C, elastase, or proteinase K. In some embodiments, the protease may be a zinc metalloprotease such as Lys-N or Asp-N. In some embodiments, the protease may be a cysteine protease such as papain or Arg-C. In some embodiments, the protease may be an aspartic protease such as pepsin. The protease may be specific or non-specific. In some embodiments, the protein digestion reagent is a non-enzymatic digestion reagent such as cyanogen bromide or hydroxylamine. Any suitable combination of protein digestion reagents may also be used. In some embodiments, the protein digestion reagent is trypsin.

The methods also include use of a compound of formula (I). Without wishing to be limited by theory, the compounds of formula (I) may aid protein digestion by solubilizing and/or denaturing the proteins to be digested. For example, the compounds may facilitate protein unfolding to provide the digestion reagent access to internal protein sites.

The methods can be used with a variety of protein samples. In some embodiments, the sample is a gel, a solid support, or a solution. In some embodiments, the sample is a gel. In some embodiments, the sample is an aqueous solution. In some embodiments, the aqueous solution is a solution from an in-solution protein digestion with a protease, a protein pellet solubilization, a protein extract from cells, a protein extract from tissue, a protein deglycosylation with a deglycosidase, or a removal of non-specifically bound proteins from a protein-immobilizing support.

In some embodiments, the method further comprises degrading the surfactant after the contacting step. In some embodiments, the degradation step comprises contacting the surfactant with an acid. For example, addition of an acid may degrade the compound into polar and lipophilic components, where the lipophilic component may be removed from the sample prior to analysis (e.g., by passing the sample through a silica plug, such as a C18 derivatized silica plug). Any suitable acid can be used, including inorganic acids (e.g., hydrochloric, hydrobromic, hydroiodic, sulfuric, sulfurous, nitric, nitrous, phosphoric, or phosphorous acids), or organic acids (e.g., 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic, and valeric.

In some embodiments, the surfactant self-decomposes after the contacting step. In other words, in certain embodiments, the surfactant may decompose on its own during the course of the method, with no added reagents or other stimulus to initiate the decomposition.

In some embodiments, the method further comprises isolating at least one digested protein fragment. The digested protein can be isolated from the sample according to established techniques, such as extraction from a gel, chromatographic separation, centrifugation, precipitation, affinity purification, and the like.

For example, a protein fragment (e.g., a peptide) can be extracted from a gel by contacting the gel with a compound of formula (I) and an aqueous solution, and subsequently separating the aqueous liquid from the gel to provide a solution comprising the protein fragment.

In some embodiments, the method further comprises analyzing at least one digested protein fragment or peptide. In some embodiments, the analyzing step comprises mass spectrometry, liquid chromatography (e.g., high performance liquid chromatography, reverse phase chromatography, normal phase chromatography, size exclusion chromatography, or the like), gel electrophoresis (e.g., sodium dodecyl sulfate-polyacrylamide gel electrophoresis (SDS-PAGE), or native polyacrylamide gel electrophoresis (native PAGE)), or any combination thereof.

Embodiments of the present disclosure also include a composition comprising a gel and a compound of formula (I).

4. EXAMPLES

It will be apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

In the Examples, the following abbreviations are used: ACN is acetonitrile; DCM is dichloromethane; DIPEA is N,N-diisopropylethylamine; DMF is N,N-dimethylformamide; DMSO is dimethylsulfoxide; RT is room temperature; THF is tetrahydrofuran; and p-TsOH is p-toluenesulfonic acid.

Example 1

Sodium 3-((((2-methyl-2-nonyl-1,3-dioxolan-4-yl)methoxy)carbonyl)amino)propane-1-sulfonate (WZ-0547)

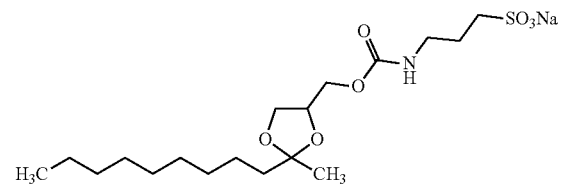

Step 1. (2-methyl-2-nonyl-1,3-dioxolan-4-yl)methanol (WZ-0540)

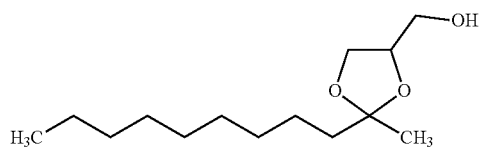 [SMILES: CCCCCCCCCC1(C)OCC(CO)O1]

To a solution of undecan-2-one (20.0 g, 117 mmol) in heptane and toluene (1:2, 300 mL), glycerol (13.0 g, 141 mmol) and p-toluenesulfonic acid (404 mg, 2.35 mmol) was added. The mixture was heated to reflux using a Dean Stark trap condenser for 18 h. The reaction was neutralized with NaHCO$_3$ (0.04 eq) in water (100 mL). The organic layer was washed with more water. The organic layer was dried with sodium sulfate, filtered, concentrated, and purified with silica gel chromatography to afford desired product (18.1 g, 63%) as a colorless oil. ESI MS m/z 245 [M+H]+.

Step 2. (2-methyl-2-nonyl-1,3-dioxolan-4-yl)methyl (4-nitrophenyl) carbonate (WZ-0546)

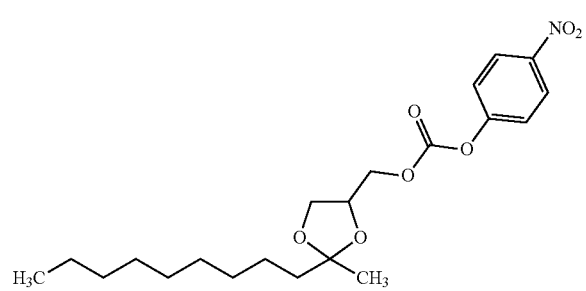 [SMILES: CCCCCCCCCC1(C)OCC(COC(=O)Oc2ccc([N+](=O)[O-])cc2)O1]

To a solution of (2-methyl-2-nonyl-1,3-dioxolan-4-yl)methanol (5.0 g, 20.5 mmol) in THF (50 mL) at 0° C., 4-nitrophenyl carbonochloridate (6.2 g, 30.7 mmol) and pyridine (4.9 g, 61.4 mmol) was added. The suspension stirred for 2 h at 0° C. The reaction was concentrated under vacuum, suspended in heptanes, filtered, and the solid was washed with heptane. The filtrate was concentrated and purified with silica gel chromatography to afford desired product (7.8 g, 93%) as a colorless oil. MS m/z 410 [M+H]+.

Step 3. Sodium 3-((((2-methyl-2-nonyl-1,3-dioxolan-4-yl)methoxy)carbonyl)amino)propane-1-sulfonate (WZ-0547)

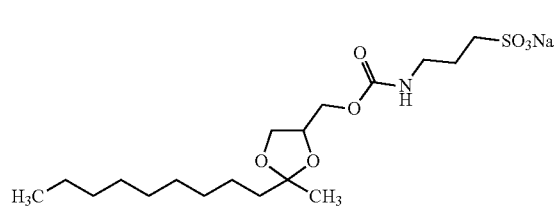

To a solution of (2-methyl-2-nonyl-1,3-dioxolan-4-yl)methyl (4-nitrophenyl) carbonate (0.60 g, 1.5 mmol) in THF (30 mL), 3-aminopropane-1-sulfonic acid tetrabutylammonium (0.67 g, 1.8 mmol) was added. The mixture stirred for 30 min at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.094 g, 10%) as a white solid. $^1$H NMR (400 MHz, DMSO-d$_6$) δ 7.25 (t, J=5.8 Hz, 1H), 4.21-4.11 (m, 1H), 4.07-3.96 (m, 2H), 3.90 (dd, J=11.4, 6.2 Hz, 1H), 3.69-3.58 (m, 1H), 3.02 (q, J=6.7 Hz, 2H), 2.45-2.32 (m, 2H), 1.75-1.63 (m, 2H), 1.57-1.47 (m, 2H), 1.35-1.18 (m, 14H), 0.91-0.79 (m, 3H); MS m/z 408 [M−H−Na]−.

Example 2

Sodium 3-((((2,2-dihexyl-1,3-dioxolan-4-yl)methoxy)carbonyl)amino)propane-1-sulfonate (TU-1179)

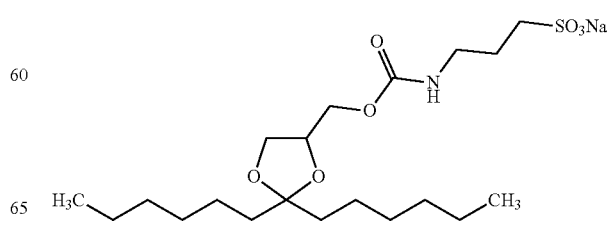

Step 1. (2,2-dihexyl-1,3-dioxolan-4-yl)methanol (TU-1172)

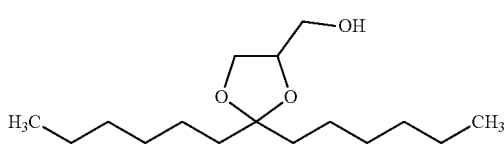 [SMILES: CCCCCCC1(CCCCCC)OCC(CO)O1]

To a solution of tridecan-7-one (11.5 g, 58.0 mmol) in heptane and toluene (1:2, 150 mL), glycerol (6.5 g, 70.6 mmol) and p-toluenesulfonic acid (230 mg, 1.2 mmol) was added. The mixture was heated to reflux using a Dean Stark trap condenser for 18 h. The reaction was neutralized with NaHCO$_3$ (0.04 eq) in water (100 mL) and extracted with ethyl acetate. The organic layer was dried with sodium sulfate, filtered, concentrated, and purified with silica gel chromatography to afford desired product (9.4 g, 59%) as a colorless oil. MS m/z 273 [M+H]+.

Step 2. (2,2-dihexyl-1,3-dioxolan-4-yl)methyl (4-nitrophenyl) carbonate (TU-1175)

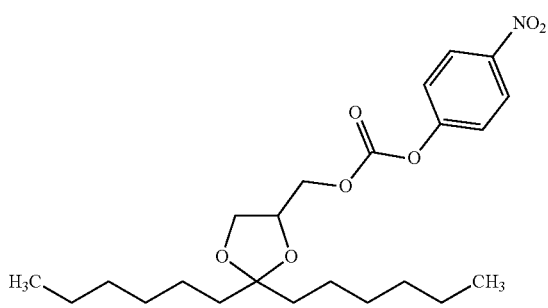 [SMILES: CCCCCCC1(CCCCCC)OCC(COC(=O)Oc2ccc([N+](=O)[O-])cc2)O1]

To a solution of (2,2-dihexyl-1,3-dioxolan-4-yl)methanol (6.1 g, 22.3 mmol) in THF (100 mL) at 0° C., 4-nitrophenyl carbonochloridate (6.8 g, 33.6 mmol) and pyridine (5.3 g, 67.0 mmol) was added. The suspension stirred for at 0° C. for 4 h. The reaction was concentrated under vacuum, dissolved in DCM, concentrated with celite, and purified with silica gel chromatography to afford desired product (9.5 g, 97%) as a light yellow oil.

Step 3. Sodium 3-((((2,2-dihexyl-1,3-di oxolan-4-yl)methoxy)carbonyl)amino)propane-1-sulfonate (TU-1179)

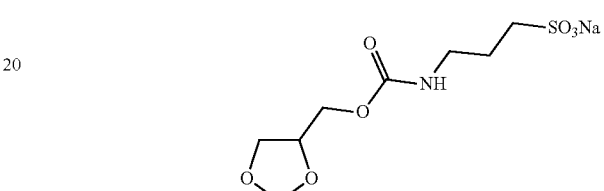

To a solution of (2,2-dihexyl-1,3-dioxolan-4-yl)methyl (4-nitrophenyl) carbonate (1.47 g, 3.36 mmol) in THF (40 mL), 3-aminopropane-1-sulfonic acid tetrabutylammonium (3.08 g, 8.11 mmol) was added. The mixture stirred for 3 hr at RT. The reaction was concentrated under vacuum and purified with silica gel chromatography using DCM/MeOH to afford the product as the tetrabutylammonium salt. The tetrabutylammonium product was dissolved in water and methanol (10:1, 10 mL), passed through a bissodium ion exchange resin, and lyophilized to afford desired product (1.39 g, 90%) as a white solid. $^1$H NMR (400 MHz, Deuterium Oxide) δ 4.37-4.16 (m, 1H), 4.12-3.91 (m, 3H), 3.75-3.58 (m, 1H), 3.23-3.09 (m, 2H), 2.91-2.74 (m, 2H), 1.93-1.80 (m, 2H), 1.67-1.42 (m, 4H), 1.42-1.15 (m, 16H), 0.82 (t, J=6.2 Hz, 6H); MS m/z 436 [M−H−Na]−.

Example 3

Sodium 3-((((2-decyl-1,3-dioxolan-4-yl)methoxy)carbonyl)amino)propane-1-sulfonate (JRW-1564)

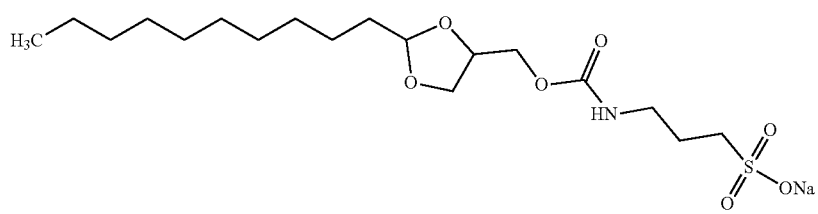

Step 1. (2-decyl-1,3-dioxolan-4-yl)methanol (JRW-1537)

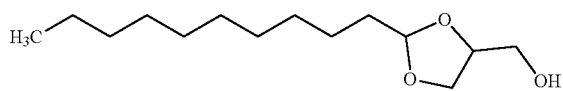 [SMILES: CCCCCCCCCCC1OCC(CO)O1]

To a solution of undecanal (14.8 g, 86.9 mmol) in heptane and toluene (1:2, 300 mL), glycerol (9.6 g, 104 mmol) and p-toluenesulfonic acid (299 mg, 1.7 mmol) was added. The mixture was heated to reflux using a Dean Stark trap condenser for 2 d. The reaction was neutralized with $NaHCO_3$ (0.04 eq) in water (100 mL). The organic layer was washed with more water. The organic layer was dried with sodium sulfate, filtered, concentrated, and purified with silica gel chromatography to afford desired product (18.6 g, 87%) as a colorless oil.

Step 2. (2-decyl-1,3-dioxolan-4-yl)methyl (4-nitrophenyl) carbonate (JRW-1539)

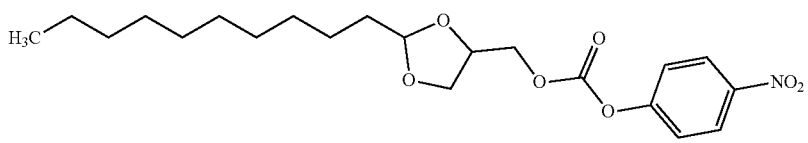 [SMILES: CCCCCCCCCCC1OCC(COC(=O)Oc2ccc([N+](=O)[O-])cc2)O1]

To a solution of (2-decyl-1,3-dioxolan-4-yl)methanol (18.6 g, 76.1 mmol) in THF (100 mL) at 0° C., 4-nitrophenyl carbonochloridate (23.0 g, 114 mmol) and pyridine (18.1 g, 228 mmol) was added. The suspension stirred for at 0° C. then warming to RT for 18 h. The reaction was concentrated under vacuum, suspended in heptanes, filtered, and the solid was washed with heptane. The filtrate was concentrated and purified with silica gel chromatography to afford desired product (21.3 g, 68%) as a white solid.

Step 3. Sodium 3-((((2-decyl-1,3-dioxolan-4-yl)methoxy)carbonyl)amino)propane-1-sulfonate (JRW-1564)

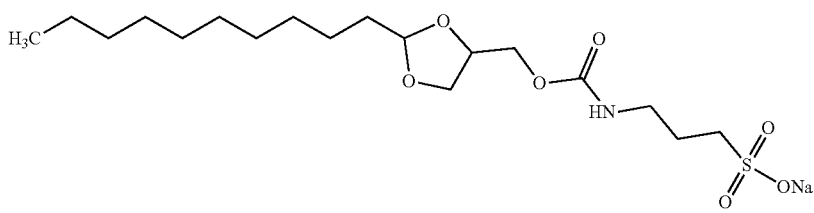

To a solution of (2-decyl-1,3-dioxolan-4-yl)methyl (4-nitrophenyl) carbonate (0.51 g, 1.25 mmol) in THF (20 mL), 3-aminopropane-1-sulfonic acid tetrabutylammonium (0.57 g, 1.5 mmol) was added. The mixture stirred for 4 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.45 g, 83%) as a white solid. $^1$H NMR (400 MHz, DMSO-d$_6$) δ 7.30-7.21 (m, 1H), 4.90 (t, J=4.8 Hz, 0.5H, diastereotopic), 4.82 (t, J=4.8 Hz, 0.5H, diastereotopic), 4.24-4.12 (m, 1H), 4.11-3.92 (m, 2H), 3.92-3.78 (m, 1H), 3.68-3.61 (m, 0.5H, diastereotopic), 3.52-3.46 (m, 0.5H, diastereotopic), 3.08-2.92 (m, 2H), 2.44-2.36 (m, 2H), 1.75-1.63 (m, 2H), 1.62-1.48 (m, 2H), 1.37-1.19 (m, 16H), 0.93-0.81 (m, 3H); MS m/z 408 [M−H−Na]−.

Example 4

Sodium 3-((((2-dodecyl-1,3-dioxolan-4-yl)methoxy)carbonyl)amino)propane-1-sulfonate (JRW-1574)

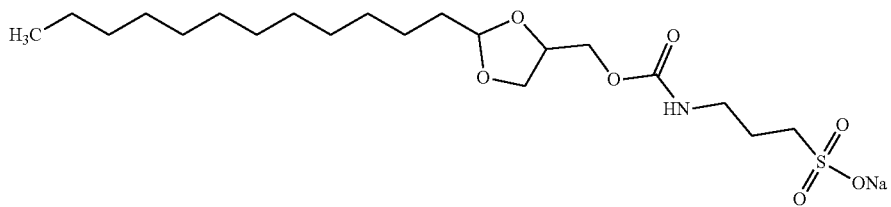

Step 1. (2-dodecyl-1,3-dioxolan-4-yl)methanol (JRW-1568)

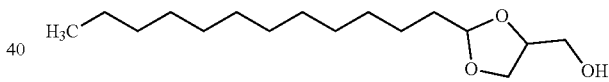

To a solution of tridecanal (10.0 g, 50.4 mmol) in heptane and toluene (1:2, 300 mL), glycerol (5.6 g, 60.5 mmol) and p-toluenesulfonic acid (173 mg, 1.0 mmol) was added. The mixture was heated to reflux using a Dean Stark trap condenser for 4 d. The reaction was neutralized with NaHCO$_3$ (0.04 eq) in water (100 mL). The organic layer was washed with more water. The organic layer was dried with sodium sulfate, filtered, concentrated, and purified with silica gel chromatography to afford desired product (12.5 g, 91%) as a colorless oil.

Step 2. (2-dodecyl-1,3-dioxolan-4-yl)methyl (4-nitrophenyl) carbonate (JRW-1571)

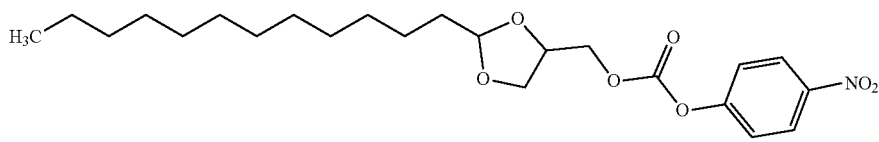 [SMILES: CCCCCCCCCCCCC1OCC(COC(=O)Oc2ccc([N+](=O)[O-])cc2)O1]

To a solution of 2-dodecyl-1,3-dioxolan-4-yl)methanol (12.5 g, 45.9 mmol) in THF (100 mL) at 0° C., 4-nitrophenyl carbonochloridate (11.1 g, 55.1 mmol) and pyridine (10.9 g, 137 mmol) was added. The suspension stirred for at 0° C. for 3 h. The reaction was concentrated under vacuum, suspended in heptanes, filtered, and the solid was washed with heptane. The filtrate was concentrated and purified with silica gel chromatography to afford crude product (12.0 g) as a white solid.

Step 3. Sodium 3-((((2-dodecyl-1,3-dioxolan-4-yl)methoxy)carbonyl)amino)propane-1-sulfonate (JRW-1574)

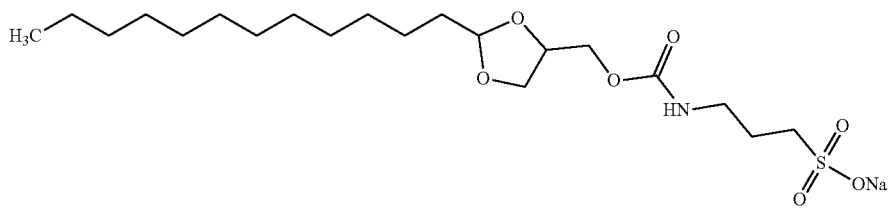

To a solution of (2-dodecyl-1,3-dioxolan-4-yl)methyl (4-nitrophenyl) carbonate (0.40 g, 0.91 mmol) in THF (20 mL), 3-aminopropane-1-sulfonic acid tetrabutylammonium (0.42 g, 1.1 mmol) was added. The mixture stirred for 2.5 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.31 g, 73%) as a white solid. $^1$H NMR (400 MHz, DMSO-$d_6$) δ 7.29-7.21 (m, 1H), 4.90 (t, J=4.8 Hz, 0.5H, diastereotopic) 4.82 (t, J=4.8 Hz, 0.5H, diastereotopic), 4.24-4.12 (m, 1H), 4.11-3.93 (m, 2H), 3.92-3.78 (m, 1H), 3.67-3.61 (m, 0.5H, diastereotopic), 3.53-3.45 (m, 0.5H, diastereotopic), 3.08-2.96 (m, 2H), 2.42-2.36 (m, 2H), 1.74-1.63 (m, 2H), 1.62-1.47 (m, 2H), 1.24 (s, 20H), 0.92-0.80 (m, 3H); MS m/z 436 [M−H−Na]−.

Example 5

Sodium 3-((((2-undecyl-1,3-dioxolan-4-yl)methoxy)carbonyl)amino)propane-1-sulfonate JRW-1565

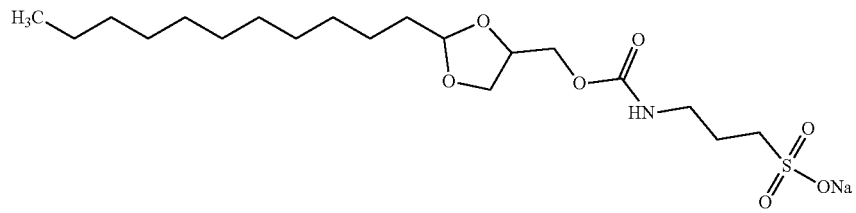

Step 1. (2-undecyl-1,3-dioxolan-4-yl)methanol (JRW-1538)

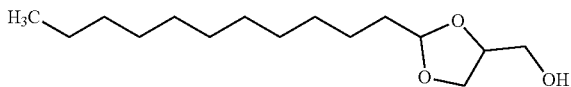 [SMILES: CCCCCCCCCCCC1OCC(CO)O1]

To a solution of dodecanal (14.8 g, 80.3 mmol) in heptane and toluene (1:2, 200 mL), glycerol (8.8 g, 96.3 mmol) and p-toluenesulfonic acid (276 mg, 1.6 mmol) was added. The mixture was heated to reflux using a Dean Stark trap condenser for 2 d. The reaction was neutralized with NaHCO₃ (0.04 eq) in water (100 mL). The organic layer was washed with more water. The organic layer was dried with sodium sulfate, filtered, concentrated, and purified with silica gel chromatography to afford desired product (14.8 g, 71%) as a white solid.

Step 2. 4-nitrophenyl ((2-undecyl-1,3-dioxolan-4-yl)methyl) carbonate (JRW-1540)

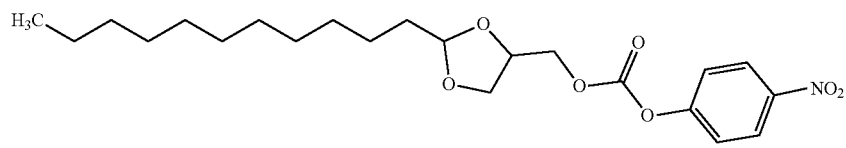 [SMILES: CCCCCCCCCCCC1OCC(COC(=O)Oc2ccc([N+](=O)[O-])cc2)O1]

To a solution of (2-undecyl-1,3-dioxolan-4-yl)methanol (14.8 g, 57.3 mmol) in THF (100 mL) at 0° C., 4-nitrophenyl carbonochloridate (17.3 g, 85.9 mmol) and pyridine (13.6 g, 172 mmol) was added. The suspension stirred for at 0° C. for 2 h. The reaction was concentrated under vacuum, suspended in heptanes, filtered, and the solid was washed with heptane. The filtrate was concentrated and purified with silica gel chromatography to afford crude product (14.5 g) as a white solid.

Step 3. Sodium 3-((((2-undecyl-1,3-dioxolan-4-yl)methoxy)carbonyl)amino)propane-1-sulfonate (JRW-1565)

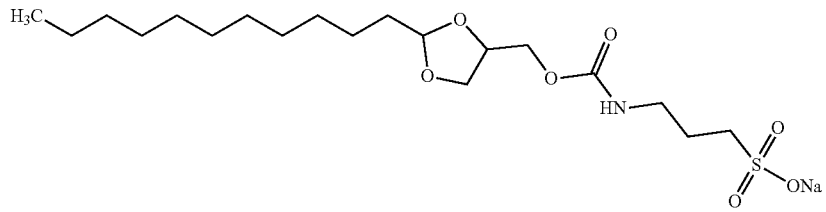

To a solution of 4-nitrophenyl ((2-undecyl-1,3-dioxolan-4-yl)methyl) carbonate (0.68 g, 1.61 mmol) in THF (20 mL), 3-aminopropane-1-sulfonic acid tetrabutylammonium (0.73 g, 1.9 mmol) was added. The mixture stirred for 3 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.35 g, 49%) as a white solid. $^1$H NMR (400 MHz, DMSO-$d_6$) δ 7.35-7.18 (m, 1H), 4.90 (t, J=4.8 Hz, 0.5H, diastereotopic), 4.82 (t, J=4.8 Hz, 0.5H, diastereotopic), 4.24-4.13 (m, 1H), 4.09-3.92 (m, 2H), 3.92-3.78 (m, 1H), 3.67-3.61 (m, 0.5H, diastereotopic), 3.52-3.46 (m, 0.5H, diastereotopic), 3.07-2.97 (m, 2H), 2.46-2.34 (m, 2H), 1.74-1.64 (m, 2H), 1.60-1.49 (m, 2H), 1.37-1.18 (m, 18H), 0.91-0.81 (m, 3H)); MS m/z 422 [M–H–Na]–.

Example 6

Sodium 3,3'-((4-((((2-methyl-2-undecyl-1,3-dioxolan-4-yl)methoxy)carbonyl)amino)phenyl)azanediyl)bis(propane-1-sulfonate) (SL-1735)

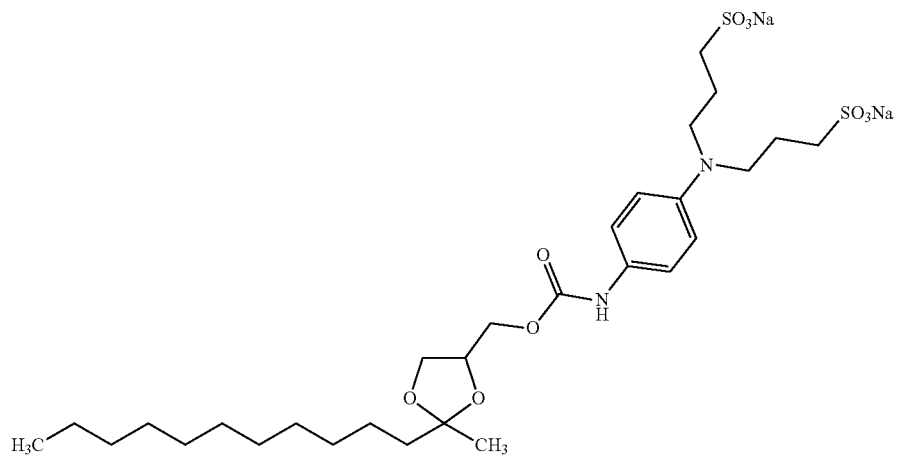

Step 1. (2-methyl-2-undecyl-1,3-dioxolan-4-yl)methanol (AF-0046)

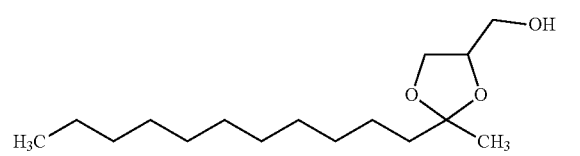 [SMILES: CCCCCCCCCCCC1(C)OCC(CO)O1]

To a solution of tridecan-2-one (5.0 g, 25.2 mmol) in heptane and toluene (1:2, 200 mL), glycerol (2.8 g, 30.2 mmol) and p-toluenesulfonic acid (86 mg, 0.50 mmol) was added. The mixture was heated to reflux using a Dean Stark trap condenser for 18 h. The reaction was neutralized with NaHCO$_3$ (0.04 eq) in water (100 mL). The organic layer was washed with more water. The organic layer was dried with sodium sulfate, filtered, concentrated, and purified with silica gel chromatography to afford desired product (4.1 g, 66%) as a colorless oil.

Step 2. (2-methyl-2-undecyl-1,3-dioxolan-4-yl)methyl (4-nitrophenyl) carbonate (AF-0047)

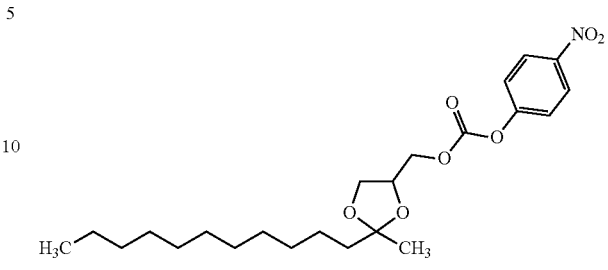

To a solution of (2-methyl-2-undecyl-1,3-dioxolan-4-yl)methanol (2.0 g, 7.3 mmol) in THF (50 mL) at 0° C., 4-nitrophenyl carbonochloridate (2.22 g, 11.0 mmol) and pyridine (1.7 g, 22 mmol) was added. The suspension stirred for at 0° C. for 2 h. The reaction was concentrated under vacuum, suspended in heptanes, filtered, and the solid was washed with heptane. The filtrate was concentrated and purified with silica gel chromatography to afford crude product (3.0 g) as a white solid.

Step 3. (2-methyl-2-undecyl-1,3-dioxolan-4-yl)methyl (4-aminophenyl)carbamate (SL-1733)

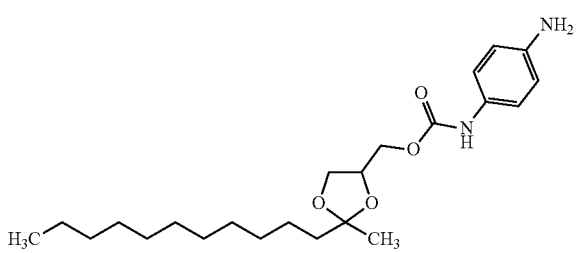 [SMILES: CCCCCCCCCCCC1(C)OCC(COC(=O)Nc2ccc(N)cc2)O1]

To a solution of (2-methyl-2-undecyl-1,3-dioxolan-4-yl)methyl (4-nitrophenyl) carbonate (1.0 g, 2.35 mmol) in DMF (6 mL), benzene-1,4-diamine (510 mg, 4.7 mmol) and diisopropylethylamine (0.61 g, 4.7 mmol) was added. The reaction stirred at RT for 4 h. The reaction was purified with silica gel chromatography to afford desired product (0.75 g, 78%) as a yellow solid. MS m/z 407 [M+H]+.

Step 4. Sodium 3,3'-((4-((((2-methyl-2-undecyl-1,3-dioxolan-4-yl)methoxy)carbonyl)amino)phenyl)azanediyl)bis(propane-1-sulfonate) (SL-1735)

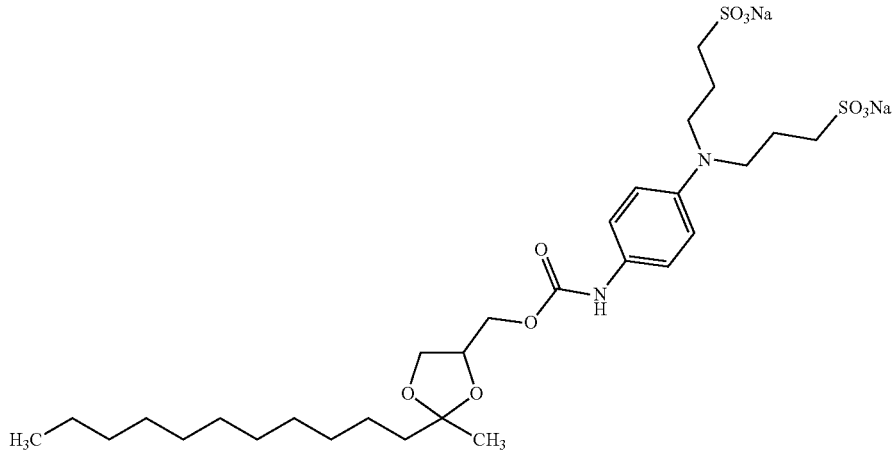

To a solution of (2-methyl-2-undecyl-1,3-dioxolan-4-yl)methyl (4-aminophenyl)carbamate (0.47 g, 1.16 mmol) in acetonitrile (9 mL), 1,2-oxathiolane 2,2-dioxide (423 mg, 3.47 mmol) and diisopropylethylamine (747 mg, 5.78 mmol) was added. The mixture was heated to 80° C. for 2 d. The reaction was purified with silica gel chromatography to afford the diisopropylethylamine salt as a yellow foam. The diisopropylethylamine product was dissolved in water and methanol (10:1, 10 mL), passed through a bissodium ion exchange resin, and lyophilized to afford desired product (0.73 g, 91%) as a white foam. MS m/z 649 [M–H–Na]–.

Example 7

Sodium 3-((((2-decyl-2-methyl-1,3-dioxolan-4-yl)methoxy)carbonyl)amino)propane-1-sulfonate (AF-0045)

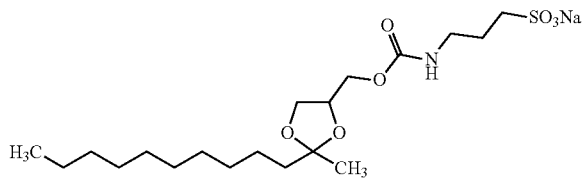

To a solution of 4-nitrophenyl (2-decyl-2-methyl-1,3-dioxolan-4-yl)methyl (4-nitrophenyl) carbonate (1.0 g, 2.36 mmol) in THF (10 mL), 3-aminopropane-1-sulfonic acid tetrabutylammonium (1.1 g, 2.8 mmol) was added. The mixture stirred for 30 min at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.77 g, 49%) as a white solid. $^1$H NMR (400 MHz, DMSO-$d_6$) δ 7.31-7.18 (m, 1H), 4.27-4.11 (m, 1H), 4.10-3.95 (m, 2H), 3.93-3.82 (m, 1H), 3.67-3.52 (m, 1H), 3.01 (q, J=6.7 Hz, 2H), 2.43-2.31 (m, 2H), 1.74-1.62 (m, 2H), 1.61-1.48 (m, 2H), 0.93-0.80 (m, 3H); MS m/z 422 [M–H–Na]–.

Example 8

Sodium 3-((((2-methyl-2-undecyl-1,3-dioxolan-4-yl)methoxy)carbonyl)amino)propane-1-sulfonate (JRW-1573)

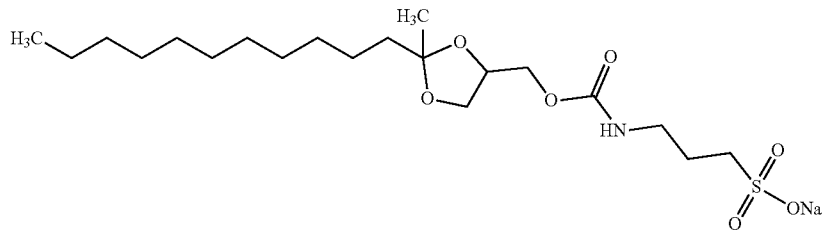

To a solution of (2-methyl-2-undecyl-1,3-dioxolan-4-yl)methyl (4-nitrophenyl) carbonate (0.30 g, 0.68 mmol) in THF (20 mL), 3-aminopropane-1-sulfonic acid tetrabutylammonium (0.31 g, 0.82 mmol) was added. The mixture stirred for 18 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.21 g, 67%) as a white solid. $^1$H NMR (400 MHz, DMSO-$d_6$) δ 7.29-7.19 (m, 1H), 4.28-4.11 (m, 1H), 4.07-3.96 (m, 2H), 3.94-3.81 (m, 1H), 3.69-3.52 (m, 1H), 3.02 (q, J=6.7 Hz, 2H), 2.44-2.34 (m, 2H), 1.75-1.63 (m, 2H), 1.60-1.47 (m, 2H), 1.35-1.18 (m, 21H), 0.91-0.81 (m, 3H); MS m/z 436 [M−H−Na]−.

Example 9

Sodium 2-hydroxy-3-((((2-methyl-2-undecyl-1,3-dioxolan-4-yl)methoxy)carbonyl)amino)propane-1-sulfonic Acid (HW-0797)

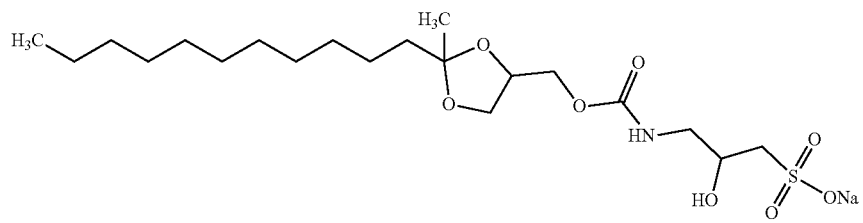

To a solution of (2-methyl-2-undecyl-1,3-dioxolan-4-yl)methyl (4-nitrophenyl) carbonate (0.17 g, 0.39 mmol) in acetonitrile (20 mL), a solution of sodium 3-amino-2-hydroxypropane-1-sulfonate (0.066 g, 0.43 mmol) and sodium bicarbonate (49 mg, 0.58 mmol) in water (10 ml) was added. The mixture stirred for 3 h at RT. The reaction was concentrated under vacuum and purified with silica gel chromatography using heptanes/ethyl acetate and then with DCM/MeOH to afford the product as the sodium salt (86 mg, 49%). $^1$H NMR (400 MHz, DMSO-$d_6$) δ 7.19 (t, J=5.8 Hz, 1H), 5.03 (s, 1H), 4.21-4.11 (m, 1H), 4.06-3.97 (m, 2H), 3.94-3.79 (m, 2H), 3.96-3.87 (m, 1H), 3.86-3.76 (m, 1H), 3.65-3.61 (m, 1H), 3.10-2.94 (m, 2H), 2.6-2.59 (m, 1H), 2.43-2.32 (m, 1H), 1.59-1.47 (m, 2H), 1.35-1.18 (m, 21H), 0.91-0.79 (m, 3H); MS m/z 453 [M−H−Na]−.

Example 10

Sodium 3-((((2-decyl-1,3-dioxolan-4-yl)methoxy)carbonyl)amino)-2-hydroxypropane-1-sulfonic Acid (HW-0801)

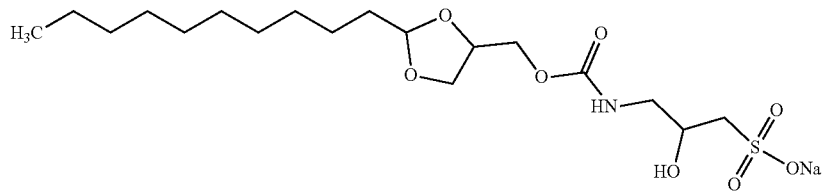

To a solution of (2-decyl-1,3-dioxolan-4-yl)methyl (4-nitrophenyl) carbonate (0.23 g, 0.56 mmol) in acetonitrile (20 mL), a solution of sodium 3-amino-2-hydroxypropane-1-sulfonate (0.11 g, 0.67 mmol) and sodium bicarbonate (72 mg, 0.56 mmol) in water (10 ml) was added. The mixture stirred for 3 h at RT. The reaction was concentrated under vacuum and purified with silica gel chromatography using heptanes/ethyl acetate and then with DCM/MeOH to afford the product as the sodium salt (0.16 mg, 67%). $^1$H NMR (400 MHz, DMSO-d$_6$) δ 7.19 (t, J=5.8 Hz, 1H), 5.03 (s, 1H), 4.91-4.80 (m, 1H), 4.23-4.14 (m, 1H), 4.06-3.95 (m, 2H), 3.90-3.78 (m, 2H), 3.65-3.48 (m, 1H), 3.10-2.93 (m, 2H), 2.69-2.58 (m, 1H), 2.43-2.30 (m, 1H), 1.62-1.47 (m, 2H), 1.35-1.18 (m, 16H), 0.91-0.79 (m, 3H); MS m/z 425 [M–H–Na]–.

Example 11

Sodium 3-((((2-dodecyl-1,3-dioxolan-4-yl)methoxy)carbonyl)amino)-2-hydroxypropane-1-sulfonic Acid (HW-0807)

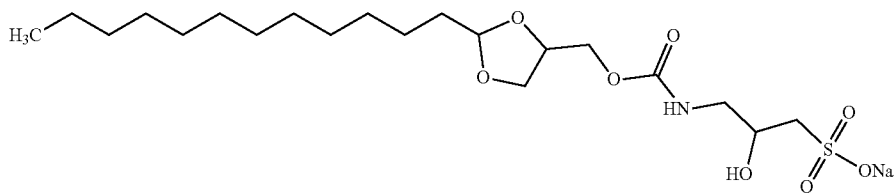

To a solution of (2-dodecyl-1,3-dioxolan-4-yl)methyl (4-nitrophenyl) carbonate (0.38 g, 0.87 mmol) in acetonitrile (20 mL), a solution of sodium 3-amino-2-hydroxypropane-1-sulfonate (0.15 g, 0.96 mmol) and sodium bicarbonate (146 mg, 1.74 mmol) in water (10 ml) was added. The mixture stirred for 3 h at RT. The reaction was concentrated under vacuum and purified with silica gel chromatography using heptanes/ethyl acetate and then with DCM/MeOH to afford the product as the sodium salt (160 mg, 41%). $^1$H NMR (400 MHz, DMSO-d$_6$) δ 7.19 (t, J=5.8 Hz, 1H), 5.03 (s, 1H), 4.91-4.80 (m, 1H), 4.23-4.14 (m, 1H), 4.06-3.95 (m, 2H), 3.90-3.78 (m, 2H), 3.65-3.48 (m, 1H), 3.10-2.94 (m, 2H), 2.71-2.59 (m, 1H), 2.43-2.31 (m, 1H), 1.61-1.47 (m, 2H), 1.35-1.18 (m, 20H), 0.91-0.79 (m, 3H); MS m/z 453 [M–H–Na]–.

Example 12

Sodium 2-hydroxy-3-((((2-undecyl-1,3-dioxolan-4-yl)methoxy)carbonyl)amino)propane-1-sulfonate (HW-0805)

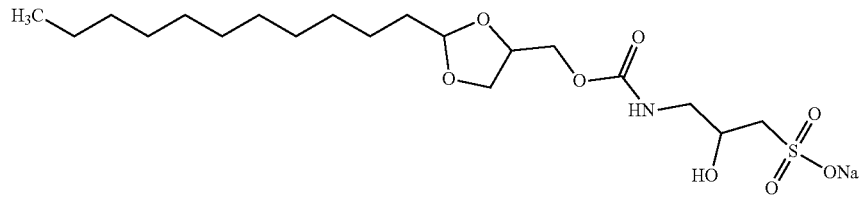

To a solution of 4-nitrophenyl ((2-undecyl-1,3-dioxolan-4-yl)methyl) carbonate (0.38 g, 0.90 mmol) in acetonitrile (20 mL), a solution of sodium 3-amino-2-hydroxypropane-1-sulfonate (0.15 g, 0.99 mmol) and sodium bicarbonate (151 mg, 1.79 mmol) in water (10 ml) was added. The mixture stirred for 3 h at RT. The reaction was concentrated under vacuum and purified with silica gel chromatography using heptanes/ethyl acetate and then with DCM/MeOH to afford the product as the sodium salt (150 mg, 38%). $^1$H NMR (400 MHz, DMSO-$d_6$) δ 7.19 (t, J=5.8 Hz, 1H), 5.03 (s, 1H), 4.91-4.80 (m, 1H), 4.23-4.14 (m, 1H), 4.06-3.95 (m, 2H), 3.90-3.78 (m, 2H), 3.65-3.48 (m, 1H), 3.10-2.93 (m, 2H), 2.68-2.59 (m, 1H), 2.43-2.32 (m, 1H), 1.60-1.47 (m, 2H), 1.35-1.18 (m, 18H), 0.91-0.79 (m, 3H); MS m/z 439 [M−H−Na]−.

Example 13

Sodium 3-((((2,2-dipentyl-1,3-dioxolan-4-yl)methoxy)carbonyl)amino)-2-hydroxypropane-1-sulfonate (JZ-0164)

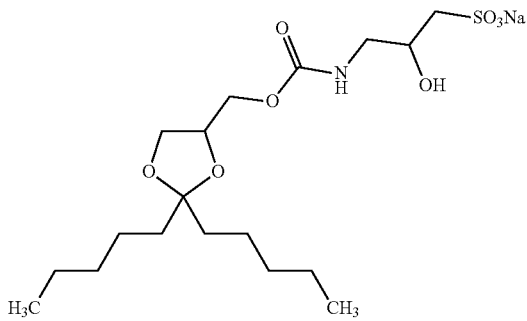

Step 1. (2,2-dipentyl-1,3-dioxolan-4-yl)methanol (JZ-0144)

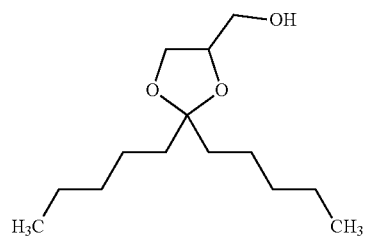 [SMILES: CCCCCC1(CCCCC)OCC(CO)O1]

To a round bottom flask with undecan-6-one (5.11 g, 30 mmol), glycerol (3.32 g, 1.2 equiv, 36 mmol) and 90 mL mixed solvent (80 mL toluene and 10 mL heptane), p-TsOH (103 mg, 2 mol %) was added. The mixture was refluxed under $N_2$ with Dean Stark for 18 h. The mixture was cooled down to RT and diluted with 300 mL EtOAc. Organic layer was washed with 2% NaHCO$_3$ (80 mL) twice, then dried over Na$_2$SO$_4$. The crude was then purified by flash column to yield a colorless oil product (6.73 g, 92%). $^1$HNMR (400 MHz, Chloroform-d): δ 4.24 (m, 1H), 4.05 (dd, J=8.0, 6.6 Hz, 1H), 3.85-3.74 (m, 2H), 3.61 (dd, J=11.7, 5.1 Hz, 1H), 1.79 (s, 1H), 1.70-1.58 (m, 4H), 1.47-1.25 (m, 12H), 0.91 (t, J=6.9 Hz, 6H).

Step 2. (2,2-dipentyl-1,3-dioxolan-4-yl)methyl (4-nitrophenyl) carbonate (JZ-0151)

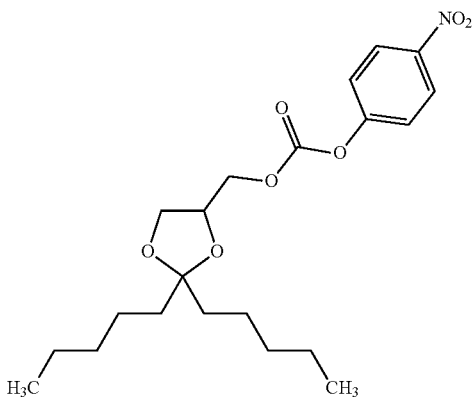 [SMILES: CCCCCC1(CCCCC)OCC(COC(=O)Oc2ccc([N+](=O)[O-])cc2)O1]

To a round bottom flask with (2,2-dipentyl-1,3-dioxolan-4-yl)methanol (3.07, 12.56 mmol), p-nitrophenyl chloroformate (3.80 g, 1.5 equiv, 18.84 mmol) and 30 mL THF, pyridine (3.04 mL, 3 equiv) at 0° C. was added. The reaction was then warmed up to RT and stirred for 2 h. The mixture was concentrated on vacuum, washed with heptane, filtered off solids. The filtrated was collected and then purified by flash column. Light yellow oil product was obtained (3.84 g, 75%). $^1$HNMR (400 MHz, Chloroform-d): δ 8.38-8.22 (m, 2H), 7.49-7.36 (m, 2H), 4.51-4.29 (m, 3H), 4.21-4.12 (m, 1H), 3.81 (dd, J=8.4, 6.5 Hz, 1H), 1.74-1.58 (m, 4H), 1.46-1.21 (m, 12H), 0.91 (q, J=6.8 Hz, 6H).

Step 3. Sodium 3-((((2,2-dipentyl-1,3-dioxolan-4-yl)methoxy)carbonyl)amino)-2-hydroxypropane-1-sulfonate (JZ-0164)

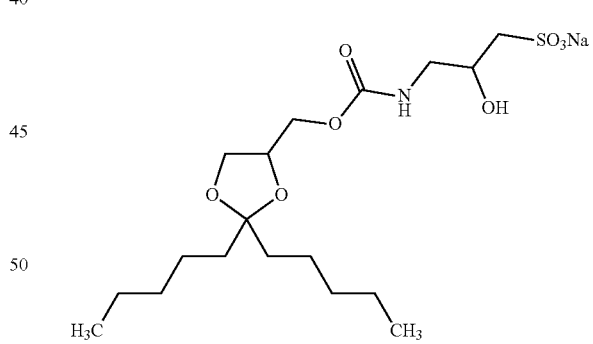

To a round bottom flask with (2,2-dipentyl-1,3-dioxolan-4-yl)methyl (4-nitrophenyl) carbonate (327 mg, 0.8 mmol), 3-amino-2-hydroxypropane-1-sulfonic acid (186 mg, 1.5 equiv, 1.2 mmol) and 8 mL can, NaOH aq solution (1.6 mL) at RT was added. The reaction was stirred at 50° C. for 4 h. The crude mixture was dried on the vacuum and then purified by flash column. A white solid product (200 mg, 56% yield) was obtained. $^1$HNMR (400 MHz, DMSO-$d_6$): δ 7.17 (t, J=6.0 Hz, 1H), 5.04 (d, J=1.8 Hz, 1H), 4.19 (m, 1H), 4.11-3.97 (m, 2H), 3.94-3.76 (m, 2H), 3.57 (t, J=7.6 Hz, 1H), 3.12-2.91 (m, 2H), 2.63 (dd, J=13.5, 3.1 Hz, 1H), 2.37 (dd, J=13.5, 9.1 Hz, 1H), 1.52 (m, 4H), 1.36-1.14 (m, 12H), 0.86 (t, J=6.8 Hz, 6H); MS m/z 424 [M−Na−H]−.

Example 14

Sodium 3-((((2,2-dipentyl-1,3-dioxolan-4-yl)methoxy)carbonyl)amino)propane-1-sulfonate (JZ-0177)

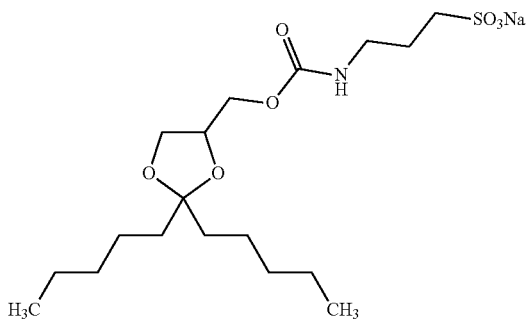

To a round bottom flask with (2,2-dipentyl-1,3-dioxolan-4-yl)methyl (4-nitrophenyl) carbonate (205 mg, 0.5 mmol), 3-aminopropane-1-sulfonic acid (104 mg, 0.75 mmol) and 5 mL can, 1M NaOH aq solution (1 mL) at RT was added. The reaction was stirred at 50° C. for 3 h. The crude mixture was then concentrated on vacuum, purified by flash column. A white color solid product was obtained (210 mg, 97%). $^1$HNMR (400 MHz, DMSO-$d_6$): δ 7.24 (t, J=5.8 Hz, 1H), 4.19 (qd, J=6.7, 4.2 Hz, 1H), 4.09-3.97 (m, 2H), 3.87 (dd, J=11.4, 6.5 Hz, 1H), 3.57 (dd, J=8.2, 6.9 Hz, 1H), 3.01 (q, J=6.7 Hz, 2H), 2.43-2.35 (m, 2H), 1.68 (m, 2H), 1.52 (m, 4H), 1.36-1.15 (m, 12H), 0.90-0.80 (m, 6H). MS m/z 408 [M−Na−H]−.

Example 15

Sodium 3-((((2,2-dihexyl-1,3-dioxolan-4-yl)methoxy)carbonyl)amino)-2-hydroxypropane-1-sulfonate (JZ-0179)

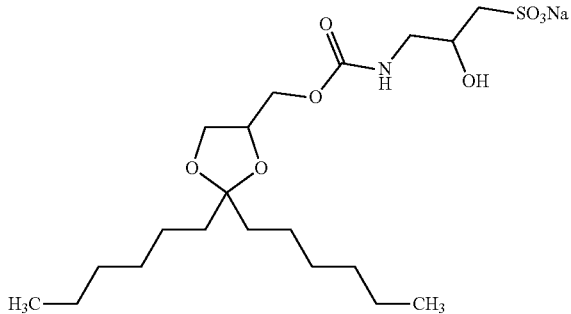

To a round bottom flask with (2,2-dihexyl-1,3-dioxolan-4-yl)methyl (4-nitrophenyl) carbonate (88 mg, 0.2 mmol), 3-amino-2-hydroxypropane-1-sulfonic acid (47 mg, 0.3 mmol) and 2 mL can, 1M NaOH aq solution (0.4 mL) at RT was added. The reaction was stirred at RT for 4 h. The mixture was concentrated on vacuum and then purified by flash column. White solid product was obtained (41 mg, 43%). $^1$H NMR (400 MHz, DMSO-$d_6$) δ 7.17 (t, J=6.0 Hz, 1H), 5.04 (d, J=1.8 Hz, 1H), 4.25-4.15 (m, 1H), 4.09-3.97 (m, 2H), 3.93-3.79 (m, 2H), 3.62-3.54 (m, 1H), 3.01 (m, 2H), 2.64 (dd, J=13.5, 3.1 Hz, 1H), 2.37 (dd, J=13.5, 9.1 Hz, 1H), 1.52 (m, 4H), 1.26 (q, J=5.0, 2.8 Hz, 16H), 0.91-0.82 (m, 6H). MS m/z 452 [M−Na−H]−.

Example 16

Sodium 3-((2,2-bis(pentyloxy)propoxy)carbonyl)propane-1-sulfonate (RBK-0168)

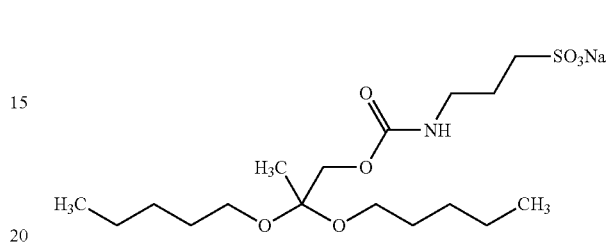

Step 1. Pentyl 2,2-bis(pentyloxy)propanoate (RBK-0155-1)

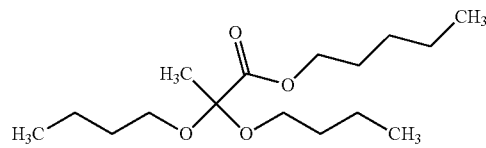 [SMILES: CCCCCOC(=O)C(C)(OCCCC)OCCCC]

To a solution of methyl pyruvate (10.0 g, 97.95 mmol) and 1-proponal (40.1 g, 454.91 mmol) in toluene (100 mL), p-toluenesulfonic acid (190 mg, 1.1 mmol) was added. The mixture was heated to reflux using a Dean Stark trap condenser for 2 d. The reaction was neutralized with NaHCO$_3$ (0.04 eq) in water (150 mL). The organic layer was washed with more water. The organic layer was dried with sodium sulfate, filtered, concentrated, and purified with silica gel chromatography (0-10% EtOAc/heptane) to afford desired product (22.5 g, 17%) as a colorless oil.

Step 2. 2,2-bis(pentyloxy)propan-1-ol (RBK-0156-1)

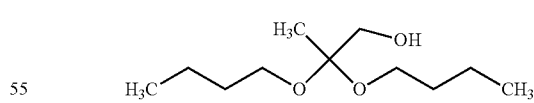

To a solution of pentyl 2,2-bis(pentyloxy)propanoate (9.2 g, 29.1 mmol) in THF (100 mL) at 0° C., lithium aluminum hydride (6.4 mL of 2.4 M solution in THF, 15.5 mmol) was added. The mixture was then stirred at RT for 1 h. The reaction was again cooled to 0° C., and diethyl ether (300 mL) was added followed dropwise addition of 9:1 mixture of EtOAc/H$_2$O (100 mL). The white precipitate was filtered. The filtrate was concentrated and purified with silica gel chromatography (0-10% EtOAc/heptane) to afford product (5.7 g, 75%) as a colorless oil.

Step 3. 2,2-bis(pentyloxy)propyl 4-nitrophenyl Carbonate (RBK-0158-2)

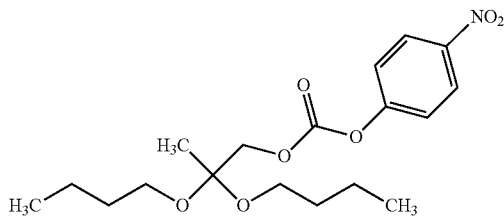 [SMILES: CCCCOC(C)(COC(=O)Oc1ccc([N+](=O)[O-])cc1)OCCCC]

To a solution of 2,2-bis(hexyloxy)propan-1-ol (5.4 g, 23.2 mmol) in THF (60 mL) at 0° C., 4-nitrophenyl carbonochloridate (7.6 g, 37.9 mmol) and pyridine (4.2 mL, 69.7 mmol) was added. The suspension stirred for at 0° C. for 2 h. The reaction was diluted with heptane (100 mL) and the white solid filtered. The filtrate was concentrated and purified with silica gel chromatography to afford crude product (5.6 g) as a yellow oil.

Step 4. Sodium 3-((2,2-bis(pentyloxy)propoxy)carbonyl)propane-1-sulfonate (RBK-0168)

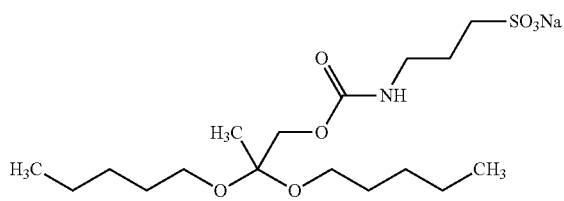

To a solution of 2,2-bis(pentyloxy)propyl 4-nitrophenyl carbonate (0.45 g, 1.0 mmol) in THF (50 mL), 3-aminopropane-1-sulfonic acid tetrabutylammonium (0.43 g, 1.1 mmol) was added. The mixture stirred for 3 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.48 g, 50%) as a light yellow solid. $^1$H NMR (400 MHz, DMSO-$d_6$) δ 7.27-7.24 (m, 1H), 3.90 (s, 2H), 3.42-3.35 (m, 4H), 3.02 (q, J=6.7 Hz, 2H), 2.45-2.37 (m, 2H), 1.76-1.63 (m, 2H), 1.51-1.41 (m, 4H), 1.36-1.22 (m, 11H), 0.93-0.82 (m, 6H); MS m/z 395 [M–H–Na]–.

Example 17

Sodium 3-((2,2-bis(hexyloxy)propoxy)carbonyl)propane-1-sulfonate (RBK-169)

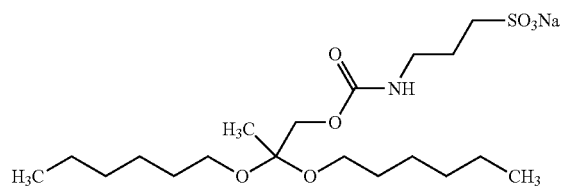

Step 1. Hexyl 2,2-bis(hexyloxy)propanoate (RBK-0161-1)

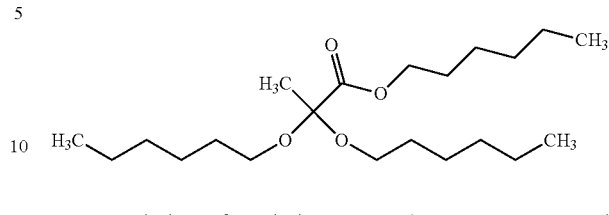

To a solution of methyl pyruvate (10.0 g, 97.95 mmol) and 1-hexanol (40.1 g, 392.5 mmol) in toluene (100 mL), p-toluenesulfonic acid (190 mg, 1.1 mmol) was added. The mixture was heated to reflux using a Dean Stark trap condenser for 2 d. The reaction was neutralized with NaHCO$_3$ (0.04 eq) in water (150 mL). The organic layer was washed with more water. The organic layer was dried with sodium sulfate, filtered, concentrated, and purified with silica gel chromatography (0-10% EtOAc/heptane) to afford desired product (25.3 g, 18%) as a colorless oil.

Step 2. 2,2-bis(hexyloxy)propan-1-ol (RBK-0162-1)

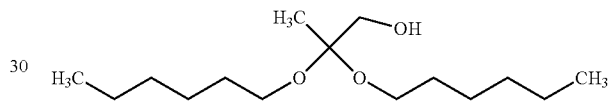

To a solution of hexyl 2,2-bis(hexyloxy)propanoate (13.2 g, 36.8 mmol) in THF (100 mL) at 0° C., lithium aluminum hydride (6.4 mL of 2.4 M solution in THF, 15.5 mmol) was added. The mixture was then stirred at RT for 1 h. The reaction was again cooled to 0° C., and diethyl ether (300 mL) was added followed dropwise addition of 9:1 mixture of EtOAc/H$_2$O (100 mL). The white precipitate was filtered. The filtrate was concentrated and purified with silica gel chromatography (0-10% EtOAc/heptane) to afford product (5.9 g, 59%) as a colorless oil.

Step 3. 2,2-bis(hexyloxy)propyl 4-nitrophenyl Carbonate (RBK-0165-1)

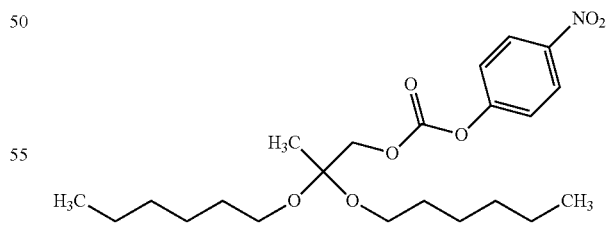

To a solution of 2,2-bis(hexyloxy)propan-1-ol (5.4 g, 23.2 mmol) in THF (60 mL) at 0° C., 4-nitrophenyl carbonochloridate (7.6 g, 37.9 mmol) and pyridine (4.2 mL, 69.7 mmol) was added. The suspension stirred for at 0° C. for 2 h. The reaction was diluted with heptane (100 mL), and the white solid filtered. The filtrate was concentrated and purified with silica gel chromatography to afford crude product (3.6 g) as a yellow oil.

Step 4. Sodium 3-((2,2-bis(hexyloxy)propoxy)carbonyl)propane-1-sulfonate (RBK-0169-1)

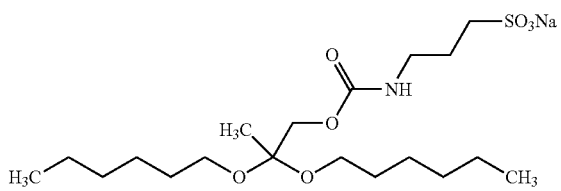

To a solution of 2,2-bis(hexyloxy)propyl 4-nitrophenyl carbonate (0.40 g, 0.94 mmol) in THF (50 mL), 3-aminopropane-1-sulfonic acid tetrabutylammonium (0.43 g, 1.1 mmol) was added. The mixture stirred for 3 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (0.24 g, 56%) as a white solid. $^1$H NMR (400 MHz, DMSO-$d_6$) δ 7.25 (t, J=5.8 Hz, 1H), 3.90 (s, 2H), 3.41-3.34 (m, 4H), 3.02 (q, J=6.7 Hz, 3H), 2.45-2.36 (m, 2H), 1.75-1.64 (m, 2H), 1.51-1.40 (m, 4H), 1.36-1.22 (m, 15H), 0.93-0.82 (m, 6H); MS m/z 423 [M–H–Na]–.

Example 18

Sodium 3-(((2,2-diheptyl-1,3-dioxolan-4-yl)methoxy)carbonyl)propane-1-sulfonate (RBK-170)

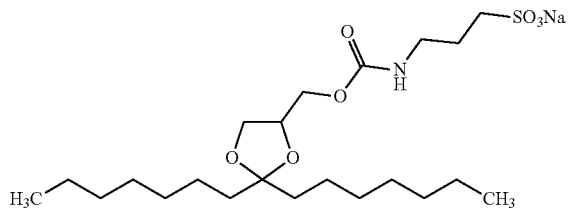

Step 1. (2,2-diheptyl-1,3-dioxolan-4-yl)methanol (JZ-0142)

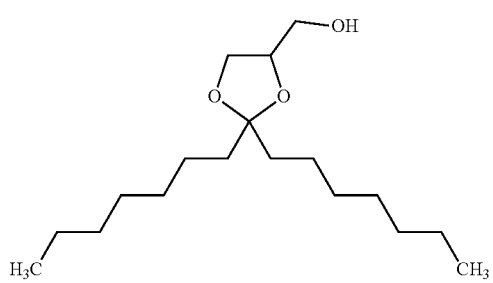 [SMILES: CCCCCCCC1(CCCCCCC)OCC(CO)O1]

To a round bottom flask with pentadecan-8-one (2.26 g, 10 mmol), glycerol (1.11 g, 1.2 equiv, 12 mmol) and 36 mL mixed solvent (24 mL toluene and 12 mL heptane), p-TsOH (34.5 mg, 2 mol %) was added. The mixture was refluxed under $N_2$ with Dean Stark for 18 h. The mixture was cooled down to RT and diluted with 100 mL EtOAc. Organic layer was washed with 2% NaHCO$_3$ (20 mL) twice, then dried over Na$_2$SO$_4$. The crude was then purified by flash column to yield a colorless oil product (2.65 g, 88%). $^1$H NMR (400 MHz, Chloroform-d) δ 4.28-4.20 (m, 1H), 4.09-4.01 (m, 1H), 3.82-3.72 (m, 2H), 3.65-3.58 (m, 1H), 1.70-1.56 (m, 4H), 1.46-1.21 (m, 20H), 0.95-0.83 (m, 6H).

Step 2. (2,2-diheptyl-1,3-dioxolan-4-yl)methyl (4-nitrophenyl) carbonate (JZ-0143)

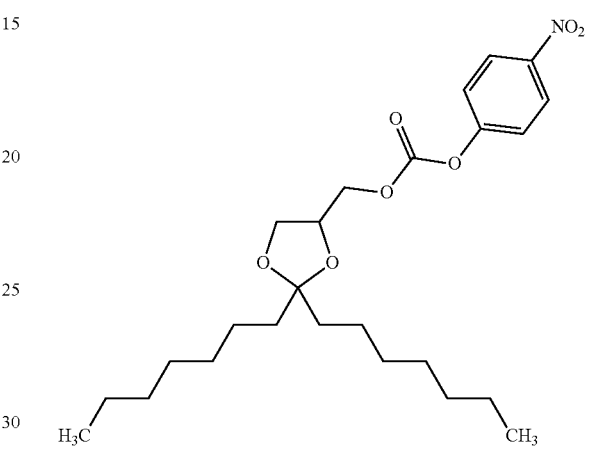

To a round bottom flask with (2,2-diheptyl-1,3-dioxolan-4-yl)methanol (2.65 g, 8.82 mmol), p-nitrophenyl chloroformate (2.67 g, 1.5 equiv, 13.2 mmol) and 25 mL THF was added pyridine (2.14 mL, 3 equiv) at 0° C. The reaction was then warmed up to RT and stirred for 2 h. The mixture was concentrated on vacuum, washed with heptane, filtered off solids. The filtrated was collected and then purified by flash column. Light yellow oil product was obtained (3.93 g, 96%). $^1$H NMR (400 MHz, Chloroform-d) δ 8.38-8.25 (m, 2H), 7.47-7.35 (m, 2H), 4.51-4.28 (m, 3H), 4.21-4.10 (m, 1H), 3.80 (dd, J=8.4, 6.4 Hz, 1H), 1.73-1.59 (m, 4H), 1.48-1.20 (m, 20H), 0.95-0.83 (m, 6H).

Step 3. Sodium 3-(((2,2-diheptyl-1,3-dioxolan-4-yl)methoxy)carbonyl)propane-1-sulfonate (RBK-170)

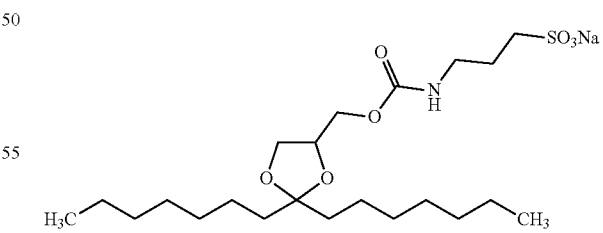

To a solution of (2,2-diheptyl-1,3-dioxolan-4-yl)methyl 4-nitrophenyl carbonate (0.40 g, 0.86 mmol) in THF (50 mL), 3-aminopropane-1-sulfonic acid tetrabutylammonium (0.39 g, 1.0 mmol) was added. The mixture stirred for 3 h at RT. The reaction was concentrated under vacuum and purified with silica gel chromatography using heptanes/ethyl acetate and then with DCM/MeOH to afford the product as the tetrabutylammonium salt. The tetrabutylammonium product was dissolved in water and methanol (10:1, 10 mL), passed through a bissodium ion exchange resin, and lyophilized to afford desired product (90 mg, 22%) as a yellow solid. $^1$H NMR (400 MHz, DMSO-d$_6$) δ 7.25 (t, J=5.7 Hz, 1H), 4.23-4.14 (m, 1H), 4.07-3.96 (m, 2H), 3.91-3.82 (m, 1H), 3.61-3.53 (m, 1H), 3.02 (q, J=6.7 Hz, 2H), 2.44-2.36 (m, 2H), 1.75-1.62 (m, 2H), 1.56-1.46 (m, 4H), 1.33-1.17 (m, 20H), 0.98-0.82 (m, 6H). MS m/z 463 [M−H−Na]−.

Example 19

Sodium 3-((2,2-bis(pentyloxy)propoxy)carbonyl)-2-hydroxypropane-1-sulfonate (RBK-0171)

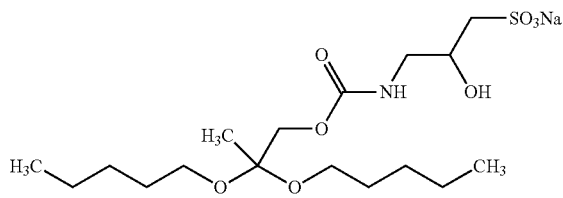

To a solution of 2,2-bis(pentyloxy)propyl 4-nitrophenyl carbonate (0.50 g, 1.26 mmol) in THF (10 mL) and H$_2$O (10 mL), sodium 3-amino-2-hydroxypropane-1-sulfonate (0.46 g, 2.5 mmol) and NaHCO$_3$ (211 mg, 2.5 mmol) was added. The mixture stirred for 3 h at RT, and celite was added. The reaction mixture was concentrated and purified with silica gel chromatography using heptanes/ethyl acetate (0-100%) and then with DCM/MeOH. The fractions were collected via TLC stained with potassium permanganate solution. Fractions were concentrated and lyophilized to afford desired product (0.13 g, 23%) as a white solid. $^1$H NMR (400 MHz, DMSO-d$_6$) δ 7.19 (t, J=5.9 Hz, 1H), 5.05 (s, 1H), 3.97-3.80 (m, 3H), 3.43-3.33 (m, 4H), 3.30 (s, 2H), 3.09-2.95 (m, 2H), 2.69-2.60 (m, 1H), 2.42-2.34 (m, 1H), 1.52-1.41 (m, 4H), 1.32-1.22 (m, 8H), 0.91-0.83 (m, 6H); MS m/z 411 [M−H−Na]−.

Example 20

Sodium 3-((2,2-bis(hexyloxy)propoxy)carbonyl)-2-hydroxypropane-1-sulfonate (RBK-0172)

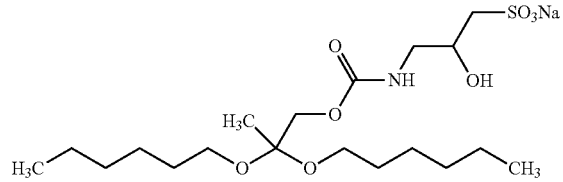

To a solution of 2,2-bis(hexyloxy)propyl 4-nitrophenyl carbonate (0.50 g, 1.2 mmol) in THF (10 mL) and H$_2$O (10 mL), sodium 3-amino-2-hydroxypropane-1-sulfonate (0.42 g, 2.4 mmol) and NaHCO$_3$ (197 mg, 2.4 mmol) was added. The mixture stirred for 3 h at RT, and celite was added. The reaction mixture was concentrated and purified with silica gel chromatography using heptanes/ethyl acetate (0-100%) and then with DCM/MeOH. The fractions were collected via TLC stained with potassium permanganate solution. Fractions were concentrated and lyophilized to afford desired product (0.18 g, 34%) as a white solid. $^1$H NMR (400 MHz, DMSO-d$_6$) δ 7.24-7.15 (m, 1H), 5.03 (s, 1H), 3.96-3.78 (m, 3H), 3.42-3.30 (m, 4H), 3.22-3.14 (m, 1H), 3.08-2.94 (m, 2H), 2.69-2.61 (m, 2H), 2.43-2.34 (m, 1H), 1.51-1.40 (m, 4H), 1.36-1.19 (m, 12H), 0.90-0.82 (m, 6H); MS m/z 439 [M−H−Na]−.

Example 21

Sodium 3-(((2,2-diheptyl-1,3-dioxolan-4-yl)methoxy)carbonyl)-2-hydroxypropane-1-sulfonate (RBK-0173)

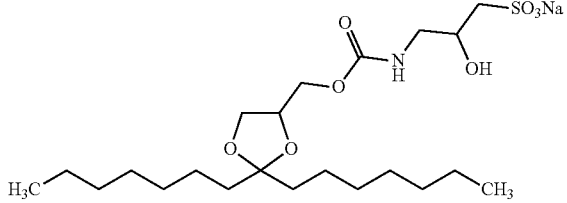

To a solution of (2,2-diheptyl-1,3-dioxolan-4-yl)methyl 4-nitrophenyl carbonate (0.50 g, 1.1 mmol) in THF (10 mL) and H$_2$O (10 mL), sodium 3-amino-2-hydroxypropane-1-sulfonate (0.46 g, 2.5 mmol) and NaHCO$_3$ (211 mg, 2.5 mmol) was added. The mixture stirred for 3 h at RT, and celite was added. The reaction mixture was concentrated and purified with silica gel chromatography using heptanes/ethyl acetate (0-100%) and then with DCM/MeOH. The fractions were collected via TLC stained with potassium permanganate solution. Fractions were concentrated and lyophilized to afford desired product (0.21 g, 38%) as a white solid. $^1$H NMR (400 MHz, DMSO-d$_6$) δ 7.18 (t, J=6.0 Hz, 1H), 5.02 (s, 1H), 4.23-4.14 (m, 1H), 4.08-3.96 (m, 2H), 3.93-3.77 (m, 2H), 3.62-3.52 (m, 1H), 3.10-2.93 (m, 2H), 2.69-2.60 (m, 1H), 2.39 (dd, J=13.5, 8.9 Hz, 1H), 1.57-1.44 (m, 4H), 1.33-1.16 (m, 18H), 0.90-0.82 (m, 6H); MS m/z 479 [M−H−Na]−.

Example 22

Sodium 3,3'-((4-((((2-undecyl-1,3-dioxolan-4-yl)methoxy)carbonyl)amino)phenyl)-azanediyl)bis(propane-1-sulfonate) (CS-0843)

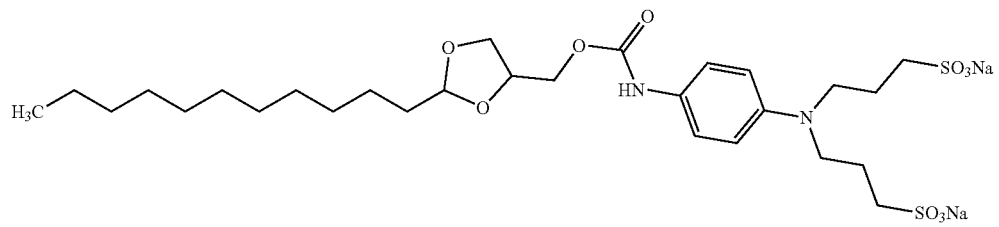

Step 1. (2-undecyl-1,3-dioxolan-4-yl)methyl (4-aminophenyl)carbamate (CS-0838)

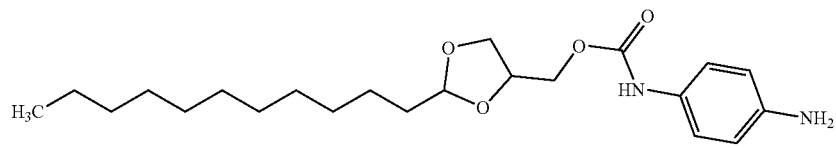

To a solution of 4-nitrophenyl ((2-undecyl-1,3-dioxolan-4-yl)methyl) carbonate (423 mg, 1.0 mmol) in DMF (10 mL) at RT, p-phenylenediamine (216.3 mg, 2.0 mmol) and DIPEA (870 μL, 5.0 mmol) was added. The reaction was stirred at RT for 3 h, LC-MS indicated full conversion. The reaction was poured onto crashed ice and extracted with EtOAc (3×100 mL). The combined organic layers were washed with sat. NaHCO$_3$ aqueous solution (25 mL), H$_2$O (25 mL), brine (25 mL), dried (Na$_2$SO$_4$), concentrated in vacuo to afford the crude. The product was isolated using silica gel purification (Hept/EtOAc, 3/2). $^1$H NMR (400 MHz, CDCl$_3$) δ 7.22-7.08 (m, 2H), 6.65 (m, 2H), 6.48 (br s, 1H), 5.08-4.84 (m, 1H), 4.39-4.07 (m, 3H), 4.03-3.75 (m, 2H), 3.71-3.35 (br s, 2H), 1.81-1.11 (m, 20H), 0.97-0.76 (m, 3H). LC-MS [M+H]$^+$393.

Step 2. Sodium 3,3'-((4-((((2-undecyl-1,3-dioxolan-4-yl)methoxy)carbonyl)amino)phenyl)-azanediyl)bis(propane-1-sulfonate) (CS-0843)

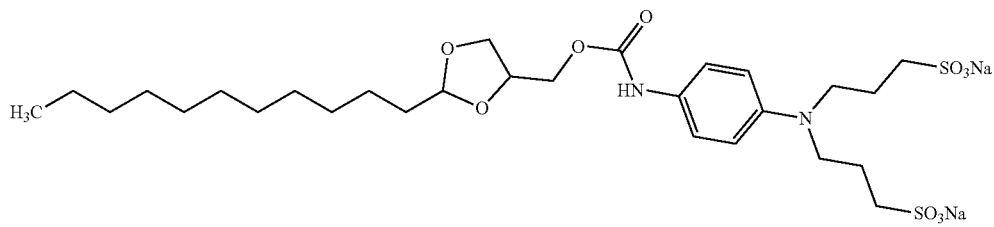

To a solution of (2-undecyl-1,3-dioxolan-4-yl)methyl (4-aminophenyl)carbamate (300 mg, 0.76 mmol) in CH$_3$CN (20 mL), 1,3-propanesultone (373 mg, 3.1 mmol) and DIPEA (1.0 mL, 6.2 mmol) was added. The solution was set to reflux for 48 h. The reaction was cooled down, concentrated, and purified by silica gel chromatography (CH$_2$C$_{12}$/MeOH 7/3). The desired product was purified as DIPEA salt, which was converted to Na salt using ion exchange column. $^1$H NMR (400 MHz, D$_2$O) δ 7.40-7.19 (m, 2H), 7.10-7.10 (m, 2H), 5.03 (br s, 1H), 4.59-3.95 (m, 4H), 3.84-3.64 (m, 1H), 3.55-3.39 (m, 4H), 2.93 (t, J=7.7 Hz, 4H), 2.10-1.90 (m, 4H), 1.77-1.57 (m, 2H), 1.39-1.09 (m, 18H), 0.94-0.78 (m, 3H). LC-MS [M-Na]+659.

Example 23

Sodium 3,3'-((4-(((2,2-bis(pentyloxy)propoxy)carbonyl)amino)phenyl)azanediyl) bis(propane-1-sulfonate) (CS-0853)

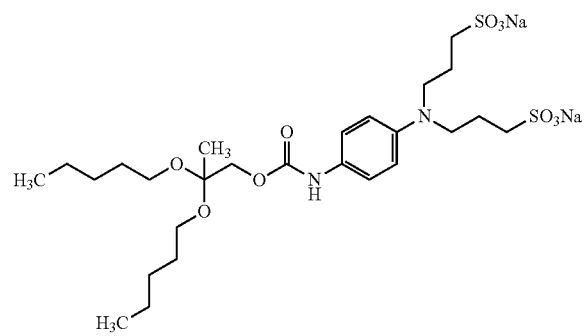

Step 1. 2,2-Bis(pentyloxy)propyl (4-aminophenyl)carbamate (CS-0840)

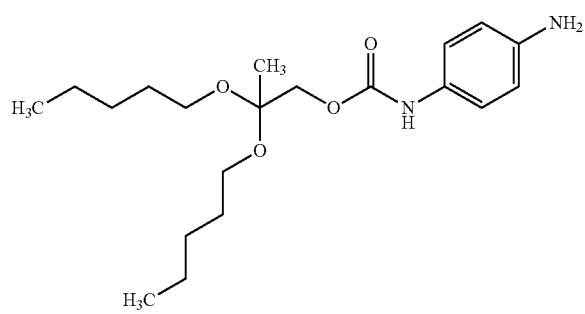 [SMILES: CCCCCOC(C)(COC(=O)Nc1ccc(N)cc1)OCCCCC]

To a solution of 4-nitrophenyl 2,2-bis(pentyloxy)propyl (4-nitrophenyl) carbonate (278 mg, 0.7 mmol) in DMF (10 mL) at RT, p-phenylenediamine (113 mg, 1.1 mmol) and DIPEA (488 μL, 2.8 mmol) was added. The reaction was stirred at RT for 3 h. LC-MS indicated full conversion. The reaction was poured onto crashed ice and extracted with EtOAc (3×100 mL). The combined organic layers were washed with sat. NaHCO$_3$ aqueous solution (25 mL), H$_2$O (25 mL), brine (25 mL), dried (Na$_2$SO$_4$), concentrated in vacuo to afford the crude. The product was isolated using silica gel purification (Hept/EtOAc, 3/2). $^1$H NMR (400 MHz, CDCl$_3$) δ 7.18 (d, J=8.2 Hz, 2H), 6.86-6.65 (m, 2H), 6.54 (s, 1H), 4.64 (d, J=54.4 Hz, 2H), 4.13 (s, 2H), 3.59-3.29 (m, 4H), 1.70-1.46 (m, 4H), 1.43-1.19 (m, 11H), 0.98-0.76 (m, 6H). LC-MS [M+H]+ 367.

Step 2. Sodium 3,3'-((4-(((2,2-bis(pentyloxy)propoxy)carbonyl)amino)phenyl)azanediyl) bis(propane-1-sulfonate) (CS-0853)

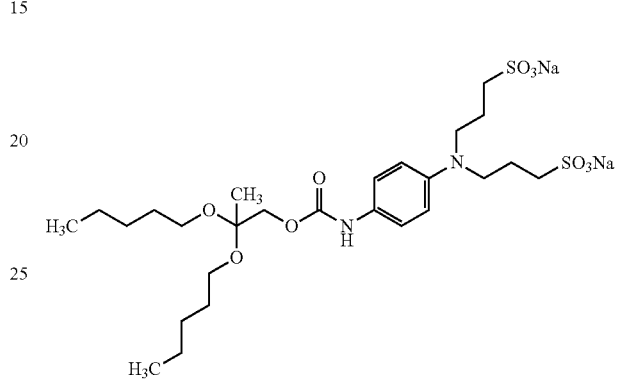

To a solution of 2,2-bis(pentyloxy)propyl (4-aminophenyl)carbamate (240 mg, 0.65 mmol) in CH$_3$CN (20 mL), 1,3-propanesultone (172 μL, 2.0 mmol) and DIPEA (560 μL, 3.0 mmol) was added. The solution was set to reflux for 48 h. The reaction was cooled down, concentrated, and purified by silica gel chromatography (CH$_2$C$_{12}$/MeOH 7/3). The desired product was purified as DIPEA salt, which was converted to Na salt using ion exchange column. $^1$H NMR (400 MHz, CD$_3$OD) δ 7.21 (d, J=8.5 Hz, 2H), 6.76 (d, J=8.5 Hz, 2H), 4.06 (s, 2H), 3.54-3.37 (m, 8H), 2.89-2.75 (m, 4H), 2.12-1.93 (m, 4H), 1.53 (qd, J=7.2, 2.9 Hz, 4H), 1.41-1.26 (m, 11H), 0.97-0.82 (m, 6H). LC-MS [M-Na]+633.

Example 24

Sodium 3-(((2,2-bis((3,3,4,4,5,5,6,6,6-nonafluorohexyl)oxy)propoxy)carbonyl)amino)propane-1-sulfonate (ZZ-0842)

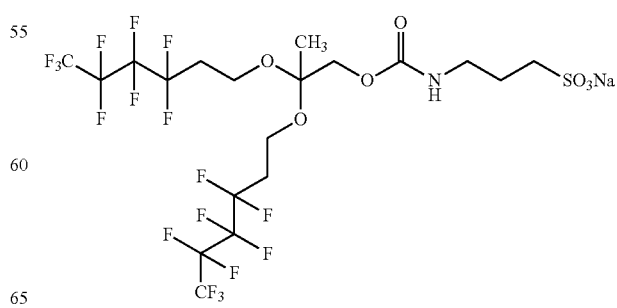

Step 1. 3,3,4,4,5,5,6,6,6-nonafluorohexyl 2,2-bis((3,3,4,4,5,5,6,6,6-nonafluorohexyl)oxy)propanoate (ZZ-0835)

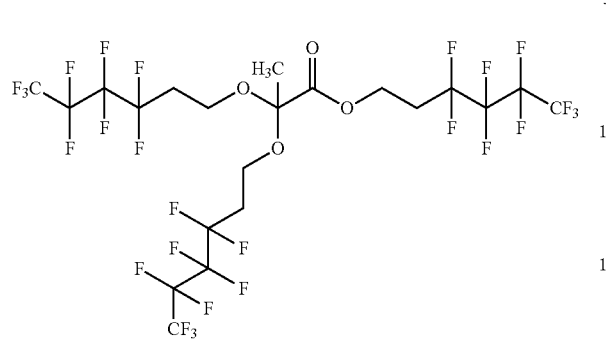

To a solution of methyl pyruvate (5.0 g, 49 mmol) and 3,3,4,4,5,5,6,6,6-nonafluorohexan-1-ol (51.7 g, 196 mmol) in toluene (50 mL), p-toluenesulfonic acid (843 mg, 4.9 mmol) was added. The mixture was heated to reflux using a Dean Stark trap condenser for 2 d. The reaction was neutralized with NaHCO₃ (sat) (20 mL). The mixture was extracted with ethyl acetate, the organic layer was dried with sodium sulfate, filtered, concentrated, and purified with silica gel chromatography (0-10% EtOAc/heptane) to afford desired product (27.0 g, 65%) as an oil.

Step 2. 2,2-bis((3,3,4,4,5,5,6,6,6-nonafluorohexyl)oxy)propan-1-ol (ZZ-0838)

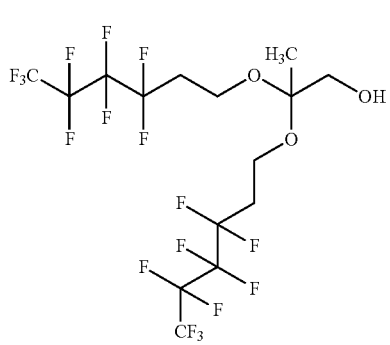 [SMILES: CC(CO)(OCCC(F)(F)C(F)(F)C(F)(F)C(F)(F)F)OCCC(F)(F)C(F)(F)C(F)(F)C(F)(F)F]

To a solution of 3,3,4,4,5,5,6,6,6-nonafluorohexyl 2,2-bis((3,3,4,4,5,5,6,6,6-nonafluorohexyl)oxy)propanoate (5.0 g, 5.9 mmol) in THF (40 mL) at 0° C., lithium aluminum hydride (2.7 mL of 2.4 M solution in THF, 6.5 mmol) was added. The mixture was then stirred at RT for 1 h. The reaction was quenched with water:ethyl acetate (4:4 mL) and potassium sodium tartrate (50 mL). The mixture was washed with ethyl acetate dried with sodium sulfate, filtered, concentrated, and purified with silica gel chromatography (0-20% EtOAc/heptane) to afford desired product (1.0 g, 29%) as an oil.

Step 3. 2,2-bis((3,3,4,4,5,5,6,6,6-nonafluorohexyl)oxy)propyl (4-nitrophenyl) carbonate (ZZ-0839)

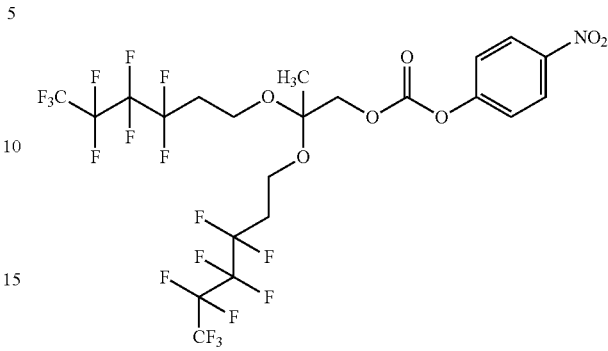

To a solution of 2,2-bis((3,3,4,4,5,5,6,6,6-nonafluorohexyl)oxy)propan-1-ol (1.0 g, 1.7 mmol) in THF (20 mL) at 0° C., 4-nitrophenyl carbonochloridate (0.52 g, 2.6 mmol) and pyridine (0.41 g, 5.1 mmol) was added. The suspension stirred for at 0° C. for 2 h. The reaction was diluted with heptane (100 mL), and the white solid filtered. The filtrate was concentrated and purified with silica gel chromatography to afford crude product.

Step 4. Sodium 3-(((2,2-bis((3,3,4,4,5,5,6,6,6-nonafluorohexyl)oxy)propoxy)carbonyl)amino)propane-1-sulfonate (ZZ-0842)

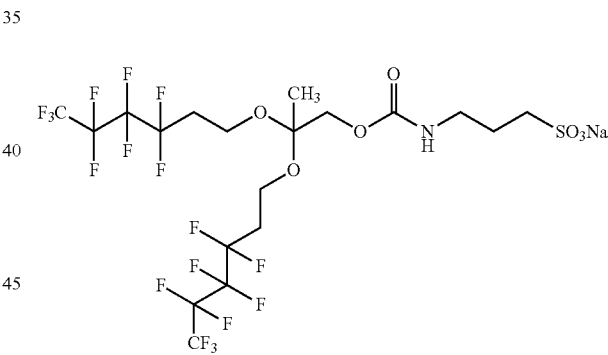

To a solution of 2,2-bis((3,3,4,4,5,5,6,6,6-nonafluorohexyl)oxy)propyl (4-nitrophenyl) carbonate (0.50 g, 0.67 mmol) in THF (20 mL), 3-aminopropane-1-sulfonic acid tetrabutylammonium (0.38 g, 1.0 mmol) was added. The mixture stirred for 2 h at RT. The reaction was concentrated under vacuum and purified with silica gel chromatography using heptanes/ethyl acetate and then with DCM/MeOH to afford the product as the tetrabutylammonium salt (0.6 g). The tetrabutylammonium product was dissolved in water and methanol (10:1, 10 mL), passed through a bissodium ion exchange resin, and lyophilized to afford desired product as a white solid. $^1$H NMR (400 MHz, Methanol-$d_4$) δ 4.09 (s, 2H), 3.90-3.78 (m, 4H), 3.26 (t, J=6.8 Hz, 2H), 2.89-2.78 (m, 2H), 2.57-2.38 (m, 4H), 2.06-1.90 (m, 2H), 1.41 (s, 3H); MS m/z 748 [M−H−Na]−.

Example 25

Sodium 3-(((2,2-bis((3,3,4,4,5,5,6,6,6-nonafluorohexyl)oxy)propoxy)carbonyl)amino)-2-hydroxypropane-1-sulfonate (ZZ-0850)

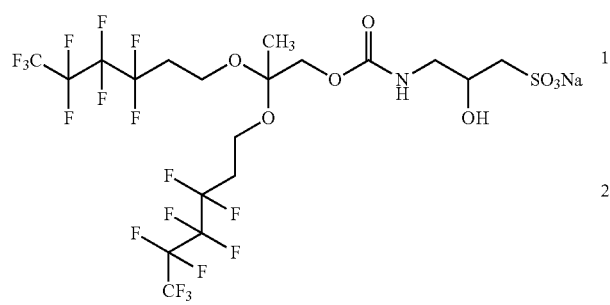

To a solution of 2,2-bis((3,3,4,4,5,5,6,6,6-nonafluorohexyl)oxy)propyl (4-nitrophenyl) carbonate (0.50 g, 0.67 mmol) in THF/water (20/5 mL), 3-amino-2-hydroxypropane-1-sulfonate (0.18 g, 1.0 mmol) and sodium carbonate (0.056 g, 0.67 mmol) was added. The mixture stirred for 4 h at RT. The reaction was concentrated under vacuum and purified with silica gel chromatography using heptanes/ethyl acetate and then with DCM/MeOH to afford desired product (0.15 g, 29%) as a white solid. $^1$H NMR (400 MHz, Methanol-$d_4$) δ 4.20-4.03 (m, 3H), 3.90-3.78 (m, 4H), 3.35-3.24 (m, 2H), 3.01 (dd, J=14.0, 4.0 Hz, 1H), 2.89 (dd, J=14.0, 7.9 Hz, 1H), 2.58-2.39 (m, 4H), 1.42 (s, 3H); MS m/z 764 [M−H−Na]−.

Example 26

Sodium 3-(((2,2-bis((3,3,4,4,5,5,6,6,7,7,8,8,8-tridecafluorooctyl)oxy)propoxy)carbonyl)amino)-2-hydroxypropane-1-sulfonate (ZZ-0846)

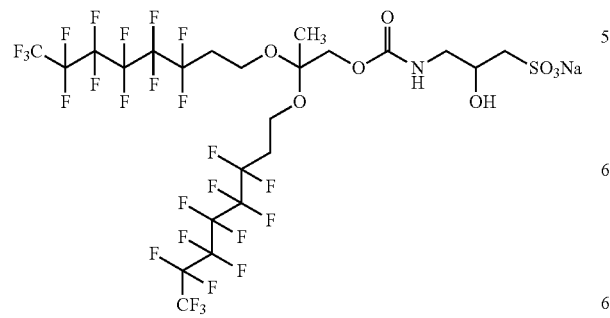

Step 1. 3,3,4,4,5,5,6,6,7,7,8,8,8-tridecafluorooctyl 2,2-bis((3,3,4,4,5,5,6,6,7,7,8,8,8-tridecafluorooctyl)oxy)propanoate (ZZ-0836)

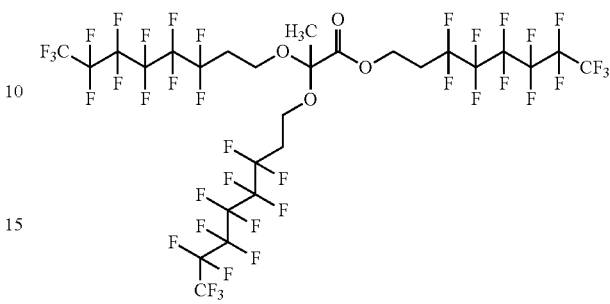

To a solution of methyl pyruvate (5.0 g, 49 mmol) and 3,3,4,4,5,5,6,6,7,7,8,8,8-tridecafluorooctan-1-ol (71.3 g, 196 mmol) in toluene (50 mL), p-toluenesulfonic acid (843 mg, 4.9 mmol) was added. The mixture was heated to reflux using a Dean Stark trap condenser for 2 d. The reaction was neutralized with NaHCO$_3$ (sat) (20 mL). The mixture was extracted with ethyl acetate, the organic layer was dried with sodium sulfate, filtered, concentrated, and purified with silica gel chromatography (0-10% EtOAc/heptane) to afford desired product as an oil.

Step 2. 2,2-bis((3,3,4,4,5,5,6,6,7,7,8,8,8-tridecafluorooctyl)oxy)propan-1-ol (ZZ-0837)

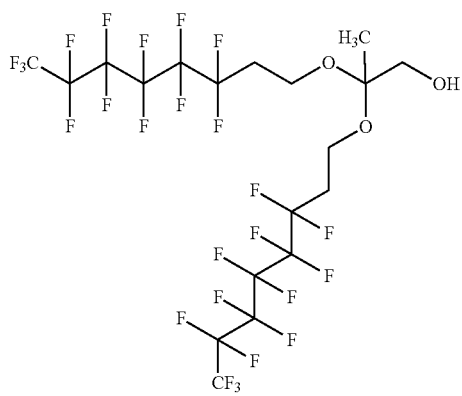 [SMILES: CC(CO)(OCCC(F)(F)C(F)(F)C(F)(F)C(F)(F)C(F)(F)C(F)(F)F)OCCC(F)(F)C(F)(F)C(F)(F)C(F)(F)C(F)(F)C(F)(F)F]

To a solution of 3,3,4,4,5,5,6,6,7,7,8,8,8-tridecafluorooctyl 2,2-bis((3,3,4,4,5,5,6,6,7,7,8,8,8-tridecafluorooctyl)oxy)propanoate (8.0 g, 7.0 mmol) in THF (40 mL) at 0° C., lithium aluminum hydride (3.2 mL of 2.4 M solution in THF, 7.7 mmol) was added. The mixture was then stirred at RT for 1 h. The reaction was quenched with water:ethyl acetate (4:4 mL) and potassium sodium tartrate (50 mL). The mixture was washed with ethyl acetate dried with sodium sulfate, filtered, concentrated, and purified with silica gel chromatography (0-20% EtOAc/heptane) to afford desired product (3.9 g, 71%) as an oil.

Step 3. 2,2-bis((3,3,4,4,5,5,6,6,7,7,8,8,8-tridecafluorooctyl)oxy)propyl (4-nitrophenyl) carbonate (ZZ-0841)

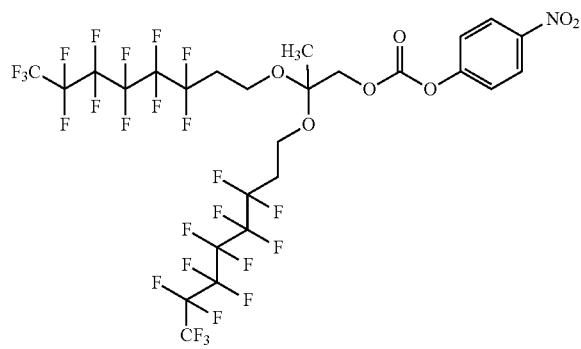 [SMILES: CC(COC(=O)Oc1ccc([N+](=O)[O-])cc1)(OCCC(F)(F)C(F)(F)C(F)(F)C(F)(F)C(F)(F)C(F)(F)F)OCCC(F)(F)C(F)(F)C(F)(F)C(F)(F)C(F)(F)C(F)(F)F]

To a solution of 2,2-bis((3,3,4,4,5,5,6,6,7,7,8,8,8-tridecafluorooctyl)oxy)propan-1-ol (3.0 g, 3.6 mmol) in THF (20 mL) at 0° C., 4-nitrophenyl carbonochloridate (1.1 g, 5.4 mmol) and pyridine (0.85 g, 10.8 mmol) was added. The suspension stirred for at 0° C. for 2 h. The reaction was diluted with heptane (100 mL) and the white solid filtered. The filtrate was concentrated and purified with silica gel chromatography to afford crude product.

Step 4. Sodium 3-(((2,2-bis((3,3,4,4,5,5,6,6,7,7,8,8,8-tridecafluorooctyl)oxy)propoxy)carbonyl)amino)-2-hydroxypropane-1-sulfonate (ZZ-0846)

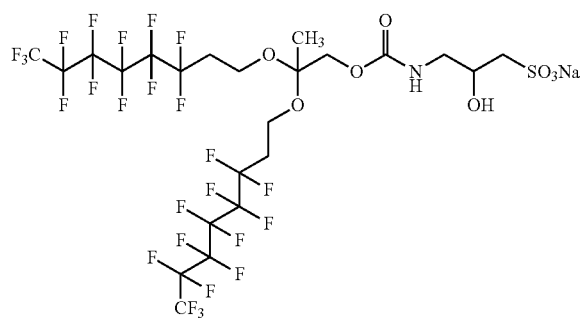

To a solution of 2,2-bis((3,3,4,4,5,5,6,6,7,7,8,8,8-tridecafluorooctyl)oxy)propyl (4-nitrophenyl) carbonate (0.60 g, 0.63 mmol) in THF/water (20/5 mL), 3-amino-2-hydroxypropane-1-sulfonate (0.17 g, 0.95 mmol) and sodium carbonate (0.053 g, 0.63 mmol) was added. The mixture stirred for 4 h at RT. The reaction was concentrated under vacuum and purified with silica gel chromatography using heptanes/ethyl acetate and then with DCM/MeOH to afford desired product (0.15 g, 25%) as a white solid. $^1$H NMR (400 MHz, D$_2$O) δ 4.73-4.62 (m, 3H), 4.49-4.33 (m, 4H), 3.96-3.87 (m, 1H), 3.83-3.70 (m, 1H), 3.62-3.43 (m, 2H), 3.17-2.97 (m, 4H), 1.42 (s, 3H); MS m/z 964 [M–H–Na]–.

Example 27

Sodium 3-(((2,2-bis((3,3,4,4,5,5,6,6,7,7,8,8,8-tridecafluorooctyl)oxy)propoxy)carbonyl)amino)propane-1-sulfonate (ZZ-0849)

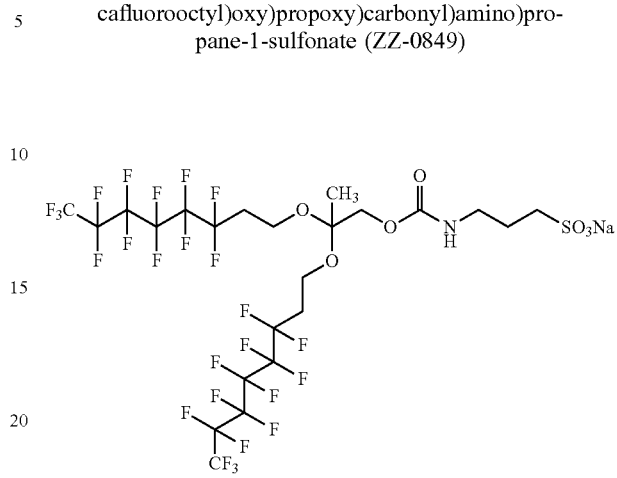

To a solution of 2,2-bis((3,3,4,4,5,5,6,6,7,7,8,8,8-tridecafluorooctyl)oxy)propyl (4-nitrophenyl) carbonate (0.60 g, 0.63 mmol) in ACN/water (5/5 mL), 3-aminopropane-1-sulfonate (0.153 g, 0.95 mmol) and sodium carbonate (0.053 g, 0.63 mmol) was added. The mixture stirred for 4 h at RT. The reaction was concentrated under vacuum and purified with silica gel chromatography using heptanes/ethyl acetate and then with DCM/MeOH to afford desired product (0.15 g, 25%) as a white solid. $^1$H NMR (400 MHz, D$_2$O) δ 3.95 (s, 2H), 3.78-3.57 (m, 4H), 3.14 (t, J=6.9 Hz, 2H), 2.83-2.71 (m, 2H), 2.38-2.17 (m, 4H), 1.91-1.78 (m, 2H), 1.27 (s, 3H); MS m/z 948 [M–H–Na]–.

Example 28

Stability Data

To test for thermal stability (% remaining at 95° C. for 1 h), 20 mM stock solutions of example compounds in DMSO were prepared. The stock solutions were diluted 100-times into a Tris-based PCR buffer and heated to 95° C. for 1 hour in a thermocycler. The solutions were then analyzed by LCMS.

To test for acid stability, a 3% stock solution (9 mg/300 μL) of each example compound was prepared in NanoPure water. A secondary 3 mM stock solution was prepared in NanoPure water. The secondary stock was diluted 6-times in NanoPure water as a control or diluted 6-times into 2.4% TFA-NanoPure water to 2% TFA-NanoPure water for the acid stability experiment. The solutions were heated to 40° C. for 1 hour and analyzed by LCMS.

Compound purity and percent remaining were determined by integrating peaks in the total ion chromatogram using LCMS. Compound peaks were identified in negative mode using the molecular weight without sodium. The mobile phase of acetonitrile and water contained 10 mM ammonium acetate using a Synergi Max-RP column, 50×4.6 mm, 2.5 microns.

TABLE 1

LCMS analysis of thermal and acid stability

| Compound | % remaining after 1 hour at 95° C. in Polymerase Buffer C | % remaining after 1 h at 40° C. in 2% TFA |
|---|---|---|
| JZ-0164 | 93.8 | 0 |
| JZ-0179 | 83.9 | 100 |
| JZ-0177 | 99.4 | 0 |
| HW-0797 | 83.6 | Not soluble |
| HW-0801 | 94.1 | Not soluble |
| RBK-0171 | 13.1 | Not tested |
| RBK-0172 | 8.2 | Not tested |
| RBK-0173 | 81.2 | Not soluble |
| RBK-0168 | 5.4 | Not tested |
| RBK-0169 | 6.0 | Not tested |
| RBK-0170 | 88.3 | 0 |
| TU-1179 | 102.9 | 0 |
| AF-0045 | 89.3 | 0 |
| ZZ-0842 | >99 | 0 |
| ZZ-0846 | 93.4 | 2 |
| ZZ-0849 | >99 | 2 |
| ZZ-0850 | 90.5 | 0 |
| JRW-1564 | 95.2 | 1 |
| JRW-1565 | 95.7 | 1 |
| JRW-1573 | 95.0 | 0 |
| JRW-1574 | 92.8 | 4 |
| SL-1735 | 93.6 | 0 |
| HW-0805 | 94.2 | Not soluble |
| HW-0807 | Not soluble | Not soluble |
| CS-0843 | >99 | 22 |
| CS-0853 | 2.5 | 42 |

Example 29

Protein Solubilizing and Denaturing Efficiency

Figure 2:
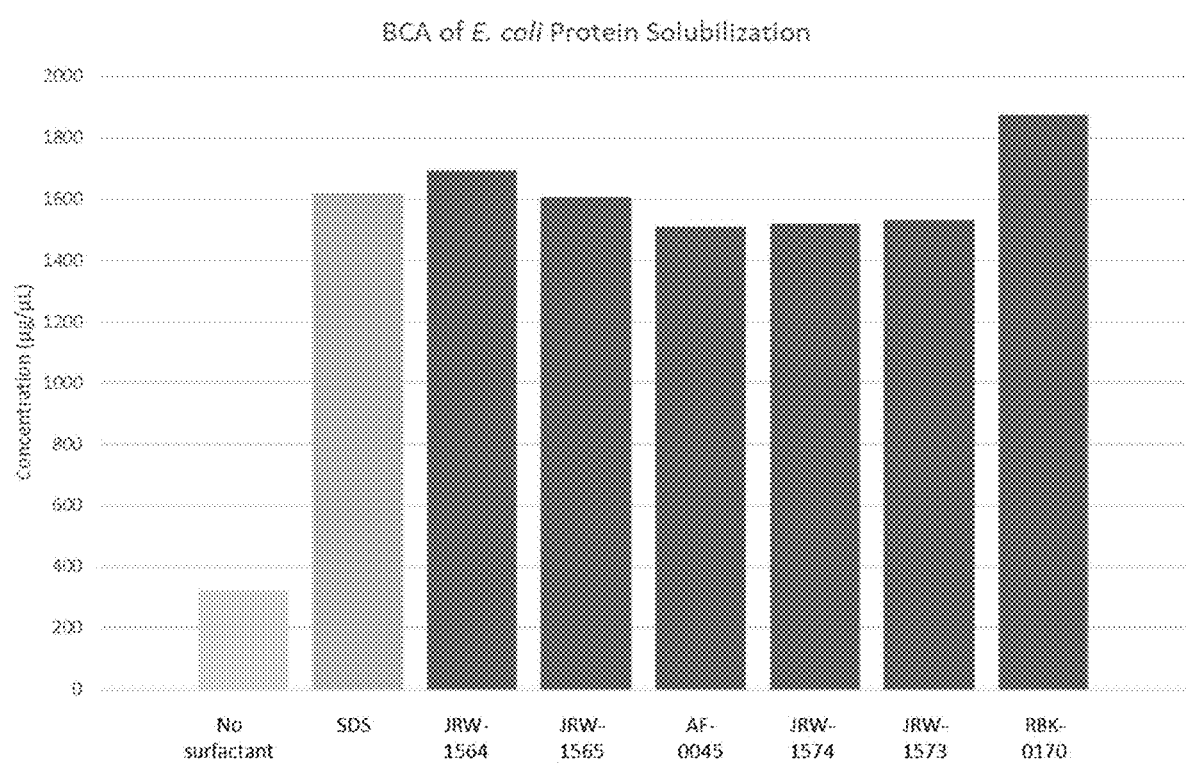
FIG. 2 shows results from representative BCA assays of solubilized E. coli protein pellets following incubation with compounds described herein, as described in Example 31.

To test for protein solubilizing ability, 4% stock solutions (12 mg/300 µL) of example compounds were prepared in NanoPure water. The stock solution was diluted 8 times in 50 mM ammonium bicarbonate, pH 7.8 (0.5% final) and added to acetone-precipitated protein pellets from lysed E. coli. The samples were incubated at 50° C. with shaking at 1200 rpm overnight and then analyzed by SDS PAGE and BCA. As a control, an acetone-precipitated protein pellet was solubilized under the same conditions with 0.5% SDS in 50 mM ammonium bicarbonate, pH 7.8. Representative SDS-PAGE gels of the solubilized E. coli protein pellets are shown in FIG. 1. Results from representative BCA assay of the solubilized E. coli protein pellets are shown in FIG. 2. SDS is one of the best performing surfactants for protein solubilization and extraction, but is not compatible with mass spectrometry. These results demonstrate that many of the example compounds are able to match or exceed the performance of sodium dodedecyl sulfate (SDS) in solubilizing or extracting proteins.

Figure 3:
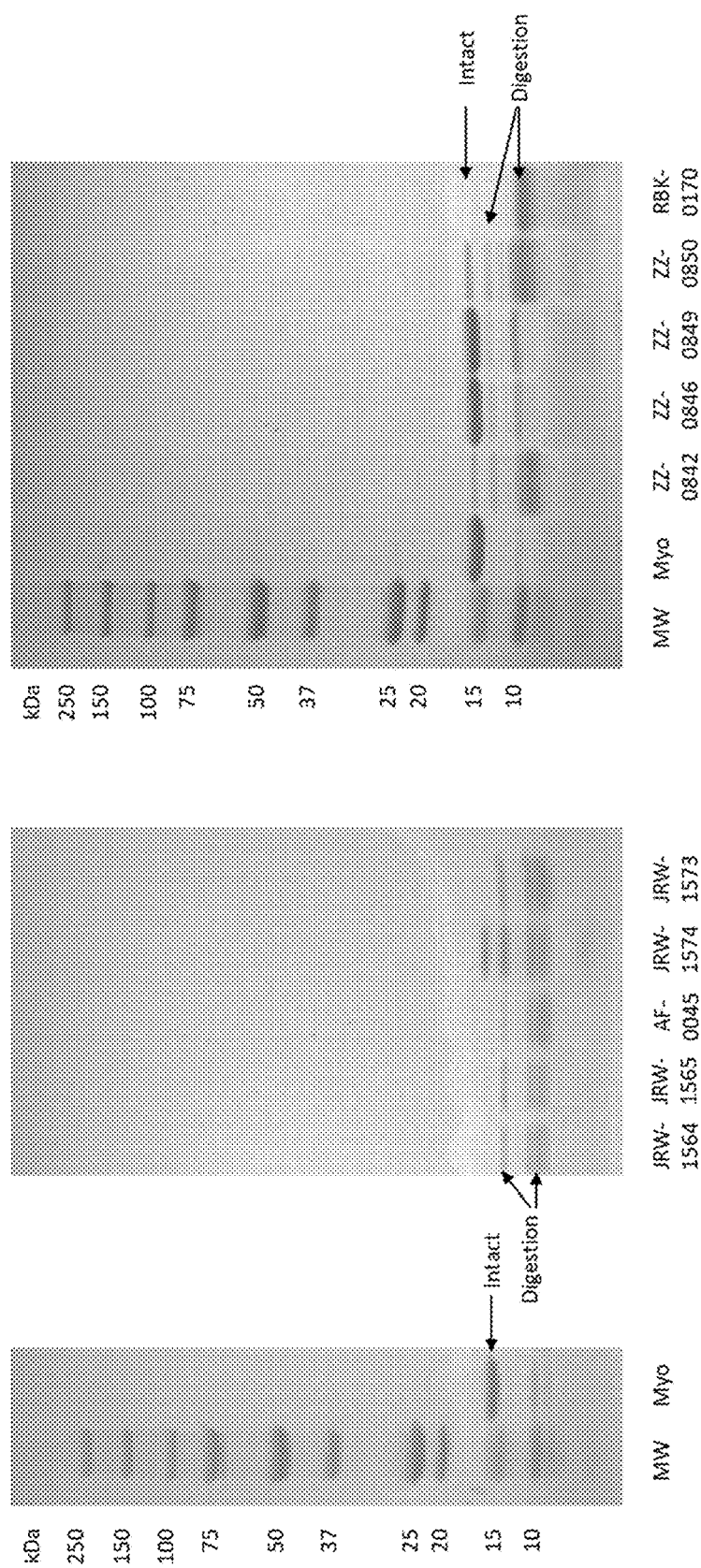
FIG. 3 shows representative SDS-PAGE gels of myoglobin denaturation and trypsin digest products following incubation with compounds described herein, as described in Example 31.

To test for protein denaturing ability, 4% stock solutions (12 mg/300 µL) of each example compound were prepared in NanoPure water. The stock solution was diluted 40 times in 50 mM ammonium bicarbonate, pH 7.8 (0.1% final) with 20 µg of myoglobin (Sigma) and 0.5 µg of Trypsin Gold (Promega). The samples were incubated at 37° C. with shaking at 1200 rpm for 40 min and then analyzed by SDS PAGE. The assay measures protein denaturation and trypsin compatibility. Myoglobin is only digested if it is sufficiently denatured by surfactant. Representative SDS-PAGE gels of the myoglobin denaturation and trypsin digest products are shown in FIG. 3. The results from this assay show that the example compounds are able to sufficiently denture myoglobin such that it is successfully digested by trypsin protease. The example compounds offer an advantage in denaturing proteins to allow for improved digestion by trypsin.

Example 30

Trypsin Compatibility

Figure 4:
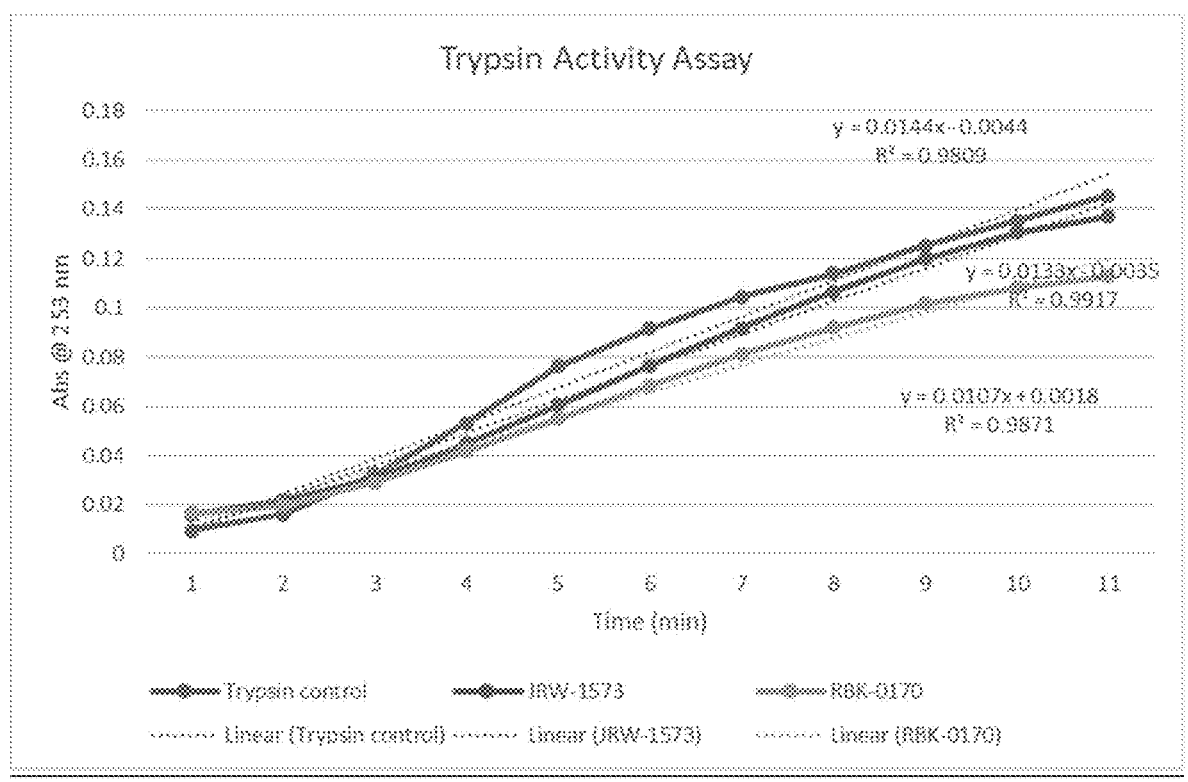
FIG. 4 shows results from representative trypsin assays conducted in the presence of compounds described herein, as described in Example 32.

Compatibility of the different compounds with trypsin was tested using a trypsin-specific substrate, benzoyl-L-arginine ethyl ester hydrochloride (BAEE). 4% stock solutions (12 mg/300 µL) of example compounds were prepared in NanoPure water. The stock solution was diluted 40 times in 50 mM ammonium bicarbonate, pH 7.8 (0.1% final) with 200 µM of BAEE. The entire sample was transferred to an individual well in a 96-well UV-compatible microplate. The absorbance of the sample was measured at 253 nm using a TECAN M1000 plate reader. After 2 minutes, 0.2 µg of Trypsin Gold (Promega) was added to the reaction and absorbance at 253 nm was monitored every minute over a period of 10 minutes. The resulting activity measurement was compared to the control of trypsin without surfactant present. Results from representative trypsin assays are shown in FIG. 4 and data are summarized in Table 2. Trypsin is the most commonly used protease for the digestion of protein mass spectrometry samples. The results from this experiment indicate that the compounds have a minimal effect on trypsin activity and can be used during the sample digestion step.

TABLE 2

Representative trypsin activity assay with surfactant present

| Surfactant | Slope | % Trypsin Activity |
|---|---|---|
| Trypsin | 0.0144 | 100 |
| JRW-1573 | 0.0133 | 92 |
| RBK-0170 | 0.0107 | 74 |

Example 31

Proteomic Mass Spectrometry

To determine the effect of surfactant on protein sample preparation for mass spec analysis, 4% stock solutions (12 mg/300 µL) of example compounds were prepared in NanoPure water. The stock solution was diluted 8 times in 50 mM ammonium bicarbonate, pH 7.8 (0.5% final) and added to acetone-precipitated protein pellets from lysed E. coli. The samples were incubated at 50° C. with shaking at 1200 rpm overnight to solubilize the protein pellet. The resulting samples were reduced with 5 mM dithiothreitol (DTT) at 37° C. for 1 h, followed by alkylation with 15 mM iodoacetamide (IAM) at room temperature for 1 h. Each sample was digested with Trypsin Gold (Promega) at a ratio of 1:40, in µg of trypsin per µg protein, at 50° C. with shaking at 1200 rpm for 3 h. Surfactants were removed by centrifuging at 16,000×g at room temperature for 5 min and then cleaned up with ZipTips (OMIX) following the manufacturer's instructions.

All samples were analyzed by LC-MS/MS with a Thermo Scientific Q Exactive hybrid quadrupole-Orbitrap mass spectrometer. The data was analyzed with MASCOT and Scaffold software to determine the number of protein and peptide identifications. As a control, protein pellets from lysed E. coli were solubilized and digested under the same conditions in the presence of 0.1% RapiGest (surfactant provided by Waters). Results are summarized in Table 3. The mass spectrometry data shows that the example compounds increased the overall protein and peptide identifications when compared with a currently available mass spec compatible surfactant, RapiGest (Waters).

TABLE 3

Representative mass spectrometry identifications from *E. coli* protein digestions

| Sample | Peptide IDs | Protein IDs |
|---|---|---|
| JRW-1573 | 2668 | 830 |
| RBK-0170 | 2111 | 882 |
| RapiGest (Waters product) | 2628 | 747 |

The invention claimed is:

1. A compound of formula (I):

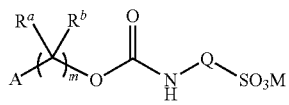

or a salt thereof, wherein:

A is selected from:

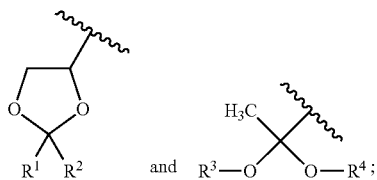

$R^1$ is selected from hydrogen, $C_1$-$C_{12}$ alkyl, $C_2$-$C_{12}$ alkenyl, and $C_1$-$C_{12}$ haloalkyl;

$R^2$ is selected from $C_4$-$C_{20}$ alkyl, $C_4$-$C_{20}$ alkenyl, and $C_4$-$C_{20}$ haloalkyl;

each $R^3$ is independently selected from $C_1$-$C_{12}$ alkyl, $C_2$-$C_{12}$ alkenyl, and $C_1$-$C_{12}$ haloalkyl;

m is 1, 2, or 3;

$R^a$ and $R^b$, at each occurrence, are independently selected from hydrogen and $C_1$-$C_3$ alkyl;

Q is selected from $C_1$-$C_6$-alkylene, and $C_1$-$C_6$-hydroxyalkylene;

or the group -Q-$SO_3$M has a formula:

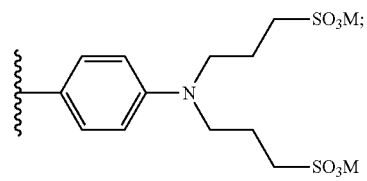

and each M is independently selected from hydrogen, an alkali metal cation, and $NR_4^+$, wherein each R is independently selected from hydrogen and $C_1$-$C_{12}$ alkyl.

2. The compound of claim 1, or a salt thereof, wherein:

A is:

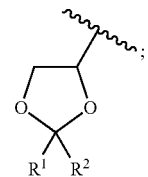

$R^2$ is $C_6$-$C_{12}$ alkyl; and $R^1$ is selected from hydrogen, methyl, and $C_4$-$C_8$ alkyl.

3. The compound of claim 1, or a salt thereof, wherein A is selected from:

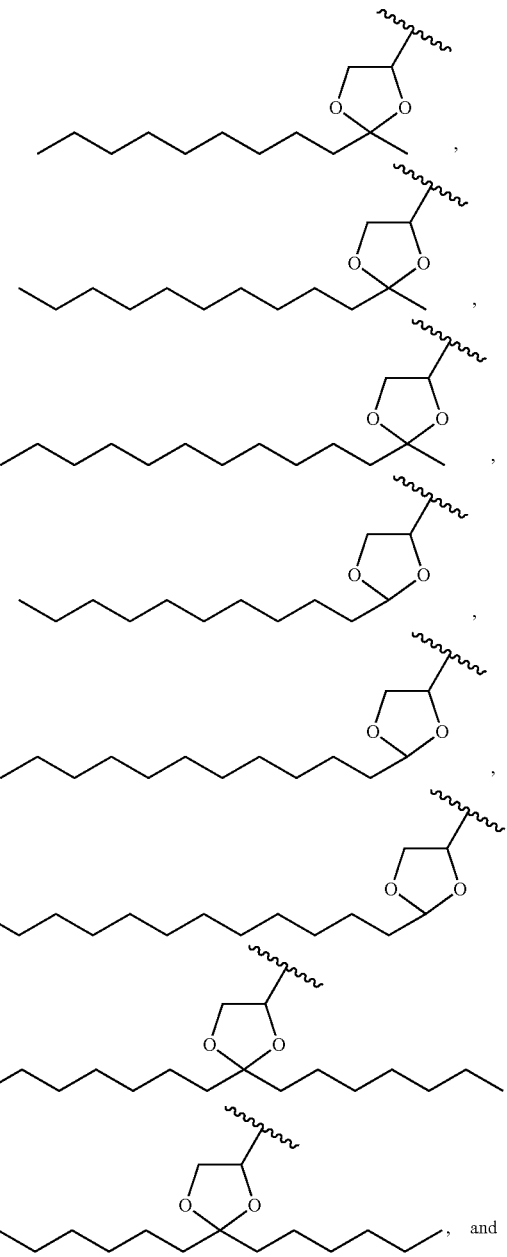

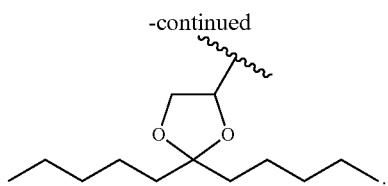

4. The compound of claim 1, or a salt thereof, wherein:
A is:

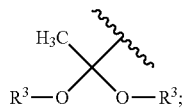

and
each $R^3$ is selected from $C_4$-$C_8$ alkyl and $C_4$-$C_8$ haloalkyl.

5. The compound of claim 1, or a salt thereof, wherein:
A is:

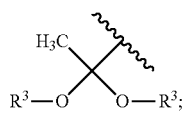

and
each $R^3$ is selected from $-(CH_2)_x-(CF_2)_y-CF_3$, wherein x is 1, 2, 3, or 4, and y is 1, 2, 3, 4, 5, 6, or 7.

6. The compound of claim 1, or a salt thereof, wherein A is selected from:

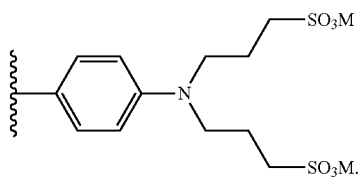

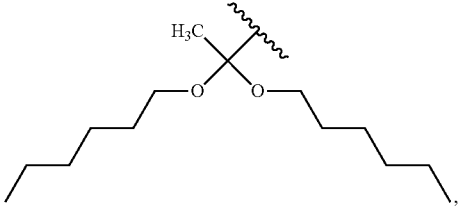

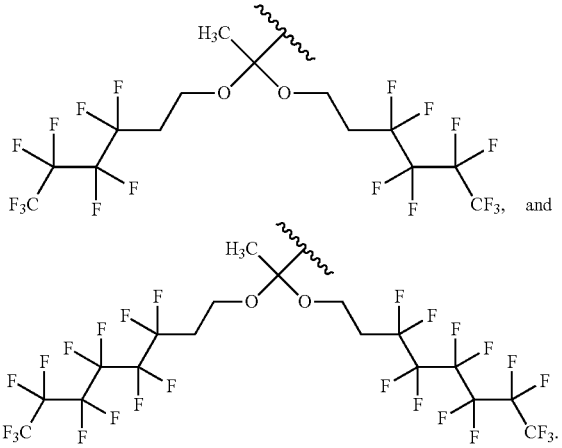

7. The compound of claim 1, or a salt thereof, wherein:
m is 1; and
$R^a$ and $R^b$ are each hydrogen.

8. The compound of claim 1, or a salt thereof, wherein:
Q is selected from $-CH_2CH_2CH_2-$ and $-CH_2CH(OH)CH_2-$.

9. The compound of claim 1, or a salt thereof, wherein the group -Q-$SO_3$M has formula:

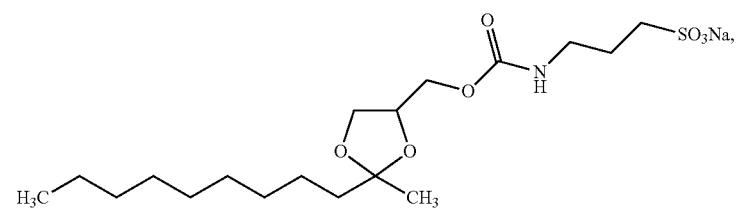

10. The compound of claim 1, selected from:

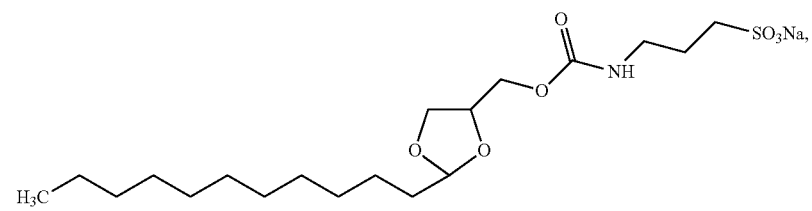

-continued
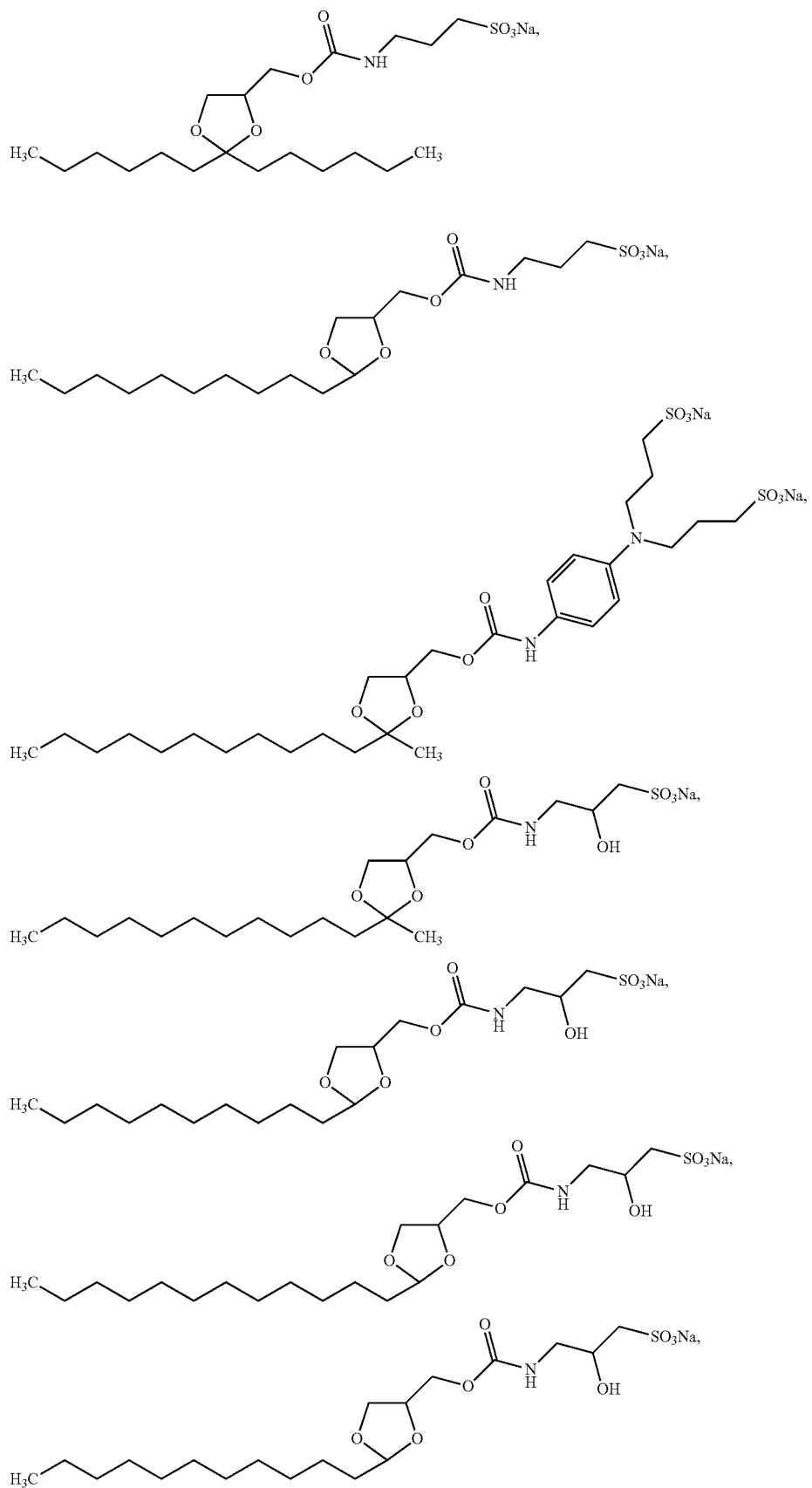

83 84
-continued
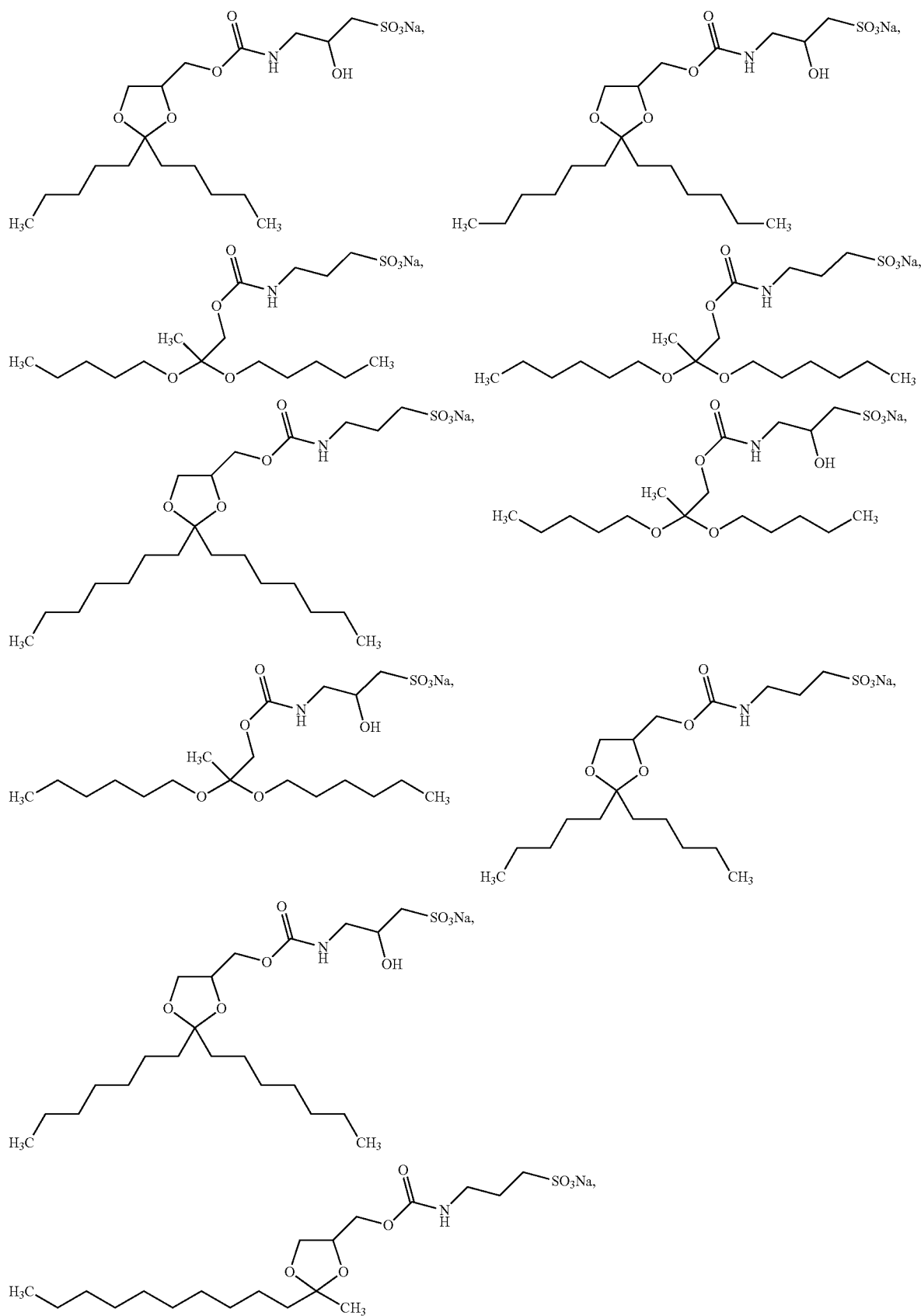

-continued
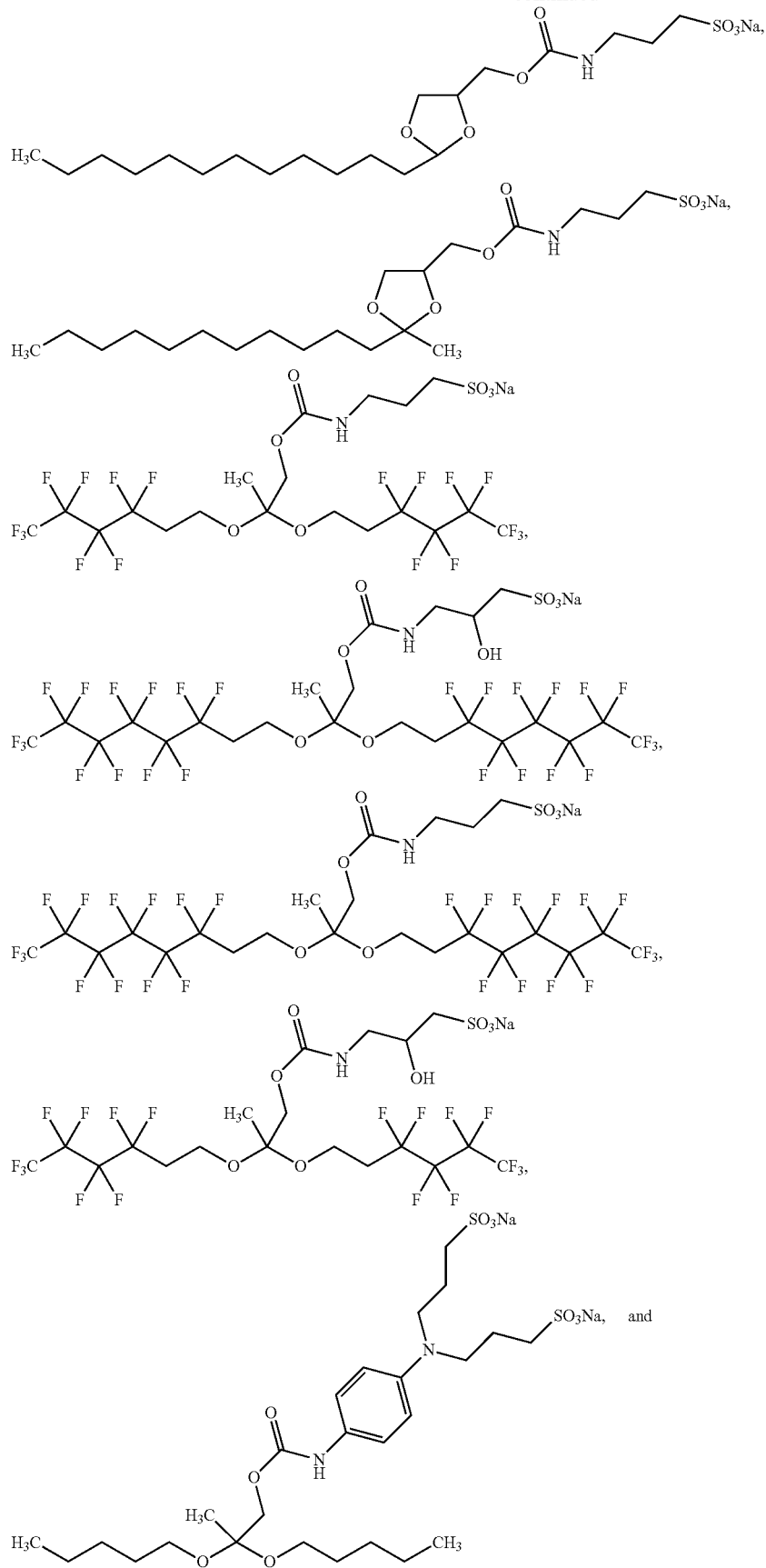

-continued

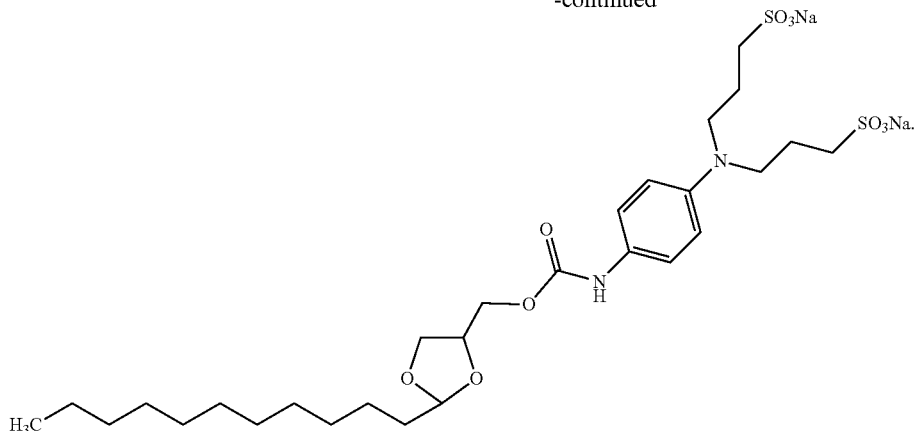

11. A method for digesting a protein, comprising:
  contacting a sample comprising at least one protein with a protein digestion reagent and a compound of claim 1, or a salt thereof,
  to thereby provide a sample comprising at least one digested protein.

12. The method of claim 11, wherein the sample is a gel, a solid support, or a solution.

13. The method of claim 11, wherein the protein digestion reagent comprises a protease, cyanogen bromide, hydroxylamine, or any combination thereof.

14. The method of claim 13, wherein the protein digestion reagent comprises a serine protease selected from trypsin, chymotrypsin, and Lys-C.

15. The method of claim 11, further comprising degrading the compound after the contacting step.

16. The method of claim 15, wherein the degradation step comprises contacting the compound with an acid.

17. The method of claim 15, wherein the compound self-decomposes after the contacting step.

18. The method of claim 11, further comprising isolating and/or analyzing at least one digested protein fragment.

19. A composition comprising a gel and a compound of claim 1.

20. A method for extracting a peptide from a gel, comprising:
  contacting the gel with a compound of claim 1 and an aqueous solution; and
  separating the aqueous liquid from the gel,
  to thereby provide a solution comprising the peptide.

* * * * *

UNITED STATES PATENT AND TRADEMARK OFFICE
CERTIFICATE OF CORRECTION

PATENT NO. : 11,939,311 B2
APPLICATION NO. : 16/986682
DATED : March 26, 2024
INVENTOR(S) : Joel Walker et al.

It is certified that error appears in the above-identified patent and that said Letters Patent is hereby corrected as shown below:

In the Claims

Claim 1, Column 77, Lines 35-38, the right-hand formula appears as follows:

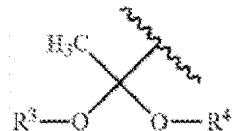

Whereas it should appear as:

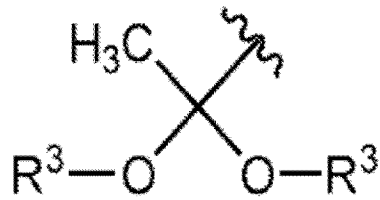

Signed and Sealed this
Twenty-eighth Day of May, 2024

Katherine Kelly Vidal
*Director of the United States Patent and Trademark Office*